United States Patent [19]
Holt et al.

[11] Patent Number: 6,149,903
[45] Date of Patent: *Nov. 21, 2000

[54] CHARACTERIZED BRCA1 AND BRCA2 PROTEINS AND SCREENING AND THERAPEUTIC METHODS BASED ON CHARACTERIZED BRCA1 AND BRCA2 PROTEINS

[75] Inventors: Jeffrey T. Holt, Brentwood; Roy A. Jensen, Franklin, both of Tenn.; Mary-Claire King, Seattle, Wash.; David L. Page, Nashville, Tenn.; Csilla I. Szabo, Seattle, Wash.; Thomas L. Jetton, Kingston Springs, Tenn.; Cheryl L. Robinson-Benion; Marilyn E. Thompson, both of Nashville, Tenn.

[73] Assignees: Vanderbilt University, Nashville, Tenn.; University of Washington, Seattle, Wash.

[ * ] Notice: This patent is subject to a terminal disclaimer.

[21] Appl. No.: 09/099,753

[22] Filed: Jun. 18, 1998

Related U.S. Application Data

[63] Continuation of application No. 08/603,753, Feb. 20, 1996, Pat. No. 5,891,857.

[51] Int. Cl.$^7$ .................................................. A61K 48/00

[52] U.S. Cl. ........................ 424/93.2; 514/44; 536/23.1; 435/320.1; 435/325; 435/455; 435/458

[58] Field of Search ............................ 514/44; 424/93.2, 424/93.21; 435/320.1, 325, 455, 458; 536/23.1

[56] References Cited

U.S. PATENT DOCUMENTS

| | | | |
|---|---|---|---|
| 4,675,285 | 6/1987 | Clark et al. | 435/6 |
| 5,399,346 | 3/1995 | Anderson et al. | 424/93.21 |
| 5,434,064 | 7/1995 | Schlessinger et al. | 435/455 |
| 5,654,155 | 8/1997 | Murphy et al. | 435/6 |
| 5,891,857 | 4/1999 | Holt et al. | 514/44 |

FOREIGN PATENT DOCUMENTS

| | | |
|---|---|---|
| 0699754A1 | 3/1996 | European Pat. Off. . |
| 0705902A1 | 4/1996 | European Pat. Off. . |
| 0705903A1 | 4/1996 | European Pat. Off. . |
| 95/19369 | 7/1995 | WIPO . |
| 95/25429 | 9/1995 | WIPO . |
| 95/25813 | 9/1995 | WIPO . |
| 96/05306 | 2/1996 | WIPO . |
| 96/05307 | 2/1996 | WIPO . |
| 96/05308 | 2/1996 | WIPO . |
| 97/29213 | 8/1997 | WIPO . |
| 97/301308 | 8/1997 | WIPO . |

OTHER PUBLICATIONS

Meng et al., Gene Therapy of Cancer, Chapter 1, pp. 3–20, 1999.

Tait et al., Breast Disease, 10, 1,2, 89–98, 1998.

Anderson, Nature, vol. 392, 25–30, Apr. 1998.

Tait et al., Clinical Cancer Res., vol. 5, 1707–1714, 1999.

Wooster et al., "Identification of the Breast Cancer Susceptibility Gene BRCA2", *Nature,* vol. 378, (Dec. 21/28 1995), pp. 789–792.

Miki et al., "A Strong Candidate for the Breast and Ovarian Cancer Susceptibility Gene BRCA1", *Science,* vol. 1, (Oct. 7, 1994), pp. 66–71.

Holt et al., "Growth Retardation and Tumour Inhibition by BRCA1", *Nature Genetics,* vol. 12, (Mar. 1996), pp. 298–302.

Ormiston, "Hereditary Breast Cancer", *European Journal of Cancer Care,* vol. 5, (1996), pp. 13–20.

Jones et al., "Molecular Genetics of Sporadic and Familial Breast Cancer", *Cancer Surveys,* vol. 25, (1995), pp. 315–334.

"Molecular Biology/Biochemistry", Proceedings of the American Association for Breast Cancer Research, vol. 37, (Mar. 1996), p. 516.

Chen et al., "Aberrant Subcellular Localization of BRCA1 in Breast Cancer", *Science,* vol. 270, (Nov. 3, 1995), pp. 789–791.

Cornelius et al., "High Allele Loss Rates at 17q12–q21 in Breast and Ovarian Tumors from BRCA1–Linked Families", *Genes, Chromosomes & Cancer,* vol. 13, (1995), pp. 201–210.

Gayther et al., "Germline Mutations of the BRCA1 Gene in Breast and Ovarian Cancer Families Provide Evidence for a Genotype–Phenotype Correlation", *Nature Genetics,* vol. 11, (Dec. 1995), pp. 428–433.

Gudas et al., "Hormone–Dependent Regulation of BRCA1 in Human Breast Cancer Cells", *Cancer Research,* vol. 55, (Oct. 15, 1995), pp. 4561–4565.

Hosking et al., "A Somatic BRCA1 Mutation in an Ovarian Tumour", *Nature Genetics,* vol. 9, (Apr. 1995), pp. 343–344.

Huttner et al., "The Granin (Chromogranin/Secretogranin) Family", *TIBS,* vol. 16, (Jan. 1991), pp. 27–30.

(List continued on next page.)

*Primary Examiner*—Scott D. Priebe
*Assistant Examiner*—Dave Trong Nguyen
*Attorney, Agent, or Firm*—Jenkins & Wilson, P.A.

[57] ABSTRACT

Genetic analysis of familial breast and ovarian cancer indicates that BRCA1 is a tumor suppressor gene. The BRCA1 gene encodes a 190 kDa protein with sequence homology and biochemical analogy to the granin family of proteins. Granins are secreted from endocrine cells via the regulated secretory pathway and are proteolytically cleaved to yield biologically active peptides. BRCA1 protein localizes to secretory vesicles, and was demonstrated to be secreted. Gene transfer of BRCA1 inhibits growth and tumorigenesis of breast and ovarian cancer cells, but not colon or lung cancer cells or fibroblasts, suggesting that BRCA1 encodes a tissue-specific growth inhibitor. Thus, BRCA1 is a secreted growth inhibitor and functions by a mechanism not previously described for tumor suppressor genes. The BRCA2 breast and ovarian cancer gene encodes a protein that also includes a granin region, indicating that the BRCA2 protein is also a secreted tumor suppressor. Therapeutic methods using the BRCA1 and BRCA proteins and genes are also described. A method of screening for the receptors of the BRCA1 protein and BRCA2 proteins is also described.

4 Claims, 28 Drawing Sheets

OTHER PUBLICATIONS

Marquis et al., "The Developmental Pattern of BRCA1 Expression Implies a Role in Differentiation of the Breast and Other Tissues", *Nature Genetics*, vol. 11, (Sep. 1995), pp. 17–26.

Merajver et al., "Somatic Mutations in the BRCA1 Gene in Sporadic Ovarian Tumours", *Nature Genetics*, vol. 9, (Apr. 1995), pp. 439–443.

Thompson et al., "Decreased Expression of BRCA1 Accelerates Growth and is Often Present During Sporadic Breast Cancer Progression", *Nature Genetics*, vol. 9, (Apr. 1995), pp. 444–450.

Lemoine, "Molecular Biology of Breast Cancer", *Annals of Oncology*, 5 (Supp. 4) pp. S31–S37.

Weber et al., "Familial Breast Cancer", *Cancer Supplement*, vol. 74, No. 3, (Aug. 1, 1994), pp. 1013–1020.

Takahashi et al., "Mutation Analysis of the BRCA1 Gene in Ovarian Cancers", *Cancer Research*, vol. 55, (Jul. 15, 1995), pp. 2998–3002.

Narod, "Genetics of Breast and Ovariana Cancer", *British Medical Bulletin*, vol. 50, No. 3, (1994), pp. 656–676.

Hall et al., "Linkage of Early–Onset Familial Breast Cancer to Chromosome 17q21", *Science*, vol. 250, (Dec. 21, 1990), pp. 1684–1689.

Helzlsouer, "Epidemiology, Prevention and Early Detection of Breast Cancer", *Current Opinion in Oncology*, vol. 7, (1995), pp. 489–494.

Szabo et al., "Inherited Breast and Ovarian Cancer", *Human Molecular Genetics*, vol. 4, pp. 1811–1817.

Easton et al., "Inherited Susceptibility to Breast Cancer", *Cancer Surveys*, vol. 18, pp. 95–113.

Steeg, "Granin Expectations in Breast Cancer?", *Nature Genetics*, vol. 12, (Mar. 1996), pp. 223–225.

Burtness, "Oncology and Hematology", *JAMA*, vol. 273, No. 21, (Jun. 7, 1995), pp. 1702–1703.

Hopkin, "MTS1, Telomerase May be New Targets for Cancer Therapy", *The Journal of NIH Research*, vol. 6, (Jun. 1994), pp. 38–42.

Norris et al., "Identification of a New Subclass of Alu DNA Repeats Which Function as Estrogen Receptor–Dependent Transcriptional Enhancers", *Journal of Biological Chemistry*, vol. 270, No. 39, (Sep. 29, 1995), pp. 22777–22782.

Davis et al., "$S_1$ Nuclease Protection Assay", *Basic Methods in Molecular Biology*, (1986), pp. 276–284.

Futreal et al., "BRCA1 Mutations in Primary Breast and Ovarian Carcinomas", *Science*, vol. 266, (Oct. 7, 1994), pp. 120–122.

Holt et al., "Histopathology: Old Principles and New Methods", *Cancer Surveys*, vol. 18, (1993), pp. 1–24.

Liang et al., "Differential Display and Cloning of a Messenger RNAs from Human Breast Cancer versus Mammary Epithelial Cells", *Cancer Research*, vol. 52, (Dec. 15, 1992), pp. 6966–6968.

Campbell et al., "A Novel Gene Encoding a B–Box Protein Within the BRCA1 Region at 17q21.1", *Human Molecular Genetics*, vol. 3, No. 4, (1994), pp. 589–594.

Narod et al., "An Evaluation of Genetic Heterogeneity in 145 Breast–Ovarian Cancer Families", *Am. J. Hum. Genet.*, vol. 56, (1995), pp. 254–264.

Marcus et al., "Pathology and Heredity of Breast Cancer in Younger Women", *Journal of the National Cancer Institute Monographs*, No. 16, (1994), pp. 23–33.

Porter et al., "Breast Cancer Incidence, Penetrance and Survival in Probable Carriers of BRCA1 Gene Mutations in Families Linked to BRCA1 on Chromosome 17q12–21", *British Journal of Surgery*, vol. 81, (1994), pp. 1512–1515.

Merlo et al., "Evidence for a Second Tumor Suppressor Gene on 17p Linked to High S–Phase Index in Primary Human Breast Carcinomas", *Cancer Genet. Cytogenet.*, vol. 76, (1994), pp. 106–111.

Neuhausen et al., "Loss of Heterozygosity in Familial Tumors from Three BRCA1–Linked Kindreds", *Cancer Research*, vol. 54, (Dec. 1, 1994), pp. 6069–6072.

Brown et al., "Regulation of BRCA1", *Nature*, vol. 372, (Dec. 22/29 1994), p. 733.

Simard et al., "Common Origins of BRCA1 Mutations in Canadian Breast and Ovarian Cancer Families", *Nature Genetics*, vol. 8, (Dec. 1994).

Castilla et al., "Mutations in the BRCA1 Gene in Families with Early–Onset Breast and Ovarian Cancer", *Nature Genetics*, vol. 8, (Dec. 1994), pp. 387–391.

Friedman et al., "Confirmation of BRCA1 by Analysis of Germline Mutations Linked to Breast and Ovarian Cancer in Ten Families", *Nature Genetics*, pp. 1–6.

Güzburg et al., "Virus Vector Design in Gene Therapy", *Molecular Medicine Today*, (1995), pp. 410–417.

Reeck et al., "'Homology' in Proteins and Nucleic Acids: A Terminology Muddle and a Way Out of It", *Cell.*, vol. 59(Aug. 28, 1987), p. 667.

Ledley, "Nonviral Gene Therapy: The Promise of Genes as Pharmaceutical Products", *Human Gene Therapy*, vol. 6, (Sep. 1995), pp. 1129–1144.

Marshall, "Less Hype, More Biology Needed for Gene Therapy", *Science*, (Dec. 1995), p. 1751.

Coghlan, "Gene Dream Fades Away", *New Scientist*, (Nov. 1995).

Jain, "Barriers to Drug Delivery in Solid Tumors", *Scientific American*, (Jul. 1994), pp. 58–65.

Mastrangelo et al., "Gene Therapy for Human Cancer: An Essay for Clinicians", *Seminars in Oncology*, vol. 23, No. 1, (Feb. 1996), pp. 4–21.

Wallace et al., "Oligonucleotide Probes for the Screening of Recombinant DNA Libraries", *Methods in Enzymology*, vol. 152, (1987), pp. 432–443.

Sambrook et al., "Estimating the Effects of Mismatches", *Molecular Cloning*, (1989), CSH 11.47.

(Abstract only) Neuhold et al., "Dioxin–inducible Enhancer Region Upstream from the Mouse P–1450 Gene and Interaction with a Heterologous SV–40 Promoter", *DNA*, vol. 5 (1986), pp. 403–412.

Langston et al. "BRCA1 Mutations in a Population–Based Sample of Young Women with Breast Cancer", *The New England Journal of Medicine*, vol. 334, No. 3, pp. 137–142.

Bieche et al. "Genetic Alterations in Breast Cancer", *Genes, Chromosomes & Cancer*, vol. 14 (1995), pp. 227–251.

Figure 1: BRCA1 Antigens

C-19 (19 C-terminal amino acids): [Seq ID No: 5]
    Tyr Gln Cys Gln Glu Leu Asp Thr Tyr Leu Ile Pro Gln Ile Pro His Ser His Tyr C-20 (20 C-terminal amino acids): [Seq ID No: 6]
    Leu Tyr Gln Cys Gln Glu Leu Asp Thr Tyr Leu Ile Pro Gln Ile Pro His Ser His Tyr D-20 ( 20 N-terminal amino acids): [Seq ID No: 7]
    Met Asp Leu Ser Ala Leu Arg Val Glu Glu Val Gln Asn Val Ile Asn Ala Met Gln Lys

FIG. 1

Table of the Genetic Code

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

FIG. 2

Granin Sequences SEQ ID NOS: 8 - 29

| Granin | Species | Amino Acid | | | | | | | | |
|---|---|---|---|---|---|---|---|---|---|---|
| Consensus | | E<br>D | N<br>S | L | S<br>A<br>N | X | X | D<br>E | X | E<br>D | L |
| BRCA1 | Human | E | N | L | S | S | E | D | E | E | L |
| | Rhesus | E | N | L | S | S | E | D | E | E | L |
| | Mouse | E | S | D | S | T | E | D | E | D | L |
| BRCA2 | Human | E | S | N | S | I | A | D | E | E | L |
| Chromogranin A | Human | E | S | L | S | A | I | E | A | E | L |
| | Bovine | E | S | L | S | A | I | E | A | E | L |
| | Rat | E | S | L | S | A | I | E | A | E | L |
| | Pig | E | S | L | S | A | I | E | A | E | L |
| Chromogranin B | Human | E | N | L | A | A | M | D | L | E | L |
| | Bovine | E | N | L | A | A | M | D | L | E | L |
| | Mouse | E | N | L | A | A | M | D | L | E | L |
| Secretogranin II | Human | E | N | L | N | D | K | D | Q | E | L |
| | Bovine | E | N | L | N | D | K | D | Q | E | L |
| | Rat | D | N | L | N | D | K | D | Q | E | L |
| | Mouse | E | N | L | N | - | - | D | Q | E | L |
| Secretogranin III | Rat | E | N | L | D | E | T | I | A | L | Q |
| | Mouse | E | N | L | D | E | T | I | A | L | Q |
| Secretogranin V | Human | G | N | I | P | N | I | V | A | E | L |
| | Pig | G | N | I | P | N | I | V | A | E | L |
| | Rat | G | N | I | P | N | I | V | A | E | L |
| | Xenopus | G | N | I | P | N | I | V | A | E | L |
| Frequency of consensus amino acid in complete BRCA1 sequence | | 0.15 | 0.19 | 0.08 | 0.23 | 1 | 1 | 0.15 | 1 | 0.15 | 0.08 |

FIG. 5

Table I Effect of BRCA1 Expression Vectors on Growth

| Vector | Fibroblast | MCF-7 | CaOV-4 | Lung Ca | Colon Ca |
|---|---|---|---|---|---|
| LXSN | 85+2.5 | 85+3.7 | 72+2.3 | 98+1.7 | 433+9.4 |
| BRCA1 | 87+2.2 | 0+0* | 0+0* | 101+4.2 | 480+16.3 |
| Δ343-1081 | 84+1.4 | 96+3.7 | 76+4.9 | 97+3.7 | 460+29.4 |
| Δ515-1092 | 88+2.4 | 93+15.9 | 77+4.2 | 99+5.0 | 473+28.7 |
| 1835 Stop | 85+1.2 | 88+3.3 | 3+1.7 | 102+5.8 | 473+20.5 |
| 340 Stop | 87+1.4 | 89+3.3 | 80+2.7 | 99+5.0 | 483+33.0 |

G418-resistant transfectants per 10⁷ cells, Mean + Standard Error
Lung cancer cells = FK111; colon cancer cells = OK3;
Breast cancer cell line = MCF-7; Ovarian cancer cell line = CaOV-4
* 10-20 small colonies were identified in each transfection but these never grew beyond 30 cells per clone.

FIG. 6

Table II. Inherited BRCA1 mutation and type of cancer

| Termination codon of mutant protein | Cancer site | |
|---|---|---|
| | Breast | Ovary |
| 0a | 16 | 3 |
| 36 | 2 | |
| 37 | 7 | 1 |
| 39 | 17 | 9 |
| 64 | 6 | 4 |
| 81 | 4 | 2 |
| 313 | 5 | 1 |
| 766 | 3 | 4 |
| 780 | 7 | |
| 901 | 14 | 4 |
| 915 | 4 | 3 |
| 123 | 6 | |
| 1214-1223 | Granin motif | |
| 1265 | 5 | |
| 1364 | 12 | 1 |
| 1829 | 6 | |
| 1853 | 7 | |
| 1863b | 13 | |
| | | |
| 0-1223 | 91 | 31  25% |
| 1223-1863 | 43 | 1  2% | a Nonsense mutations leading to loss of transcript
b Complete problem: missense mutations in RING finger

FIG. 7

Table III. Inhibition of Tumorigenesis by BRCA1

| Vector | MCF-7 (4wks) | MCF-7 (8wks) | Weight of MCF Tumor | MCF-7 stables | Established tumors | Colon Tumors* |
|---|---|---|---|---|---|---|
| None | 6/6 | 6/6* | Not done | Not done | Not done | 5/6 |
| BRCA1 | 0/6 | 4/6* | 60g+24 | 0/20 | 24.4+2.1# | 6/6 |
| Δ343-1081 | 5/6 | 6/6* | 569g+60 | 13/15 | 8.6+1.3# | 6/6 |

The columns headed MCF-7 (4wks) and (8wks) and colon tumors are results following retroviral transduction of cultured cells. The assay for inhibition of established tumor growth was whether the retrovirus could delay survival for an additional 14 days. The column labeled MCF-7 stables shows tumor development of cloned BRCA1 and mutant cell lines. MCF-7 stables are results of stable transformants.
*colon tumor weights: BRCA1=1540+128; Δ343-1081=1633+110
mean+SE of post injection survivals (days): BRCA1=15,18,22,26,41
    Δ343-1081=4,8,9,11,11

FIG. 8

Gene sequence for BRCA1 [SEQ ID NO: 1]
(reference Miki et al. Science 266:66, 1994)

agctcgctgagacttcctggaccccgcaccaggctgtggggtttctcagataactgggcccctgcgctca ggaggccttcaccctctgctctgggtaaagttcattggaacagaaagaaatggatttatctgctcttcgcgt tgaagaagtacaaaatgtcattaatgctatgcagaaaatcttagagtgtcccatctgtctggagttgatcaa ggaacctgtctccacaaagtgtgaccacatattttgcaaattttgcatgctgaaacttctcaaccagaagaa agggccttcacagtgtcctttatgtaagaatgatataaccaaaaggagcctacaagaaagtacgagattta gtcaacttgttgaagagctattgaaaatcatttgtgcttttcagcttgacacaggtttggagtatgcaaacag ctataattttgcaaaaaaggaaaataactctcctgaacatctaaaagatgaagtttctatcatccaaagtatg ggctacagaaaccgtgccaaaagacttctacagagtgaacccgaaaatccttccttgcaggaaaccagtc tcagtgtccaactctctaaccttggaactgtgagaactctgaggacaaagcagcggatacaacctcaaaa gacgtctgtctacattgaattgggatctgattcttctgaagataccgttaataaggcaacttattgcagtgtg ggagatcaagaattgttacaaatcacccctcaaggaaccagggatgaaatcagtttggattctgcaaaaa aggctgcttgtgaattttctgagacggatgtaacaaatactgaacatcatcaacccagtaataatgatttgaa caccactgagaagcgtgcagctgagaggcatccagaaaagtatcagggtagttctgtttcaaacttgcat gtggagccatgtggcacaaatactcatgccagctcattacagcatgagaacagcagtttattactcactaa agacagaatgaatgtagaaaaggctgaattctgtaataaaagcaaacagcctggcttagcaaggagcca acataacagatgggctggaagtaaggaaacatgtaatgataggcggactcccagcacagaaaaaaagg tagatctgaatgctgatcccctgtgtgagagaaaagaatggaataagcagaaactgccatgctcagagaa tcctagagatactgaagatgttccttggataacactaaatagcagcattcagaaagttaatgagtggttttcc agaagtgatgaactgttaggttctgatgactcacatgatggggagtctgaatcaaatgccaaagtagctga tgtattggacgttctaaatgaggtagatgaatattctggttcttcagagaaaatagacttactggccagtgat cctcatgaggctttaatatgtaaaagtgaaagagttcactccaaatcagtagagagtaatattgaagacaaa atatttgggaaaacctatcggaagaaggcaagcctccccaacttaagccatgtaactgaaaatctaattata

FIG. 9A ggagcatttgttactgagccacagataatacaagagcgtccccctcacaaataaattaaagcgtaaaagga
gacctacatcaggccttcatcctgaggattttatcaagaaagcagatttggcagttcaaaagactcctgaaa
tgataaatcagggaactaaccaaacggagcagaatggtcaagtgatgaatattactaatagtggtcatga
gaataaaacaaaaggtgattctattcagaatgagaaaaatcctaacccaatagaatcactcgaaaaagaat
ctgctttcaaaacgaaagctgaacctataagcagcagtataagcaatatggaactcgaattaaatatccac
aattcaaaagcacctaaaaagaataggctgaggaggaagtcttctaccaggcatattcatgcgcttgaact
agtagtcagtagaaatctaagcccacctaattgtactgaattgcaaattgatagttgttctagcagtgaaga
gataaagaaaaaaagtacaaccaaatgccagtcaggcacagcagaaacctacaactcatggaaggta
aagaacctgcaactggagccaagaagagtaacaagccaaatgaacagacaagtaaaagacatgacag
cgatactttcccagagctgaagttaacaaatgcacctggttcttttactaagtgttcaaataccagtgaactta
aagaatttgtcaatcctagccttccaagagaagaaaaagaagagaaactagaaacagttaaagtgtctaat
aatgctgaagaccccaaagatctcatgttaagtggagaaagggttttgcaaactgaaagatctgtagaga
gtagcagtatttcattggtacctggtactgattatggcactcaggaaagtatctcgttactggaagttagcac
tctagggaaggcaaaaacagaaccaaataaatgtgtgagtcagtgtgcagcatttgaaaaccccaaggg
actaattcatggttgttccaaagataatagaaatgacacagaaggctttaagtatccattgggacatgaagt
taaccacagtcgggaaacaagcatagaaatggaagaaagtgaacttgatgctcagtatttgcagaataca
ttcaaggtttcaaagcgccagtcatttgctccgttttcaaatccaggaaatgcagaagaggaatgtgcaac
attctctgcccactctgggtccttaaagaaacaaagtccaaaagtcacttttgaatgtgaacaaaaggaag
aaaatcaaggaaagaatgagtctaatatcaagcctgtacagacagttaatatcactgcaggctttcctgtg
gttggtcagaaagataagccagttgataatgccaaatgtagtatcaaaggaggctctaggttttgtctatca
tctcagttcagaggcaacgaaactggactcattactccaaataaacatggacttttacaaaacccatatcgt
ataccaccacttttttcccatcaagtcatttgttaaaactaaatgtaagaaaaatctgctagaggaaaactttga
ggaacattcaatgtcacctgaaagagaaatgggaaatgagaacattccaagtacagtgagcacaattagc
cgtaataacattagagaaaatgttttaaagaagccagctcaagcaatattaatgaagtaggttccagtact
aatgaagtgggctccagtattaatgaaataggttccagtgatgaaaacattcaagcagaactaggtagaa

FIG. 9B acagagggccaaaattgaatgctatgcttagattaggggttttgcaacctgaggtctataaacaaagtcttc
ctggaagtaattgtaagcatcctgaaataaaaaagcaagaatatgaagaagtagttcagactgttaataca
gatttctctccatatctgatttcagataacttagaacagcctatgggaagtagtcatgcatctcaggtttgttct
gagacacctgatgacctgttagatgatggtgaaataaaggaagatactagttttgctgaaaatgacattaa
ggaaagttctgctgttttagcaaaagcgtccagaaaggagagcttagcaggagtcctagccctttcaccc
atacacatttggctcagggttaccgaagaggggccaagaaattagagtcctcagaagagaacttatctag
tgaggatgaagagcttccctgcttccaacacttgttatttggtaaagtaaacaatataccttctcagtctacta
ggcatagcaccgttgctaccgagtgtctgtctaagaacacagaggagaatttattatcattgaagaatagc
ttaaatgactgcagtaaccaggtaatattggcaaaggcatctcaggaacatcaccttagtgaggaaacaa
aatgttctgctagcttgttttcttcacagtgcagtgaattggaagacttgactgcaaatacaaacacccagg
atcctttcttgattggttcttccaaacaaatgaggcatcagtctgaaagccagggagttggtctgagtgaca
aggaattggtttcagatgatgaagaaagaggaacgggcttggaagaaaataatcaagaagagcaaagc
atggattcaaacttaggtgaagcagcatctgggtgtgagagtgaaacaagcgtctctgaagactgctcag
ggctatcctctcagagtgacattttaaccactcagcagagggataccatgcaacataacctgataaagctc
cagcaggaaatggctgaactagaagctgtgttagaacagcatgggagccagccttctaacagctacccttt
ccatcataagtgactcttctgcccttgaggacctgcgaaatccagaacaaagcacatcagaaaaagcagt
attaacttcacagaaaagtagtgaatacccctataagccagaatccagaaggcctttctgctgacaagtttga
ggtgtctgcagatagttctaccagtaaaaataaagaaccaggagtggaaaggtcatccccttctaaatgcc
catcattagatgataggtggtacatgcacagttgctctgggagtcttcagaatagaaactacccatctcaag
aggagctcattaaggttgttgatgtggaggagcaacagctggaagagtctgggccacacgatttgacgg
aaacatcttacttgccaaggcaagatctagagggaaccccttacctggaatctggaatcagcctcttctctg
atgaccctgaatctgatccttctgaagacagagccccagagtcagctcgtgttggcaacataccatcttca
acctctgcattgaaagttccccaattgaaagttgcagaatctgcccagagtccagctgctgctcatactact
gatactgctgggtataatgcaatggaagaaagtgtgagcagggagaagccagaattgacagcttcaaca
gaaagggtcaacaaaagaatgtccatggtggtgtctggcctgaccccagaagaatttatgctcgtgtaca

FIG. 9C agtttgccagaaaacaccacatcactttaactaatctaattactgaagagactactcatgttgttatgaaaac
agatgctgagtttgtgtgtgaacggacactgaaatattttctaggaattgcgggaggaaaatgggtagtta
gctatttctgggtgacccagtctattaaagaaagaaaaatgctgaatgagcatgattttgaagtcagagga
gatgtggtcaatggaagaaaccaccaaggtccaaagcgagcaagagaatcccaggacagaaagatctt
caggggggctagaaatctgttgctatgggcccttcaccaacatgcccacagatcaactggaatggatggta
cagctgtgtggtgcttctgtggtgaaggagctttcatcattcacccttggcacaggtgtccacccaattgtg
gttgtgcagccagatgcctggacagaggacaatggcttccatgcaattgggcagatgtgtgaggcacct
gtggtgacccgagagtgggtgttggacagtgtagcactctaccagtgccaggagctggacacctacctg
atacccagatcccccacagccactactgat

FIG. 9D

Sequence of the BRCA2 cDNA [SEQ ID NO: 3]

ggtggcgcgagcttctgaaactaggcggcagaggcggagccgctgtggcactgctgcgcctctgctgcgcc tcgggtgtcttttgcggcggtgggtcgccgccgggagaagcgtgaggggacagatttgtgaccggcgcggt ttttgtcagcttactccggccaaaaaagaactgcacctctggagcggacttatttaccaagcattggaggaatatc gtaggtaaaaatgcctattggatccaaagagaggccaacatttttgaaattttaagacacgctgcaacaaagc agatttaggaccaataagtcttaattggtttgaagaactttcttcagaagctccaccctataattctgaacctgcag aagaatctgaacataaaaacaacaattacgaaccaaacctatttaaaactccacaaaggaaaccatcttataatca gctggcttcaactccaataatattcaaagagcaagggctgactctgccgctgtaccaatctcctgtaaaagaatta gataaattcaaattagacttaggaaggaatgttcccaatagtagacataaaagtcttcgcacagtgaaaactaaa atggatcaagcagatgatgtttcctgtccacttctaaattcttgtcttagtgaaagtcctgttgttctacaatgtacac atgtaacaccacaaagagataagtcagtggtatgtgggagtttgtttcatacaccaaagtttgtgaagggtcgtc agacaccaaaacatatttctgaaagtctaggagctgaggtggatcctgatatgtcttggtcaagttctttagctac accacccacccttagttctactgtgctcatagtcagaaatgaagaagcatctgaaactgtatttcctcatgatacta ctgctaatgtgaaaagctattttccaatcatgatgaaagtctgaagaaaaatgatagatttatcgcttctgtgaca gacagtgaaaacacaaatcaaagagaagctgcaagtcatggatttggaaaaacatcagggaattcatttaaagt aaatagctgcaaagaccacattggaaagtcaatgccaaatgtcctagaagatgaagtatatgaaacagttgtag atacctctgaagaagatagttttttcattatgtttttctaaatgtagaacaaaaaatctacaaaaagtaagaactagca agactaggaaaaaaattttccatgaagcaaacgctgatgaatgtgaaaaatctaaaaaccaagtgaaagaaaaa tactcatttgtatctgaagtggaaccaaatgatactgatccattagattcaaatgtagcacatcagaagcccttga gagtggaagtgacaaaatctccaaggaagttgtaccgtctttggcctgtgaatggtctcaactaaccctttcagg tctaaatggagcccagatggagaaaataccccctattgcatatttcttcatgtgaccaaaatatttcagaaaaagac ctattagacacagagaacaaaagaaagaaagatttcttacttcagagaattctttgccacgtatttctagcctacc aaaatcagagaagccattaaatgaggaaacagtggtaaataagagagatgaagagcagcatcttgaatctcat acagactgcattcttgcagtaaagcaggcaatatctggaacttctccagtggcttcttcatttcagggtatcaaaa agtctatattcagaataagagaatcacctaaagagactttcaatgcaagttttttcaggtcatatgactgatccaaac

FIG. 10A tttaaaaaagaaactgaagcctctgaaagtggactggaaatacatactgtttgctcacagaaggaggactcctta
tgtccaaatttaattgataatggaagctggccagccaccaccacacagaattctgtagctttgaagaatgcaggtt
taatatccactttgaaaaagaaaacaaataagtttatttatgctatacatgatgaaacattttataaaggaaaaaaaa
taccgaaagaccaaaaatcagaactaattaactgttcagcccagtttgaagcaaatgcttttgaagcaccacttac
atttgcaaatgctgattcaggtttattgcattcttctgtgaaaagaagctgttcacagaatgattctgaagaaccaa
ctttgtccttaactagctcttttgggacaattctgaggaaatgttctagaaatgaaacatgttctaataatacagtaat
ctctcaggatcttgattataaagaagcaaaatgtaataaggaaaaactacagttatttattaccccagaagctgatt
ctctgtcatgcctgcaggaaggacagtgtgaaaatgatccaaaaagcaaaaaagtttcagatataaaagaaga
ggtcttggctgcagcatgtcacccagtacaacattcaaaagtggaatacagtgatactgactttcaatcccagaa
aagtctttatatgatcatgaaaatgccagcactcttattttaactcctacttccaaggatgttctgtcaaacctagtc
atgatttctagaggcaaagaatcatacaaaatgtcagacaagctcaaaggtaacaattatgaatctgatgttgaat
taaccaaaaatattcccatggaaaagaatcaagatgtatgtgctttaaatgaaaattataaaaacgttgagctgttg
ccacctgaaaaatacatgagagtagcatcaccttcaagaaaggtacaattcaaccaaaacacaaatctaagagt
aatccaaaaaaatcaagaagaaactacttcaatttcaaaaataactgtcaatccagactctgaagaacttttctcag
acaatgagaataattttgtcttccaagtagctaatgaaaggaataatcttgctttaggaaatactaaggaacttcat
gaaacagacttgacttgtgtaaacgaacccattttcaagaactctaccatggttttatatggagacacaggtgata
aacaagcaacccaagtgtcaattaaaaaagatttggtttatgttcttgcagaggagaacaaaaatagtgtaaagc
agcatataaaaatgactctaggtcaagatttaaaatcggacatctccttgaatatagataaaataccagaaaaaaa
taatgattacatgaacaaatgggcaggactcttaggtccaatttcaaatcacagttttggaggtagcttcagaaca
gcttcaaataaggaaatcaagctctctgaacataacattaagaagagcaaaatgttcttcaaagatattgaagaac
aatatcctactagtttagcttgtgttgaaattgtaaataccttggcattagataatcaaaagaaactgagcaagcct
cagtcaattaatactgtatctgcacatttacagagtagtgtagttgtttctgattgtaaaaatagtcatataacccctc
agatgttattttccaagcaggattttaattcaaaccataatttaacacctagccaaaaggcagaaattacagaacttt
ctactatattagaagaatcaggaagtcagtttgaatttactcagtttagaaaaccaagctacatattgcagaagagt
acatttgaagtgcctgaaaaccagatgactatcttaaagaccacttctgaggaatgcagagatgctgatcttcatg
tcataatgaatgccccatcgattggtcaggtagacagcagcaagcaatttgaaggtacagttgaaattaaacgg
aagtttgctggcctgttgaaaaatgactgtaacaaaagtgcttctggttatttaacagatgaaaatgaagtgggt

FIG. 10B ttaggggcttttattctgctcatggcacaaaactgaatgtttctactgaagctctgcaaaaagctgtgaaactgttta
gtgatattgagaatattagtgaggaaacttctgcagaggtacatccaataagtttatcttcaagtaaatgtcatgatt
ctgttgtttcaatgtttaagatagaaaatcataatgataaaactgtaagtgaaaaaaataataaatgccaactgatat
tacaaaataatattgaaatgactactggcacttttgttgaagaaattactgaaaattacaagagaaatactgaaaat
gaagataacaaatatactgctgccagtagaaattctcataacttagaatttgatggcagtgattcaagtaaaaatg
atactgtttgtattcataaagatgaaacggacttgctatttactgatcagcacaacatatgtcttaaattatctggcca
gtttatgaaggagggaaacactcagattaaagaagatttgtcagatttaacttttttggaagttgcgaaagctcaa
gaagcatgtcatggtaatacttcaaataaagaacagttaactgctactaaaacggagcaaaatataaaagattttg
agacttctgatacattttttcagactgcaagtgggaaaaatattagtgtcgccaaagagttatttaataaaattgtaa
atttctttgatcagaaaccagaagaattgcataacttttccttaaattctgaattacattctgacataagaaagaaca
aaatggacattctaagttatgaggaaacagacatagttaaacacaaaatactgaaagaaagtgtcccagttggta
ctggaaatcaactagtgaccttccagggacaacccgaacgtgatgaaagatcaaagaacctactctgttgggt
tttcatacagctagcggaaaaaaagttaaaattgcaaaggaatctttggacaaagtgaaaaacctttttgatgaaa
aagagcaaggtactagtgaaatcaccagttttagccatcaatgggcaaagaccctaaagtacagagaggcctg
taaagaccttgaattagcatgtgagaccattgagatcacagctgccccaaagtgtaaagaaatgcagaattctct
caataatgataaaaaccttgtttctattgagactgtggtgccacctaagctcttaagtgataatttatgtagacaaac
tgaaaatctcaaaacatcaaaaagtatcttttgaaagttaaagtacatgaaaatgtagaaaaagaaacagcaaaa
agtcctgcaacttgttacacaaatcagtccccttattcagtcattgaaaattcagccttagcttttacacaagttgta
gtagaaaaacttctgtgagtcagacttcattacttgaagcaaaaaaatggcttagagaaggaatatttgatggtca
accagaaagaataaatactgcagattatgtaggaaattatttgtatgaaaataattcaaacagtactatagctgaaa
atgacaaaaatcatctctccgaaaaacaagatacttatttaagtaacagtagcatgtctaacagctattcctaccatt
ctgatgaggtatataatgattcaggatatctctcaaaaaataaacttgattctggtattgagccagtattgaagaat
gttgaagatcaaaaaaacactagttttccaaagtaatatccaatgtaaaagatgcaaatgcatacccacaaactg
taaatgaagatatttgcgttgaggaacttgtgactagctcttcaccctgcaaaaataaaaatgcagccattaaattg
tccatatctaatagtaataattttgaggtagggccacctgcatttaggatagccagtggtaaaatccgtttgtgttc
acatgaaacaattaaaaaagtgaaagacatatttacagacagtttcagcaaagtaattaaggaaaacaacgaga
ataaatcaaaaatttgccaaacgaaaattatggcaggttgttacgaggcattggatgattcagaggatattcttcat aactctctagataatgatgaatgtagcatgcattcacataaggttttgctgacattcagagtgaagaaattttacaa
cataaccaaaatatgtctggattggagaaagtttctaaaatatcaccttgtgatgttagtttggaaacttcagatata
tgtaaatgtagtatagggaagcttcataagtcagtctcatctgcaaatacttgtgggattttagcacagcaagtg
gaaaatctgtccaggtatcagatgcttcattacaaaacgcaagacaagtgttttctgaaatagaagatagtaccaa
gcaagtcttttccaaagtattgtttaaaagtaacgaacattcagaccagctcacaagagaagaaaatactgctata
cgtactccagaacatttaatatcccaaaaaggcttttcatataatgtggtaaattcatctgctttctctggatttagta
cagcaagtggaaagcaagtttccatttagaaagttccttacacaaagttaagggagtgttagaggaatttgattt
aatcagaactgagcatagtcttcactattcacctacgtctagacaaaatgtatcaaaaatacttcctcgtgttgataa
gagaaacccagagcactgtgtaaactcagaaatggaaaaaacctgcagtaaagaatttaaattatcaaataactt
aaatgttgaaggtggttcttcagaaaataatcactctattaaagtttctccatatctctctcaatttcaacaagacaaa
caacagttggtattaggaaccaaagtctcacttgttgagaacattcatgttttgggaaaagaacaggcttcaccta
aaaacgtaaaaatggaaattggtaaaactgaaactttttctgatgttcctgtgaaaacaaatatagaagtttgttcta
cttactccaaagattcagaaaactactttgaaacagaagcagtagaaattgctaaagcttttatggaagatgatga
actgacagattctaaactgccaagtcatgccacacattctcttttacatgtcccgaaaatgaggaaatggttttgt
caaattcaagaattggaaaaagaagaggagagccccttatcttagtgggagaaccctcaatcaaaagaaactta
ttaaatgaatttgacaggataatagaaaatcaagaaaaatccttaaaggcttcaaaaagcactccagatggcaca
ataaaagatcgaagattgtttatgcatcatgtttctttagagccgattacctgtgtacccttcgcacaactaaggaa
cgtcaagagatacagaatccaaattttaccgcacctggtcaagaatttctgtctaaatctcatttgtatgaacatctg
actttggaaaaatcttcaagcaatttagcagtttcaggacatccattttatcaagtttctgctacaagaaatgaaaaa
atgagacacttgattactacaggcagaccaaccaaagtctttgttccacctttaaaactaaatcacattttcacag
agttgaacagtgtgttaggaatattaacttggaggaaaacagacaaaagcaaaacattgatggacatggctctg
atgatagtaaaaataagattaatgacaatgagattcatcagtttaacaaaaacaactccaatcaagcagcagctgt
aactttcacaaagtgtgaagaagaacctttagatttaattacaagtcttcagaatgccagagatatacaggatatg
cgaattaagaagaaacaaaggcaacgcgtctttccacagccaggcagtctgtatcttgcaaaaacatccactct
gcctcgaatctctctgaaagcagcagtaggaggccaagttccctctgcgtgttctcataaacagctgtatacgta
tggcgtttctaaacattgcataaaaattaacagcaaaaatgcagagtcttttcagtttcacactgaagattattttgg
taaggaaagtttatggactggaaaaggaatacagttggctgatggtggatggctcatacccctccaatgatggaa

FIG. 10D aggctggaaaagaagaattttataggggctctgtgtgacactccaggtgtggatccaaagcttatttctagaatttg
ggtttataatcactatagatggatcatatggaaactggcagctatggaatgtgcctttcctaaggaatttgctaata
gatgcctaagcccagaaagggtgcttcttcaactaaaatacagatatgatacggaaattgatagaagcagaaga
tcggctataaaaaagataatggaaagggatgacacagctgcaaaaacacttgttctctgtgtttctgacataattt
cattgagcgcaaatatatctgaaacttctagcaataaaactagtagtgcagatacccaaaaagtggccattattga
acttacagatgggtggtatgctgttaaggcccagttagatcctcccctcttagctgtcttaaagaatggcagactg
acagttggtcagaagattattcttcatggagcagaactggtgggctctcctgatgcctgtacacctcttgaagcc
ccagaatctcttatgttaaagatttctgctaacagtactcggcctgctcgctggtataccaaacttggattctttcct
gaccctagaccttttcctctgcccttatcatcgcttttcagtgatggaggaaatgttggttgtgttgatgtaattattc
aaagagcataccctatacagcggatggagaagacatcatctggattatacatatttcgcaatgaaagagaggaa
gaaaaggaagcagcaaaatatgtggaggcccaacaaaagagactagaagccttattcactaaaattcaggag
gaatttgaagaacatgaagaaaacacaacaaaaccatatttaccatcacgtgcactaacaagacagcaagttcg
tgctttgcaagatggtgcagagctttatgaagcagtgaagaatgcagcagacccagcttaccttgagggttattt
cagtgaagagcagttaagagccttgaataatcacaggcaaatgttgaatgataagaaacaagctcagatccagt
tggaaattaggaaggccatggaatctgctgaacaaaaggaacaaggtttatcaagggatgtcacaaccgtgtg
gaagttgcgtattgtaagctattcaaaaaaagaaaaagattcagttatactgagtatttggcgtccatcatcagatt
tatattctctgttaacagaaggaaagagatacagaatttatcatcttgcaacttcaaaatctaaaagtaaatctgaaa
gagctaacatacagttagcagcgacaaaaaaaactcagtatcaacaactaccggtttcagatgaaattttatttca
gatttaccagccacgggagccccttcacttcagcaaatttttagatccagactttcagccatcttgttctgaggtgg
acctaataggatttgtcgtttctgttgtgaaaaaaacaggacttgcccctttcgtctatttgtcagacgaatgttaca
atttactggcaataaagttttggatagaccttaatgaggacattattaagcctcatatgttaattgctgcaagcaacc
tccagtggcgaccagaatccaaatcaggccttcttactttatttgctggagattttctgtgttttctgctagtccaaa
agagggccactttcaagagacattcaacaaaatgaaaaatactgttgagaatattgacatactttgcaatgaagc
agaaaacaagcttatgcatatactgcatgcaaatgatcccaagtggtccaccccaactaaagactgtacttcagg
gccgtacactgctcaaatcattcctggtacaggaaacaagcttctgatgtcttctcctaattgtgagatatattatca
aagtcctttatcactttgtatggccaaaaggaagtctgtttccacacctgtctcagcccagatgacttcaaagtctt
gtaaaggggagaaagagattgatgaccaaaagaactgcaaaaagagaagagccttggatttcttgagtagact
</p>

FIG. 10E gcctttacctccacctgttagtcccatttgtacatttgtttctccggctgcacagaaggcatttcagccaccaagga
gttgtggcaccaaatacgaaacacccataaagaaaaaagaactgaattctcctcagatgactccatttaaaaaatt
caatgaaatttctcttttggaaagtaattcaatagctgacgaagaacttgcattgataaatacccaagctcttttgtct
ggttcaacaggagaaaaacaatttatatctgtcagtgaatccactaggactgctcccaccagttcagaagattatc
tcagactgaaacgacgttgtactacatctctgatcaaagaacaggagagttcccaggccagtacggaagaatgt
gagaaaaataagcaggacacaattacaactaaaaaatatatctaagcatttgcaaaggcgacaataaattattga
cgcttaacctttccagtttataagactggaatataatttcaaaccacacattagtacttatgttgccaatgagaaaag
aaattagtttcaaatttacctcagcgtttgtgtatcgggcaaaaatcgttttgcccgattccgtattggtatactttg
cctcagttgcatatcctaaaactaaatgtaatttattaactaatcaagaaaaacatctttggctgagctcggtggctc
atgcctgtaatcccaacactttgagaagctgaggtgggaggagtgcttgaggccaggagttcaagaccagcct
gggcaacatagggagaccccatctttacgaagaaaaaaaaaaggggaaaagaaaatcttttaaatctttggat
ttcactacaagtattattttacaagtgaaataaacataccattttcttttagattgtgtcattaaatggaatgaggtctc
ttagtacagttattttgatgcagataattcctttagtttagctactattttaggggatttttttagaggtaactcactat
gaaatagttccccttaatgcaaatatgttggttctgcaatagttccatcctgttcaaaatcggtgaaatgaagagtg
gtgttccttttgagcaattctcatccttaagtcagctgattataagaaaaatagaaccccagtgtaacctaattccttt
ttctattccagtgtgatctctgaaataaattacttcactaaaaattcaaaaacttaatcagaaattcaagtaatttatttt
ttttt
```

FIG. 10F

BRCA2 Protein sequence [SEQ ID NO: 4]

MPIGSKERPTFFEIFKTRCNKADLGPISLNWFEELSSEAPPYNSEPAEE
SEHKNNNYEPNLFKTPQRKPSYNQLASTPIIFKEQGLTLPLYQSPVKE
LDKFKLDLGRNVPNSRHKSLRTVKTKMDQADDVSCPLLNSCLSESPV
VLQCTHVTPQRDKSVVCGSLFHTPKFVKGRQTPKHISESLGAEVDPD
MSWSSSLATPPTLSSTVLIVRNEEASETVFPHDTTANVKSYFSNHDES
LKKNDRFIASVTDSENTNQREAASHGFGKTSGNSFKVNSCKDHIGKS
MPNVLEDEVYETVVDTSEEDSFSLCFSKCRTKNLQKVRTSKTRKKIF
HEANADECEKSKNQVKEKYSFVSEVEPNDTDPLDSNVAHQKPFESGS
DKISKEVVPSLACEWSQLTLSGLNGAQMEKIPLLHISSCDQNISEKDL
LDTENKRKKDFLTSENSLPRISSLPKSEKPLNEETVVNKRDEEQHLES
HTDCILAVKQAISGTSPVASSFQGIKKSIFRIRESPKETFNASFSGHMTD
PNFKKETEASESGLEIHTVCSQKEDSLCPNLIDNGSWPATTTQNSVAL
KNAGLISTLKKKTNKFIYAIHDETFYKGKKIPKDQKSELINCSAQFEA
NAFEAPLTFANADSGLLHSSVKRSCSQNDSEEPTLSLTSSFGTILRKCS
RNETCSNNTVISQDLDYKEAKCNKEKLQLFITPEADSLSCLQEGQCE
NDPKSKKVSDIKEEVLAAACHPVQHSKVEYSDTDFQSQKSLLYDHEN
ASTLILTPTSKDVLSNLVMISRGKESYKMSDKLKGNNYESDVELTKNI
PMEKNQDVCALNENYKNVELLPPEKYMRVASPSRKVQFNQNTNLR
VIQKNQEETTSISKITVNPDSEELFSDNENNFVFQVANERNNLALGNT
KELHETDLTCVNEPIFKNSTMVLYGDTGDKQATQVSIKKDLVYVLA
EENKNSVKQHIKMTLGQDLKSDISLNIDKIPEKNNDYMNKWAGLLG
PISNHSFGGSFRTASNKEIKLSEHNIKKSKMFFKDIEEQYPTSLACVEIV
NTLALDNQKKLSKPQSINTVSAHLQSSVVVSDCKNSHITPQMLFSKQD
FNSNHNLTPSQKAEITELSTILEESGSQFEFTQFRKPSYILQKSTFEVPE

FIG. 11A

NQMTILKTTSEECRDADLHVIMNAPSIGQVDSSKQFEGTVEIKRKFAG
LLKNDCNKSASGYLTDENEVGFRGFYSAHGTKLNVSTEALQKAVKL
FSDIENISEETSAEVHPISLSSSKCHDSVVSMFKIENHNDKTVSEKNNKC
QLILQNNIEMTTGTFVEEITENYKRNTENEDNKYTAASRNSHNLEFD
GSDSSKNDTVCIHKDETDLLFTDQHNICLKLSGQFMKEGNTQIKEDLS
DLTFLEVAKAQEACHGNTSNKEQLTATKTEQNIKDFETSDTFFQTAS
GKNISVAKELFNKIVNFFDQKPEELHNFSLNSELHSDIRKNKMDILSY
EETDIVKHKILKESVPVGTGNQLVTFQGQPERDEKIKEPTLLGFHTAS
GKKVKIAKESLDKVKNLFDEKEQGTSEITSFSHQWAKTLKYREACK
DLELACETIEITAAPKCKEMQNSLNNDKNLVSIETVVPPKLLSDNLC
RQTENLKTSKSIFLKVKVHENVEKETAKSPATCYTNQSPYSVIENSAL
AFYTSCSRKTSVSQTSLLEAKKWLREGIFDGQPERINTADYVGNYLY
ENNSNSTIAENDKNHLSEKQDTYLSNSSMSNSYSYHSDEVYNDSGYLS
KNKLDSGIEPVLKNVEDQKNTSFSKVISNVKDANAYPQTVNEDICVE
ELVTSSSPCKNKNAAIKLSISNSNNFEVGPPAFRIASGKIRLCSHETIKK
VKDIFTDSFSKVIKENNENKSKICQTKIMAGCYEALDDSEDILHNSLD
NDECSMHSHKVFADIQSEEILQHNQNMSGLEKVSKISPCDVSLETSDIC
KCSIGKLHKSVSSANTCGIFSTASGKSVQVSDASLQNARQVFSEIEDST
KQVFSKVLFKSNEHSDQLTREENTAIRTPEHLISQKGFSYNVVNSSAFS
GFSTASGKQVSILESSLHKVKGVLEEFDLIRTEHSLHYSPTSRQNVSKI
LPRVDKRNPEHCVNSEMEKTCSKEFKLSNNLNVEGGSSENNHSIKVSP
YLSQFQQDKQQLVLGTKVSLVENIHVLGKEQASPKNVKMEIGKTET
FSDVPVKTNIEVCSTYSKDSENYFETEAVEIAKAFMEDDELTDSKLPS
HATHSLFTCPENEEMVLSNSRIGKRRGEPLILVGEPSIKRNLLNEFDRI
IENQEKSLKASKSTPDGTIKDRRLFMHHVSLEPITCVPFRTTKERQEIQ
NPNFTAPGQEFLSKSHLYEHLTLEKSSSNLAVSGHPFYQVSATRNEK

FIG. 11B

MRHLITTGRPTKVFVPPFKTKSHFHRVEQCVRNINLEENRQKQNIDG
HGSDDSKNKINDNEIHQFNKNNSNQAAAVTFTKCEEEPLDLITSLQN
ARDIQDMRIKKKQRQRVFPQPGSLYLAKTSTLPRISLKAAVGGQVPS
ACSHKQLYTYGVSKHCIKINSKNAESFQFHTEDYFGKESLWTGKGIQ
LADGGWLIPSNDGKAGKEEFYRALCDTPGVDPKLISRIWVYNHYRW
IIWKLAAMECAFPKEFANRCLSPERVLLQLKYRYDTEIDRSRRSAIKK
IMERDDTAAKTLVLCVSDIISLSANISETSSNKTSSADTQKVAIIELTD
GWYAVKAQLDPPLLAVLKNGRLTVGQKIILHGAELVGSPDACTPLE
APESLMLKISANSTRPARWYTKLGFFPDPRPFPLPLSSLFSDGGNVGC
VDVIIQRAYPIQRMEKTSSGLYIFRNEREEEKEAAKYVEAQQKRLEA
LFTKIQEEFEEHEENTTKPYLPSRALTRQQVRALQDGAELYEAVKN
AADPAYLEGYFSEEQLRALNNHRQMLNDKKQAQIQLEIRKAMESAE
QKEQGLSRDVTTVWKLRIVSYSKKEKDSVILSIWRPSSDLYSLLTEGK
RYRIYHLATSKSKSKSERANIQLAATKKTQYQQLPVSDEILFQIYQPR
EPLHFSKFLDPDFQPSCSEVDLIGFVVSVVKKTGLAPFVYLSDECYNL
LAIKFWIDLNEDIIKPHMLIAASNLQWRPESKSGLLTLFAGDFSVFSAS
PKEGHFQETFNKMKNTVENIDILCNEAENKLMHILHANDPKWSTPT
KDCTSGPYTAQIIPGTGNKLLMSSPNCEIYYQSPLSLCMAKRKSVSTP
VSAQMTSKSCKGEKEIDDQKNCKKRRALDFLSRLPLPPPVSPICTFVS
PAAQKAFQPPRSCGTKYETPIKKKELNSPQMTPFKKFNEISLLESNSIA
DEELALINTQALLSGSTGEKQFISVSESTRTAPTSSEDYLRLKRRCTTS
LIKEQESSQASTEECEKNKQDTITTKKYI

FIG. 11C

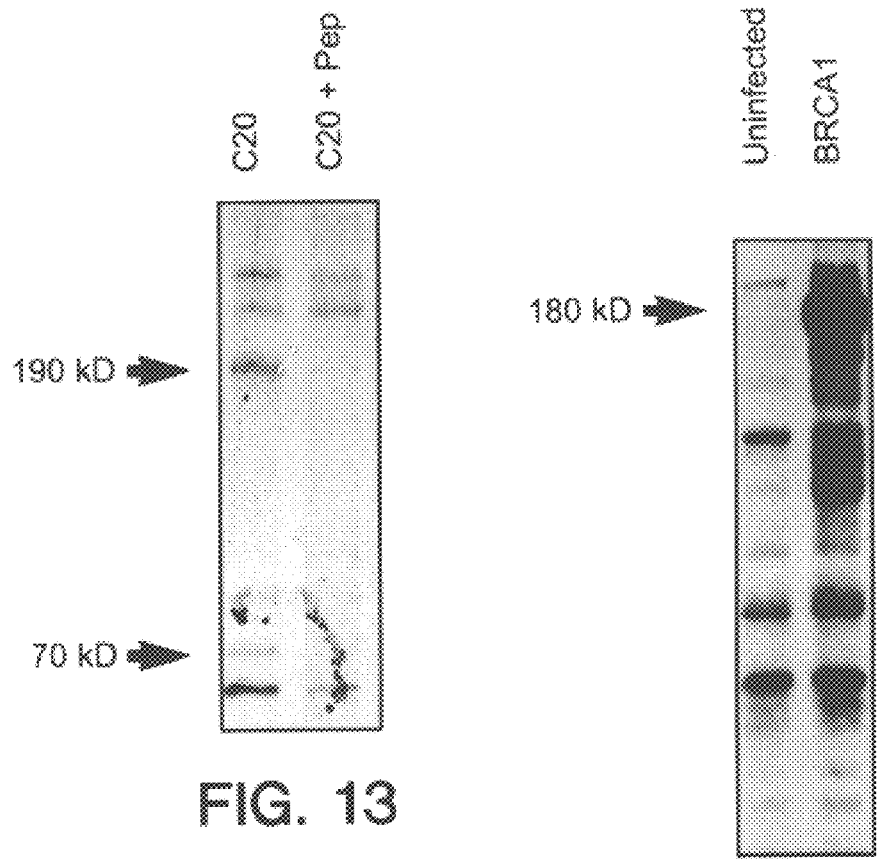
FIG. 13
FIG. 14
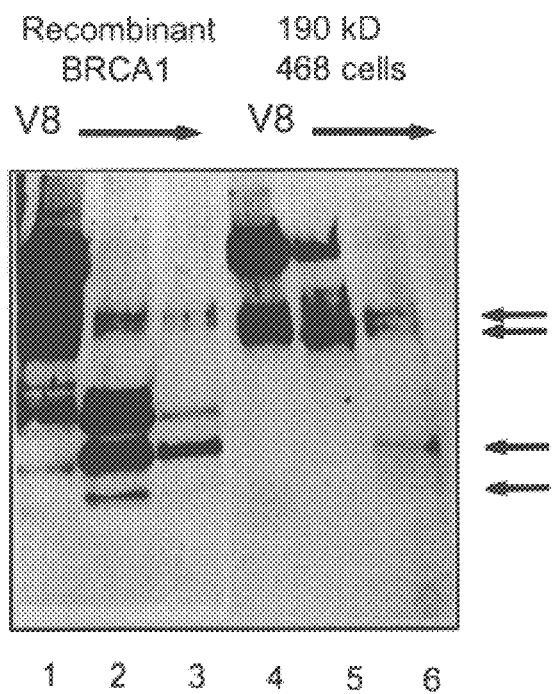
FIG. 15

CHARACTERIZED BRCA1 AND BRCA2 PROTEINS AND SCREENING AND THERAPEUTIC METHODS BASED ON CHARACTERIZED BRCA1 AND BRCA2 PROTEINS

CROSS REFERENCE TO RELATED APPLICATIONS

This is a continuation application of U.S. patent application Ser. No. 08/603,753, filed Feb. 20, 1996, now U.S. Pat. No. 5,891,857.

This invention was made in part from government support under Grant No. ES-00267 from the National Institutes of Health, National Institute of Environmental Health Sciences; and under Grants R29-CA62161, T32-CA09592, F32-CA66293 and R01-CA27632 from the National Institutes of Health. The government has certain rights in the invention.

UTILITY STATEMENT

Both the BRCA1 and BRCA2 proteins have been identified as inhibitors of the growth of breast and ovarian cancer cells and thus a DNA segment encoding the BRCA1 protein and a DNA segment encoding the BRCA2 protein can be used in a gene therapy methods for the treatment of breast cancer and for the treatment of ovarian cancer.

The discovery and purification of the BRCA1 protein has broad utility. The purified BRCA1 protein can be used in treating breast or ovarian cancer. Moreover, since it has been determined that the BRCA1 protein is secreted, the BRCA1 protein can be also be used to identify the BRCA1 receptor. Once the BRCA1 receptor is identified, BRCA1 protein-mimetic agents which act on the receptor can be identified. Such agents are also useful in the treatment of breast and ovarian cancer.

The BRCA2 protein is also a secreted protein and can be used to identify the BRCA2 receptor. Once the BRCA2 receptor is identified, BRCA2 protein-mimetic agents which act on the receptor can be identified. Such agents are also useful in the treatment of breast and ovarian cancer.

ACTIVITY STATEMENT

The BRCA1 gene product is an inhibitor of the growth and proliferation of human breast and ovarian cancer cells. The BRCA1 gene product is a secreted protein, thus indicating that it acts on a receptor to produce this activity.

The BRCA2 protein is an inhibitor of the growth and proliferation of human breast and ovarian cancer cells. The BRCA2 protein is a secreted protein, thus indicating that it acts on a receptor to produce this activity.

BACKGROUND OF THE INVENTION

The present invention relates generally to purified and isolated proteins and DNA molecules; to methods of screening for receptors; and to methods of treatment of ovarian and breast cancer, and more particularly to a purified and isolated BRCA1 protein cleavage products; and to gene therapy methods using the BRCA1 gene and the BRCA2 gene in the treatment of breast and ovarian cancer; and to methods for identifying the receptors of the BRCA1 protein and the BRCA2 protein.

The human breast and ovarian cancer susceptibility gene BRCA1 is mutated in the germline and lost in tumor tissue in hereditary breast and ovarian cancer (Hall et al., 1990, Science 250, 1684–1689; Miki et al., 1995 Science 266, 66–71; Smith et al., 1992; Cornelius et al., 1995, The Breast Cancer Linkage Consortium. Genes Chrom Cancer 13: 203–210).

Despite much excitement with the discovery of BRCA1, mutations were only found in the germline which accounts for only a small minority of breast cancers (Futreal et al., 1994, Science 266, 120–121). In addition, BRCA1 was found to be expressed at the same levels in normal individuals and sporadic breast cancers (Miki et al., 1994, Science 266, 66–71). Thus, the initial excitement over BRCA1 was followed by great disappointment.

The BRCA2 breast and ovarian cancer susceptibility gene has also recently been identified. (Wooster, R., et al., Nature 379: 789–792, 1995).

To date all tumor suppressors discovered encode proteins which are not secreted. Steeg, (review article), 1996, Nature Genetics 12:223. To treat the cancer associated with these tumor suppressors requires expressing the normal protein in the affected cell. Thus, these cancers have not been treatable with extracellular administration of the normal protein encoded by the tumor suppressor gene. For this reason, gene therapy has been proposed as the most likely means to supply a normal functional tumor suppressor protein.

This invention significantly modifies the state of the BRCA art by providing that the BRCAs are secreted and thus are amenable to direct therapy or prevention by contacting the BRCA receptor on the cell surface. In addition, the invention provides that BRCA1 is indeed underexpressed in sporadic breast cancer and thus sporadic breast cancer is amendable to therapy and prevention by correcting the BRCA deficiency. Other embodiments are also provided.

SUMMARY OF THE INVENTION

An aspect of this invention concerns a purified and isolated BRCA1 cleavage protein; and biologically functional and structural equivalents thereof.

Another aspect of this invention is that the BRCA1 protein is a secreted tumor suppressor/growth inhibitor protein that exhibits tissue-specific tumor suppression/growth inhibition activity.

Important aspects of the present invention concern isolated DNA segments and recombinant vectors encoding the BRCA1 and the BRCA2 proteins, and the creation and use of recombinant host cells through the application of DNA technology, which express the BRCA1 and BRCA2 proteins.

The present invention concerns DNA segments, isolatable from human breast and ovarian tissue, which are free from genomic DNA and which are capable of conferring tumor suppressor/growth inhibitor activity in a recombinant host cell when incorporated into the recombinant host cell. As used herein, the term "breast or ovarian tissue" refers to normal and cancerous ovarian breast tissues, as exemplified, but not limited to, by HMEC or MCF-7 cell lines. DNA segments capable of conferring tumor suppressor activity may encode complete BRCA1 and BRCA2 proteins, cleavage products and biologically actively functional domains thereof.

As used herein, the term "DNA segment" refers to a DNA molecule which has been isolated free of total genomic DNA of a particular species. Furthermore, a DNA segment encoding a BRCA1 protein or encoding a BRCA2 protein refers to a DNA segment which contains BRCA1 coding sequences or contains BRCA2 coding sequences, yet is isolated away from, or purified free from, total genomic DNA of Homo sapiens. Included within the term "DNA segment", are DNA segments and smaller fragments of such segments, and also recombinant vectors, including, for example, plasmids, cosmids, phage, viruses, and the like.

Similarly, a DNA segment comprising an isolated or purified BRCA1 gene or BRCA2 gene refers to a DNA segment including BRCA1 coding sequences isolated substantially away from other naturally occurring genes or protein encoding sequences or including BRCA2 coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the BRCA1 gene or the BRCA2 gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a BRCA1 protein that includes within its amino acid sequence the amino acid sequence of SEQ ID NO:2. In other particular embodiments, the invention concerns isolated DNA segments and recombinant vectors incorporating DNA sequences which encode a protein that includes within its amino acid sequence the amino acid sequence of the BRCA1 protein corresponding to human breast or ovarian tissue.

In particular embodiments, the invention concerns isolated DNA segments and recombinant vectors incorporating DNA sequences which encode a BRCA2 protein that includes within its amino acid sequence the amino acid sequence of SEQ ID NO:4. In other particular embodiments, the invention concerns isolated DNA segments and recombinant vectors incorporating DNA sequences which encode a protein that includes within its amino acid sequence the amino acid sequence of the BRCA2 protein corresponding to human breast or ovarian tissue.

It will also be understood that this invention is not limited to the particular nucleic acid and amino acid sequences of SEQ ID NOS: 1, 2, 3 and 4. Recombinant vectors and isolated DNA segments may therefore variously include the BRCA1 and BRCA2 encoding regions themselves, coding regions bearing selected alterations or modifications in the basic coding region, or they may encode larger polypeptides which nevertheless include BRCA1 or BRCA2 encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in SEQ ID NO:2 or SEQ ID NO:4, and methods of treating breast or ovarian cancer using these DNA segments. Naturally, where the DNA segment or vector encodes a full length BRCA1 or BRCA2 protein, or is intended for use in expressing the BRCA1 or BRCA2 protein, the most preferred sequences are those which are essentially as set forth in SEQ ID NO:1 and SEQ ID NO:3 and which encode a protein that exhibits tumor suppressor activity in human breast and ovarian cancer cells, as may be determined by the breast and ovarian cancer cell growth inhibition experiments, as disclosed herein.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:2 will be sequences which are "essentially as set forth in SEQ ID NO:2". The term "a sequence essentially as set forth in SEQ ID NO:4" has a similar meaning.

In particular embodiments, the invention concerns gene therapy methods that use isolated DNA segments and recombinant vectors incorporating DNA sequences which encode a protein that includes within its amino acid sequence an amino acid sequence in accordance with SEQ ID NO:2 or in accordance with SEQ ID NO:4, SEQ ID NO:2 and SEQ ID NO:4 derived from breast or ovarian tissue from Homo sapiens. In other particular embodiments, the invention concerns isolated DNA sequences and recombinant DNA vectors incorporating DNA sequences which encode a protein that includes within its amino acid sequence the amino acid sequence of the BRCA1 protein from human breast or ovarian tissue, or which encode a protein that includes within its amino acid sequence the amino acid sequence of the BRCA2 protein from human breast or ovarian tissue.

In certain other embodiments, the invention concerns isolated DNA segments and recombinant vectors that include within their sequence a nucleic acid sequence essentially as set forth in SEQ ID NO:1, or a nucleic acid sequence essentially as set forth in SEQ ID NO:3, and methods of treating breast or ovarian cancer using these sequences. The term "essentially as set forth in SEQ ID NO:1" is used in the same sense as described above and means that the nucleic acid sequence substantially corresponds to a portion of SEQ ID NO:1, respectively, and has relatively few codons which are not identical, or functionally equivalent, to the codons of SEQ ID NO:1, respectively. Again, DNA segments which encode proteins exhibiting tumor suppression activity of the BRCA1 and BRCA2 proteins will be most preferred. The term "functionally equivalent codon" is used herein to refer to codons that encode the same amino acid, such as the six codons for arginine or serine, and also refers to codons that encode biologically equivalent amino acids (see FIG. 2). The term "essentially as set forth in SEQ ID NO:3" has a similar meaning.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1 or SEQ ID NO:3, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent BRCA1 and BRCA2 proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test BRCA1 and BRCA2 mutants in order to examine tumor suppression activity at the molecular level.

If desired, one may also prepare fusion proteins and peptides, e.g., where the BRCA1 or BRCA2 coding regions are aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the BRCA1 or BRCA2 gene(s), e.g., in breast or ovarian cancer cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a BRCA1 or BRCA2 gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, *Molecular Cloning Laboratory Manual,* 2d Edition. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, a breast selective MMTV promoter and the LXSN promoter, which are more fully described below.

As mentioned above, in connection with expression embodiments to prepare recombinant BRCA1 and BRCA2 proteins and peptides, it is contemplated that longer DNA segments will most often be used, with DNA segments encoding the entire BRCA1 or BRCA2 protein, functional domains or cleavage products thereof, being most preferred. However, it will be appreciated that the use of shorter DNA segments to direct the expression of BRCA1 and BRCA2 peptides or epitopic core regions, such as may be used to generate anti-BRCA1 or anti-BRCA2 antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 5,600 nucleotides for a protein in accordance with SEQ ID NO:2 or a minimum coding length on the order of about 10,300 nucleotides for a protein in accordance with SEQ ID NO:4.

Naturally, the present invention also encompasses DNA segments which are complementary, or essentially complementary, to the sequence set forth in SEQ ID NO:1 or the sequence set forth in SEQ ID NO:4. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of base pairing to codons that encode the same amino acid, such as the six codons for arginine or serine, and also refers to codons that encode biologically equivalent amino acids (See FIG. 2).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 20% and about 50%; or more preferably, between about 50% and about 70%; or even more preferably, between about 70% and about 99%; of nucleotides which are identical to the nucleotides of SEQ ID NO:1 or to the nucleotides of SEQ ID NO:3, will be sequences which are "essentially as set forth in SEQ ID NO:1" and will be sequences which are "essentially as set forth in SEQ ID NO:3". Sequences which are essentially the same as those set forth in SEQ ID NO:1 or as those set forth in SEQ ID NO:3 may also be functionally defined as sequences which are capable of hybridizing to a nucleic acid segment containing the complement of SEQ ID NO:1 or to a nucleic acid segment containing the complement of SEQ ID NO:3 under relatively stringent conditions. Suitable relatively stringent hybridization conditions will be well known to those of skill in the art (Sambrook et al, 1989, *Molecular Cloning Laboratory Manual,* 2d Edition).

| List of Abbreviations | |
| --- | --- |
| MCF-7 | An immortalized cell line derived from a metastasis of human breast cancer |
| HMEC | A primary (non-immortalized) cell line derived from breast epithelial cells obtained during reduction mammoplasty |
| MDA-MB-468 | An immortalized cell line derived from a metastasis of human breast cancer |
| Sf9 | Insect cells widely used in the art with baculovirus vectors |
| cDNA | Complementary DNA obtained from an RNA template |
| DNA | Deoxyribonucleic Acid |
| RT-PCR | Reverse Transcriptase-Polymerase Chain Reaction |

BRIEF DESCRIPTION OF THE DRAWINGS

FIG. 1 lists the C-terminal and N-terminal amino acid sequences [SEQ ID NOs:5, 6, 7] used as antigens to generate antibodies for the purified and isolated BRCA1 protein described herein.

FIG. 2 is a table of the genetic code.

FIG. 5 is a diagram showing sequence alignment of the granin region of selected granin family members compared with BRCA1 and BRCA2.

FIG. 6 is Table I, which shows inherited BRCA1 mutations and type of cancer.

FIG. 7 is Table II, which shows effect of BRCA1 Expression Vectors on growth.

FIG. 8 is Table III, which shows inhibition of tumorigenesis by BRCA1.

FIGS. 9A–9D show the sequence of the BRCA1 gene [SEQ ID NO:1].

FIGS. 10A–10F show the sequence of the BRCA2 gene [SEQ ID NO:3].

FIGS. 11A–11C show the sequence of the BRCA2 protein [SEQ ID NO:4].

FIG. 13 is an immunoprecipitation/immunoblot analysis of MDA-MB-468 cell lysates with C-19 antisera.

FIG. 14 is a C-20 immunoblot analysis of recombinant Baculovirus produced BRCA1 (marked by arrow) compared with uninfected Sf9 cells (Control).

FIG. 15 is a V8 Protease Map of Native and Recombinant BRCA1.

DESCRIPTION OF THE PREFERRED EMBODIMENT

Figure 3:
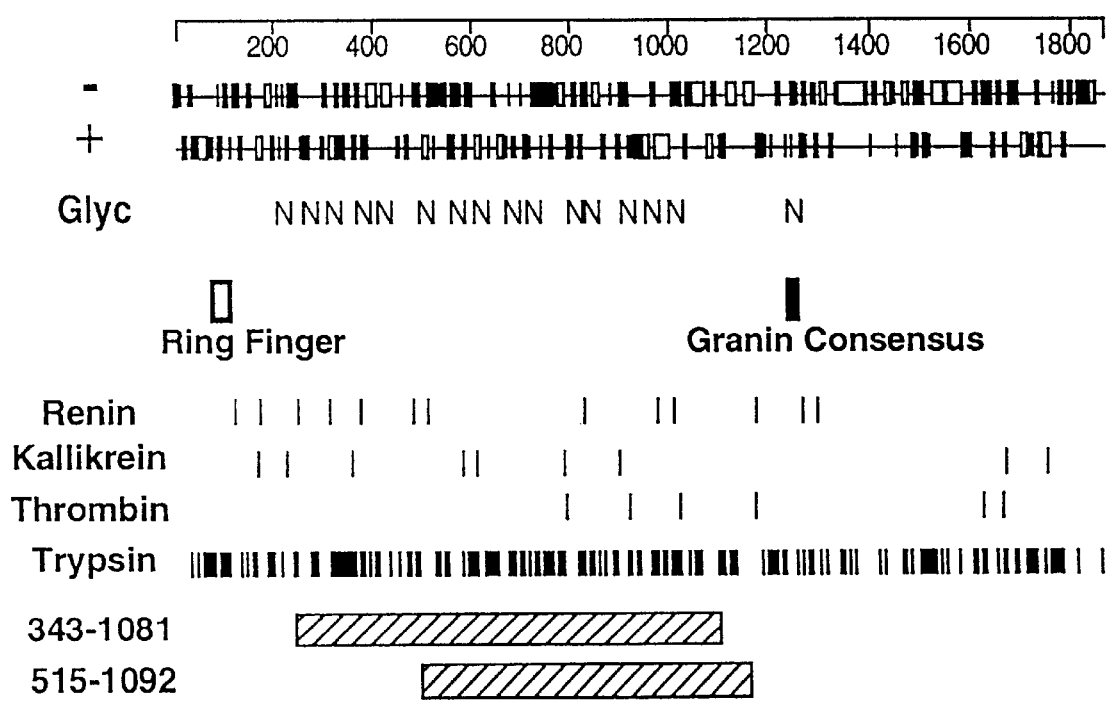
FIG. 3 is a diagram showing structural features of the human BRCA1 protein [SEQ ID NO:2] covering 1864 amino acids.

For the purposes of the subsequent description, the following definitions will be used:

Nucleic acid sequences which are "complementary" are those which are capable of base-pairing according to the standard Watson-Crick complementarity rules. That is, that the larger purines will always base pair with the smaller pyrimidines to form only combinations of Guanine paired with Cytosine (G:C) and Adenine paired with either Thymine (A:T) in the case of DNA or Adenine paired with Uracil (A:U) in the case of RNA.

"Hybridization techniques" refer to molecular biological techniques which involve the binding or hybridization of a probe to complementary sequences in a polynucleotide. Included among these techniques are northern blot analysis, southern blot analysis, nuclease protection assay, etc.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

"Probe" refers to an oligonucleotide or short fragment of DNA designed to be sufficiently complementary to a sequence in a denatured nucleic acid to be probed and to be bound under selected stringency conditions.

"Label" refers to a modification to the probe nucleic acid that enables the experimenter to identify the labeled nucleic acid in the presence of unlabeled nucleic acid. Most commonly, this is the replacement of one or more atoms with radioactive isotopes. However, other labels include covalently attached chromophores, fluorescent moieties, enzymes, antigens, groups with specific reactivity, chemiluminescent moieties, and electrochemically detectable moieties, etc.

"Tissuemizer" describes a tissue homogenization probe.

"PCR technique" describes a method of gene amplification which involves sequenced-based hybridization of primers to specific genes within a DNA sample (or library) and subsequent amplification involving multiple rounds of annealing, elongation and denaturation using a heat-stable DNA polymerase.

"RT-PCR" is an abbreviation for reverse transcriptase-polymerase chain reaction. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase produced by Thermus aquaticus for its amplification action.

"Nuclease protection assay" refers to a method of RNA quantitation which employs strand specific nucleases to identify specific RNAs by detection of duplexes.

"In situ hybridization of RNA" refers to the use of labeled DNA probes employed in conjunction with histological sections on which RNA is present and with which the labeled probe can hybridize allowing an investigator to visualize the location of the specific RNA within the cell.

"Cloning" describes separation and isolation of single genes.

"Sequencing" describes the determination of the specific order of nucleic acids in a gene or polynucleotide.

The term "BRCA1 targeted growth inhibitor agent", as used herein and in the claims, is defined as the BRCA1 protein characterized herein, whether isolated and purified directly from a natural source such as mammalian ovarian or breast cells, or produced using recombinant methods; the targeted growth inhibitor having the biological activity of tumor suppression and/or growth inhibition activity in mammalian breast or ovarian cancer cells and which binds the BRCA1 receptor; and the term "BRCA1 targeted growth inhibitor agent" also including biologically functional equivalents of the BRCA1 protein characterized herein, the term biologically functional equivalent defined herein to include, among others, proteins and protein fragments in which biologically functionally equivalent amino acids have been inserted and peptidomimetics.

The term "BRCA2 targeted growth inhibitor agent" is used herein as "BRCA1 targeted growth inhibitor agent" above but applies to BRCA2.

The term "homology" describes a mathematically based comparison of sequence similarities which is used to identify genes or proteins with similar functions or motifs.

The term "cleavage product" is defined as a polypeptide fragment produced from the targeted growth inhibitor described above by natural proteolytic processes. Preferably such a cleavage product will have biological activity including, but not limited to, tumor suppression and/or growth inhibition activity in mammalian breast or ovarian cancer cells. This term also includes such polypeptide fragments when produced via recombinant techniques and also includes biological functional equivalents of such fragments, the term biologically functional equivalent defined herein to include, among others, proteins in which biologically functionally equivalent amino acids have been inserted and peptidomimetics.

The term "granin box domain" is defined as the consensus granin box domain of amino acids set forth in FIGS. 3 and 5.

The term "recombinant host cell" is defined as a single cell or multiple cells within a cell line which are capable of undergoing genetic manipulation through well-known and art recognized techniques of transformation, transfection, transduction and the like. Examples of contemplated recombinant host cells include, but are not limited to, cell lines derived from normal or cancerous mammalian breast or ovarian tissue, other eukaryotic cells, and microorganisms. Specific examples of recombinant host cells described herein include Sf9 cells and HMEC cells.

The phrase "substantially identical to the carboxyl terminus of an amino acid sequence as essentially set forth in SEQ ID NO:2" is defined as an amino acid sequence including amino acids identical to the C-terminal amino acids in the amino acid sequence set forth in SEQ ID NO:2, or biologically functional equivalents of these amino acids. Preferred examples of the amino acid sequences are set forth in FIG. 1.

EXAMPLE 1

BRCA1 Encodes a 190 kDa Protein Expressed in Breast Epithelial Cells

As an initial step in the biochemical characterization of the BRCA1 gene product, antibodies were developed and the expression, localization, and function of BRCA1 protein were studied. These studies demonstrate that BRCA1 is a secreted, selectively growth inhibitory and represents a new member of the granin gene family.

Figure 12:
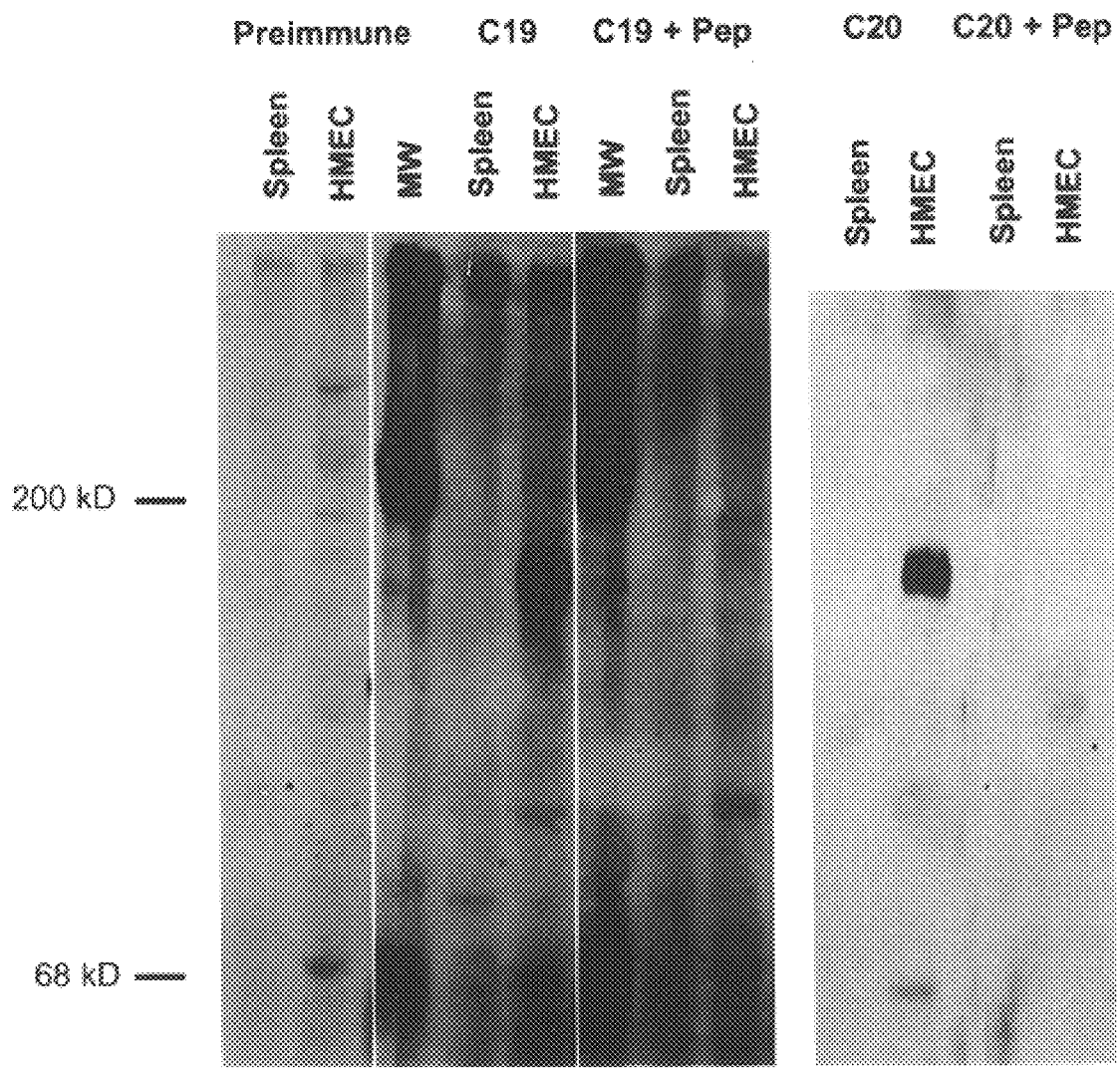
FIG. 12 is an immunoblot analysis of spleen and HMEC cell whole cell lysates probed with preimmune, immune, and immune plus peptide for C-19 antisera and C-20 affinity purified antibody and antibody plus peptide.

To enable BRCA1 protein expression studies a polyclonal rabbit antisera was raised against a peptide from the C-terminal portion of the predicted BRCA1 protein [SEQ ID NO:2]. This peptide corresponded to the last 19 C-terminal amino acids (C-19) [SEQ ID NO:5], which is listed in FIG. 1. The results produced by this antibody, which are more fully described below, were confirmed with antibodies against peptides from the last 20 C-terminal amino acids (C-20) [SEQ ID NO:6] and from the first 20 N-terminal amino acids (D-20) [SEQ ID NO:7] of the predicted BRCA1 protein [SEQ ID NO:2]. These antibodies were purchased from Santa Cruz Biotechnology, Santa Cruz, Calif., and the peptide sequences are also are listed in FIG. 1. A search of the SWISS PROT protein sequence database for the N-terminal and C-terminal 20 amino acid peptides at the 60% homology level revealed no entries other than BRCA1. Initially these antisera were screened using Western blot analysis of whole cell lysates from normal human mammary epithelial cells (HMEC-Clonetics, (Stampfer et al., 1980, *Growth of Normal Human Mammary Cells in Culture.* 16, 415–425)) and normal human spleen. Spleen was chosen as a negative control because Northern analysis demonstrated no expression of BRCA1 in spleen (Miki et al., 1994, *Science* 266, 66–71). The results of the experiments with the C-terminal antibodies were obtained with an immunoblot analysis of spleen and HMEC cell whole cell lysates probed with preimmune, immune, and immune plus peptide for C-19 antisera and C-20 affinity purified antibody and antibody plus peptide (FIG. 12). An immunoreactive band that is blocked by the addition of corresponding peptide is present at 190 kDa in the HMEC cells for both the C-19 and C-20 anti-peptide antisera. Note that the C-19 blot has been probed with immune ser um diluted 1:200 and that the C-20 blot has been probed with affinity purified antibody. No specific immunoreactivity is detected in the C-19 preimmune sera, and as expected no specific bands are detected in the spleen whole cell lysate by either C-19 or C-20. Several non-specific bands are present in the immune sera that do not block with the addition of peptide, but affinity purified C-20 antibody exhibits minimal non-specific cross reactivity. A minor band at approximately 70 kDa is identified, but appears to block with peptide indicating that this band represents a processed C-terminal fragment of the 190 kDa band. Similar studies were performed on antisera from three separate rabbits, raised against the C-terminal 19 peptide, and in each case, essentially similar results were seen, with some variation in the non-specific bands among individual rabbits, but all three react with a band at approximately 190 kDa that is not present in preimmune serum and is blocked with peptide.

A number of normal tissues and breast cancer cell lines were surveyed for the immunoreactive 190 kDa protein and the majority exhibited a decreased relative expression of BRCA1 in comparison to HMEC cells. The cell line MDA-MB-468 exhibited a very high level of BRCA1 expression, but the majority of other cells tested showed very low to absent (MCF-7, MB-157, MB-361) levels of expression. To analyze the ability of the antisera to immunoprecipitate the 190 kDa protein, radiolabelled whole cell lysates from MDA-MB-468 cells were immunoprecipitated with C-20 antisera (FIG. 13). The 190 kDa and 70 kDa species in the HMEC lane are blocked with the addition of peptide, but a number of non-specific bands including a 220 kDa species (Chen, et al, 1995, Science 270:789–791) are not blocked. Immunoprecipitation of MDA-MB-468 cells demonstrates a 190 kDa protein that is not present in the peptide addition control. In addition, the 70 kDa species is immunoprecipitated with antibody and blocked by the addition of peptide. It is noted that several other bands are identified that are not blocked with peptide, in particular at 205 and 220 kDa. This indicates that despite the 207 kDa size predicted from the BRCA1 coding sequence, the 205 kDa and 220 kDa bands do not represent BRCA1. These results are consistent with the 185 kDa estrogen-regulated protein reported by Gudas (Gudas, et al. 1995, Cancer Res., 55:4561–4565) but differ from the 220 kDa ubiquitous protein reported by Chen, particularly because the 220 kDa protein does not block with peptide.

While these results strongly suggested that the antisera was specific for a 190 kDa protein present in breast epithelial cells, further experiments were performed to demonstrate that this protein corresponded to BRCA1. A concern was that the full length coding sequence for BRCA1 predicts a protein of 207 kDa molecular weight and the protein that the antisera recognized was definitely less than 200 kDa, and approximately 190 kDa.

Figure 16:
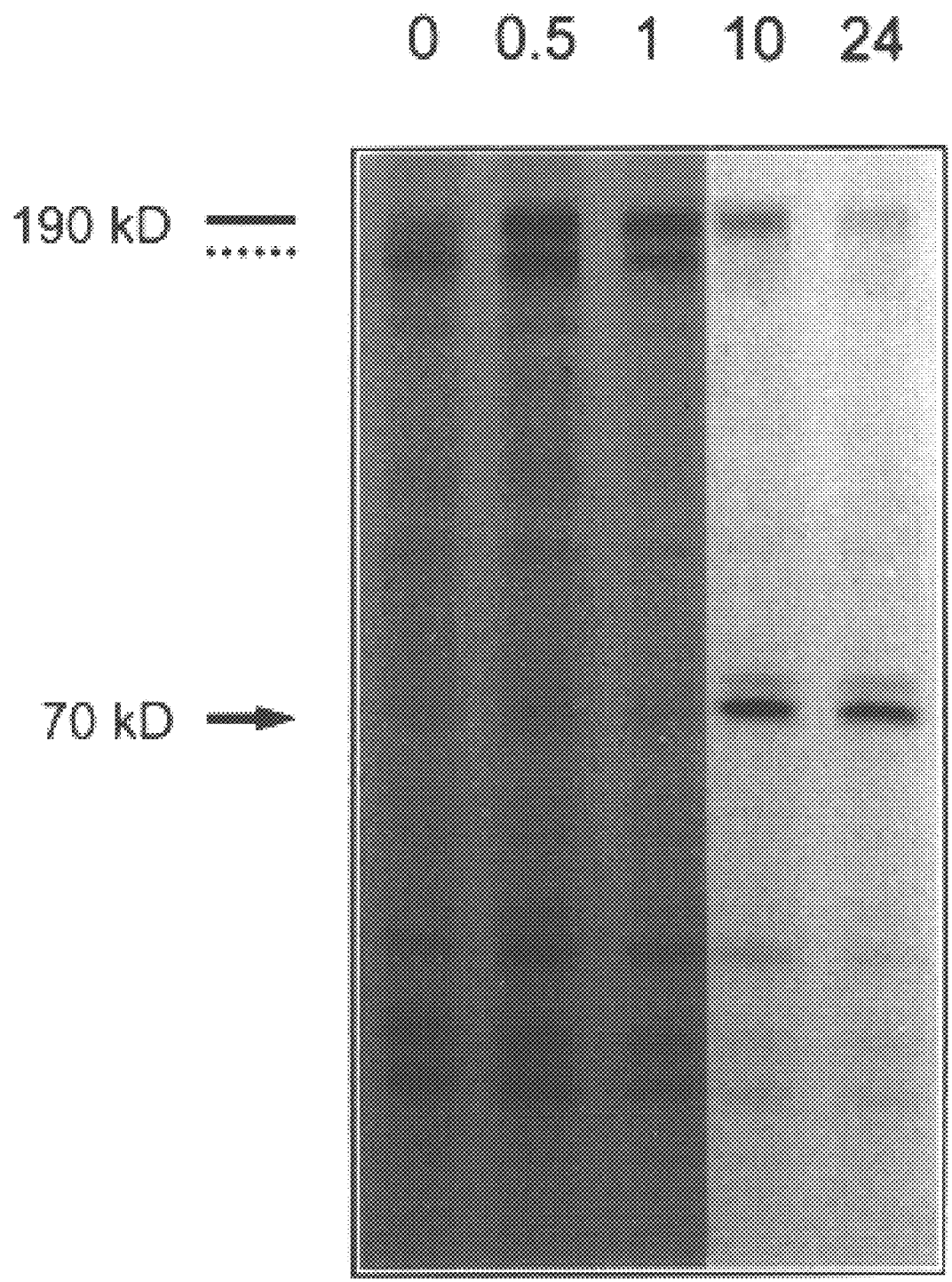
FIG. 16 is a Pulse-Chase Analysis of MDA-MB-468 Cells.

Therefore to confirm that the antisera recognized BRCA1 a full length BRCA1 cDNA was constructed and cloned into the baculovirus transfer vector pAcSG2 (PharMingen). This plasmid was subsequently utilized to produce recombinant BRCA1 baculovirus by co-transfection and homologous recombination. The antisera was then tested for its ability to recognize baculovirus expressed recombinant BRCA1. The results of these experiments were that the antibodies recognize a 180 kDa band in the BRCA1 recombinant virus infected cell lysates that is not present in the no infection control (FIG. 14). The recognition of this band is blocked by the addition of peptide and it is not present in the preimmune serum blot. To verify that the native 190 kDa protein and the recombinant 180 kDa protein were in fact the same protein, peptide mapping of the 190 kDa band from MDA-MB-468 cells and the 180 kDa protein from BRCA1 recombinant S89 cell lysates was performed as described in the methods. The digests were loaded onto a 4–20% gradient SDS-PAGE gel and immunoblotted with C-20 (FIG. 16). In FIG. 15, Lanes 1 through 3 and 4 through 6 represent increasing concentrations of V8 protease. The arrows at right indicate four identical sized molecular weight bands in lanes 3 and 6 that document that recombinant BRCA1 and the 190 kD band from MDA-MB-468 cells are identical proteins. This data confirmed that the antibodies are specific for BRCA1 protein. The difference in molecular weight between the recombinant and native protein is likely to be due to differences in glycosylation. These experiments demonstrate that the immunoreactive band completely blocks with peptide and is not present in control wild type virus infected lysates.

To characterize the 70 kDa species a pulse-chase experiment was performed that demonstrates that this band is a proteolytic fragment derived from the 190 kDa form. MDA-MB-468 cells were starved in cysteine and methionine deficient media and then pulsed with 35S labelled cysteine and methionine containing media with 3% dialyzed fetal bovine serum for three hours. The cells were then chased in L-15 media with 10% fetal bovine serum for increasing periods of time and harvested in lysis buffer. The lysates were immunoprecipitated, electrophoresed and the dried gel was autoradiographed (FIG. 16). In this experiment, it was shown that BRCA1 is initially synthesized as a 185 kDa form that is subsequently processed to a 190 kDa species. This represents glycosylation of the newly synthesized protein. Initially, no 70 kDa form is present, but co-incident with the appearance of the fully glycosylated form, the 70 kDa form appears. Subsequently, as the 190 kDa signal decreases with time post-labelling, the 70 kDa band increases in intensity. These findings indicate that the 70 kDa band is a proteolytic fragment, or cleavage product, of the 190 kDa protein. Other cleavage products were also isolated, including a 110 kDa species and a 130 kDa species.

Having demonstrated that the antibodies recognize BRCA1 protein, immunohistochemical analysis on formalin fixed, paraffin-embedded normal breast tissue were performed to analyze the distribution of BRCA1 within the breast. The results demonstrated that luminal epithelial cells (Page and Anderson, 1987, Nature Genetics 2, 128–131) within breast acini and ducts stain positively but myoepithelial cells and supporting stromal cells did not stain. No staining was observed when either primary antibody was deleted or peptide was added to the incubation. Staining was present diffusely throughout the cytoplasm and was not localized to the nucleus.

In summary, then, a 190 kDa protein was demonstrated to be the BRCA1 gene product by a number of independent criteria: 1) three different antibodies directed against two different regions of the predicted gene product react specifically in western blots and are blocked by appropriate peptides; 2) The C-20 antibody specifically immunoprecipitates the protein; 3) The C-20 antibody specifically recognizes the recombinant protein expressed in baculovirus; 4) Peptide mapping experiments definitely demonstrate that the 190 kDa protein recognized in MDA-MB-468 cells and the recombinant virus infected Sf9 cells are the same. Immunohistochemical studies indicate that BRCA1 protein is present in the luminal epithelial cells which are presumed be the cells of origin for the vast majority of hereditary and sporadic breast cancers.

EXAMPLE 2

Figure 17:
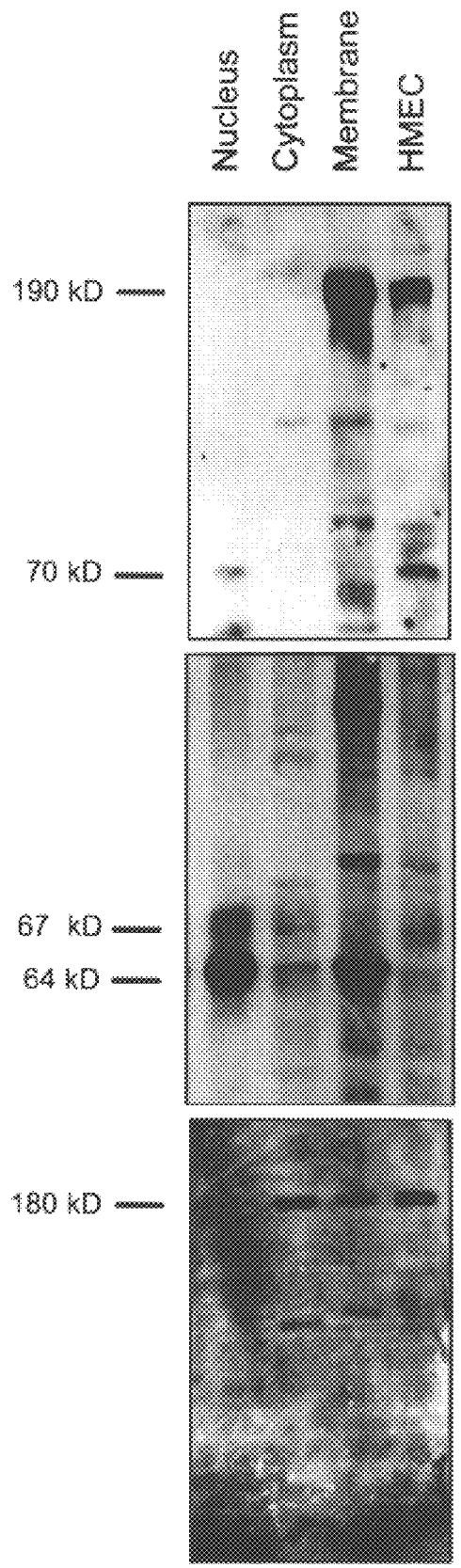
FIG. 17 is an immunoblot analysis of nuclear, cytoplasmic and membrane fractions of HMEC cells paired with corresponding whole cell lysate and probed for BRCA1 (C-19), c-myc, and PDGFR beta.
Figure 18:
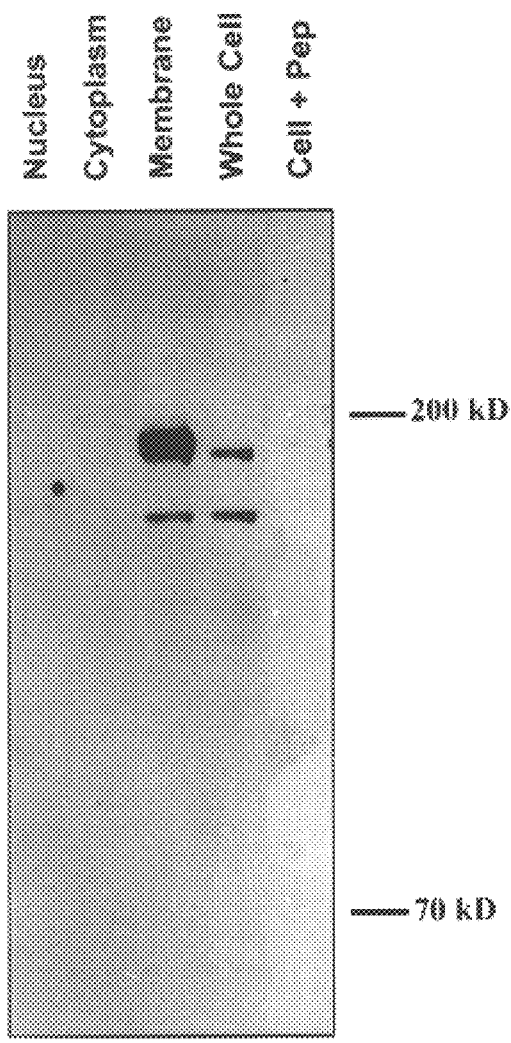
FIG. 18 is an immunoblot analysis of nuclear, cytoplasmic and membrane fractions of HMEC cells paired with corresponding whole cell lysate and probed with D-20 N-terminal antibody plus and minus peptide.
Figure 19:
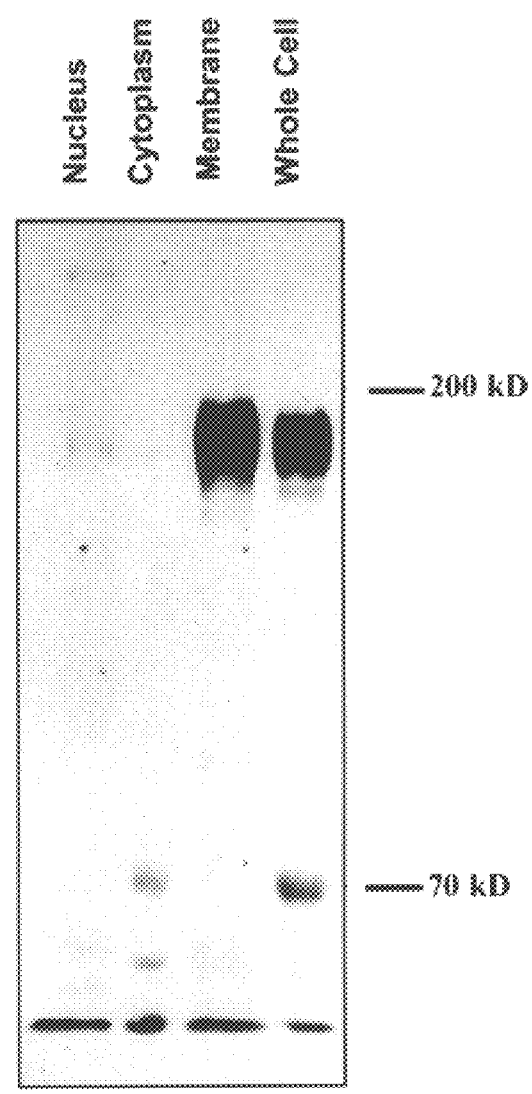
FIG. 19 is an immunoblot analysis of nuclear, cytoplasmic and membrane fractions of MDA-MB-468 cells paired with corresponding whole cell lysate probed with C-20 antibody.

BRCA1 is Predominately Localized in the Membrane Fraction of Breast Epithelial Cells Due to the immunohistochemical studies, a series of experiments to determine more precisely the localization of BRCA1 within the cell was initiated. The first such experiment was a cell fractionation experiment designed to segregate nuclear, cytoplasmic, and membrane compartments of HMEC cells. As shown in FIG. 17, the cell fractionation analysis included immunoblot analysis of nuclear, cytoplasmic and membrane fractions of HMEC cells paired with corresponding whole cell lysate and probed for BRCA1 (C-19 antibody), c-myc, and PDGFR beta; and identical fractions as above probed with D-20 N-terminal antibody plus and minus peptide (FIG. 18). The cell fractionation analysis also included immunoblot analysis of nuclear, cytoplasmic and membrane fractions of MDA-MB-468 cells paired with corresponding whole cell lysate probed with C-20 antibody (FIG. 19). The results of this cell fractionation experiment clearly demonstrate that the 190 kDa species of BRCA1 is present and greatly enriched for in the membrane fraction of HMEC cells. Essentially no 190 kDa BRCA1 could be detected in either the nuclear or cytoplasmic fractions, although the 70 kDa protein is present in the nuclear fraction. As a control for the fractionation procedure parallel blots were probed with antisera for c-myc and platelet-derived growth factor receptor beta (PDGFR). These blots demonstrated that the nuclear fraction is greatly enriched for the 67 and 64 kDa c-myc proteins (Alexandrova et al., 1995, *Mol. Cell. Biol.* 15:5188–5195) and the cytosolic and membrane fractions show PDGFR as expected. These results were confirmed with the antibody to the N-terminal portion of BRCA1 (D-20). This antibody detects the 190 kDa form of BRCA1 and an additional 165 kDa species in HMEC cells. Both of these bands are blocked with the addition of peptide and are present in the membrane fraction exclusively. Note that this antibody does not detect the 70 kDa species identified in the C-terminal peptide blots.

To investigate the possibility that subcellular localization of BRCA1 might be altered in malignant breast cells, fractionation studies on MDA-MB-468 cells that express high levels of BRCA1 protein were performed (FIG. 19). These studies demonstrated that in parallel with findings in HMEC cells the 190 kDa form of BRCA1 is also greatly enriched in the membrane fraction of MDA-MB-468 cells. In contrast to HMEC cells however, there appears to be a small amount of the 190 kDa species in the nuclear fraction of MDA-MB-468 cells. It is also noted that in contrast to HMEC cells, the 70 kDa species is present exclusively in the cytosolic fraction of MDA-MB-468 cells.

To further investigate the precise subcellular localization of BRCA1 confocal microscopy utilizing the affinity purified C-20 antisera was employed. These experiments indicated that the C-20 antibody exhibits diffuse granular staining that is predominately localized in the cytoplasm of HMEC cells. The nucleus and Golgi compartment were localized in these experiments, and this provided the capability to identify co-localization of BRCA1 in both the nucleus and Golgi complex. Simultaneous triple staining for the nucleus, Golgi complex and BRCA1 again demonstrated a predominant granular cytoplasmic distribution for BRCA1, with co-localization in both the nucleus and Golgi complex. These findings are in agreement with the cell fractionation studies of HMEC cells, despite the inability of those studies to detect the 190 kDa BRCA1 form in the nucleus, because the 70 kDa form was present in the nuclear fraction and would be expected to be detected by C-terminal antibody.

In summary, then, the above studies demonstrate that the majority of BRCA1 protein is non-nuclear and membrane-associated. Cell fractionation studies show the 190 kDa BRCA1 protein resides primarily in the membrane-associated fraction, but the p70 protein is localized in the nucleus of normal breast cells and the cytoplasm of MB-486 breast cancer cells. The distinct membrane-associated and nuclear localization patterns result from the unprocessed and the 70 kDa processed form, respectively. There is definite co-localization with the 190 kDa BRCA1 protein and the Golgi marker supporting the trafficking of BRCA1 through the Golgi prior to its packaging into secretory granules.

EXAMPLE 3
BRCA1 is a Member of the Granin Family of Secretory Proteins and Localizes to Secretory Vesicles Having identified BRCA1 as being present in the membrane fraction of breast epithelial cells and having a large granular cytoplasmic pattern of staining, a homology search of BRCA1 was performed, focusing on motifs that might explain the apparent membrane localization of BRCA1. A search on the SWISS PROT database of the MacDNAsis PRO v3.0 software package was performed and several features of biologic and functional importance were identified, as shown in FIG. 3. In FIG. 3, (−) and (+) mark location of charged residues and glyc shows potential N-linked glycosylation sites. RING finger and granin (amino acids 1214–1223) consensus are shown by open and closed boxes. Predicted protease cleavage sites for renin, kallikrein, thrombin, and trypsin are shown as thin lines. Regions deleted in the internal deletion mutants are shown as shaded boxes below (343–1081 and 515–1092).

Figure 4:
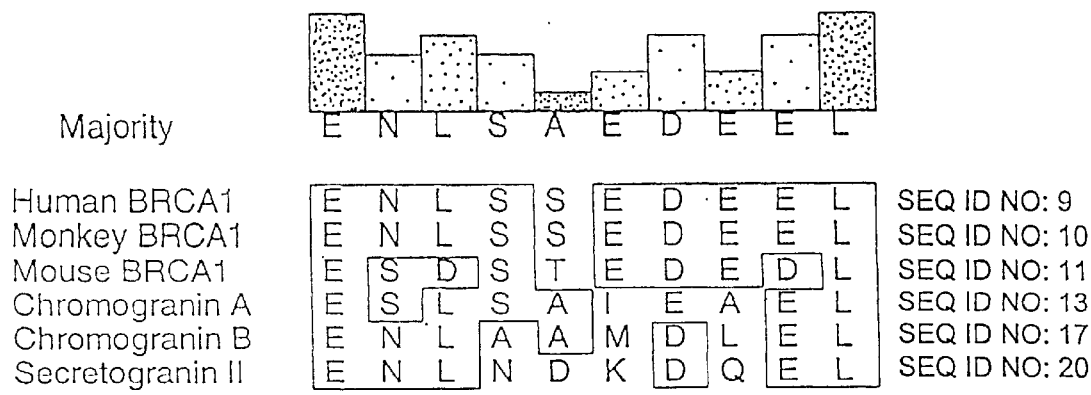
FIG. 4 is a diagram showing sequence alignment of the granin region of selected granin family members compared with BRCA1.

The SWISS PROT search revealed that BRCA1 has homology to the granin consensus site as shown in FIG. 4. In FIG. 4, consensus sequence is shown in bold at the bottom. Sequences are human unless otherwise stated. The granin motif spans amino acids 1214–1223 of BRCA1. Note that human BRCA1 completely satisfies the ten amino acid granin consensus and exhibits the other structural features of the family. The probability that BRCA1 would exhibit a perfect granin consensus by chance alone is 0.0018 (or one in 555). The rationale for this calculation is given at the bottom of FIG. 4.

Figure 20:
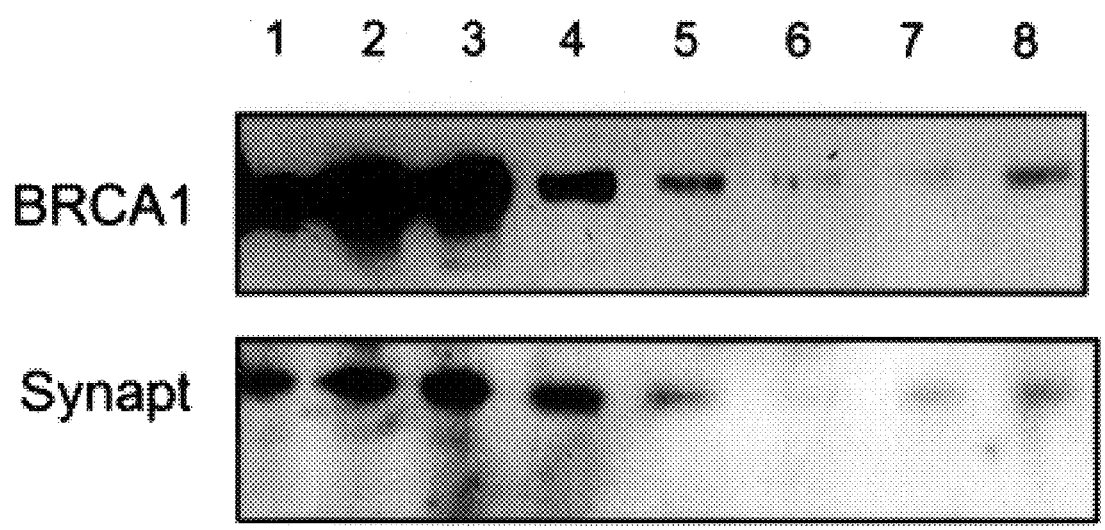
FIG. 20 depicts assay of MDA-MB-468 cell fractions produced by sucrose gradient for synaptophysin and BRCA1 immunoreactivity.

To investigate the hypothesis that BRCA1 behaves biochemically as a granin, the following series of experiments were executed. To document the presence of BRCA1 in secretory vesicles, cell organelles from MDA-MB-468 cells were fractionated by sucrose gradient centrifugation and the fractions were assayed for synaptophysin (a highly specific marker for secretory vesicles) and BRCA1 immunoreactivity. As seen in FIG. 20, coordinate expression of BRCA1 and synaptophysin was noted, which indicates the co-localization of these proteins in secretory vesicles. These results document the co-localization of synaptophysin and BRCA1 in fractions expected to contain secretory vesicles.

Figure 21:
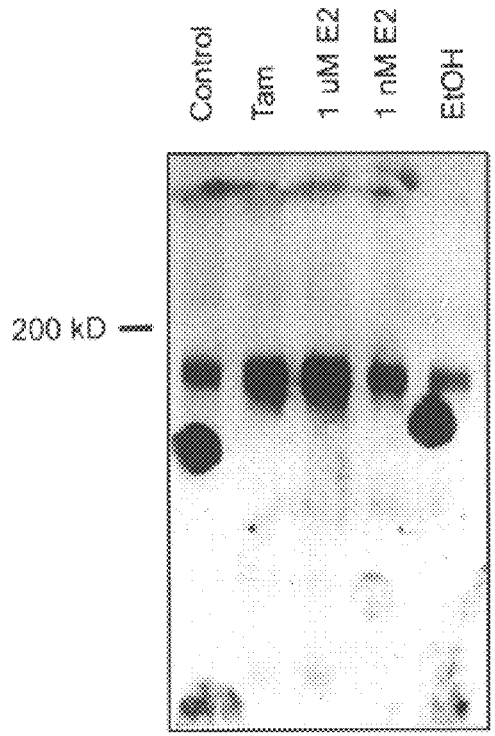
FIG. 21 depicts estrogen regulation of BRCA1 protein.

Since granins have been shown to be regulated by estrogens (Fischer-Colbrie et al., 1991, *J. Neuroendoctinol.* 121, 125–130) HMEC cells were stimulated with estrogen and tamoxifen and increased expression of BRCA1 was demonstrated, as reported previously by others (Gudas, et al. 1995, *Cancer Res.*, 55:4561–4565; Marquis et al. ,1995, *Nature Genetics* 11, 17–26; Lane et al., 1995, *Genes & Development* 9, 2712–2722). The dose response was consistent with estrogen regulation of BRCA1 expression. As presented in FIG. 21, cell lysates from HMEC cells treated for 24 hours with tamoxifen (TAM), indicated concentrations of estrogen (E2), or ethanol control (ETOH). Note E2 dosage effect.

Figure 22:
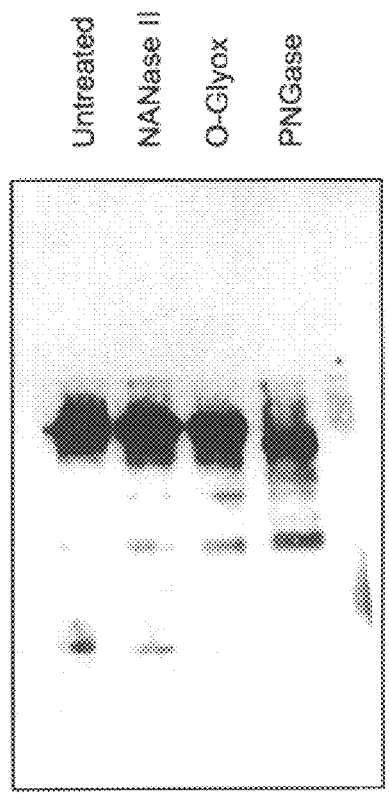
FIG. 22 depicts N-Linked glycosylation of BRCA1 protein.

HMEC cell membrane fractions were then treated with sequential deglycosylation enzymes (NANase II>O-Glycosidase DS>PNGase F to remove a2-3 and a2-6 N-acetylneuraminic acid, serine/threonine glycosylation (FIG. 22). N-linked glycosylation). A shift of protein following PNGase F treatment was noted, confirming N-linked glycosylation. Thus, BRCA1 exhibits N-linked glycosylation as predicted from the sequence analysis and shows little Ser/Thr glycosylation.

In addition, a heat stable fraction was prepared from recombinant baculovirus BRCA1 in a modification of the procedure of Thompson et al., (1992b), *Mol. Brain Res.* 12, 195–202, where cell pellets of infected Sf9 cells were sonicated, centrifuged, boiled for five minutes, and then centrifuged again. This heat soluble fraction was then analyzed by immunoblotting.

Figure 23:
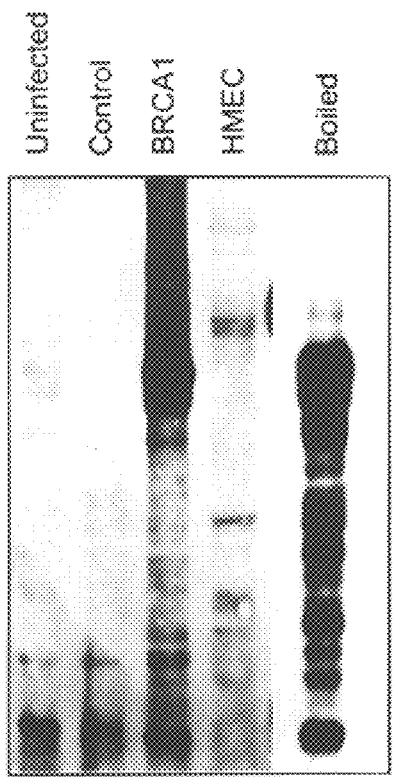
FIG. 23 depicts heat solubility of BRCA1 protein.

BRCA1 remained soluble after boiling, which is characteristic of granins. As seen in FIG. 23, the immunoblots included cell lysates from uninfected Sf9 cells, wild-type infected cells (control), BRCA1 infected cells, HMEC cells, and heat soluble fraction of Baculovirus produced recombinant BRCA1. Recombinant BRCA1 remains soluble after boiling.

Figure 24:
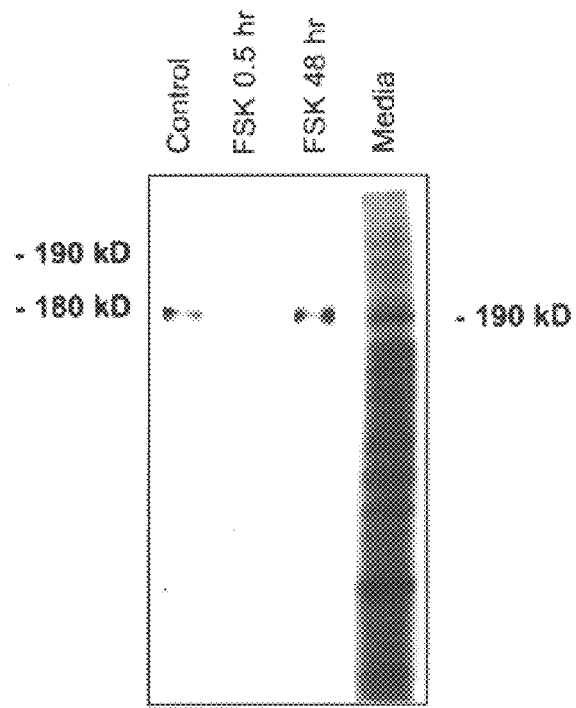
FIG. 24 is a Western blot of HMEC cell lysates: control; stimulated with 10 mM forskolin 0.5 hours post stimulation; and 48 hours post stimulation and also includes radioimmunoprecipitation of BRCA1 From conditioned media (lane 4).

Additionally, HMEC cells were treated with 10 mM forskolin and a marked decrease in BRCA1 levels in whole cell lysates after 0.5 hours of treatment and a return to normal levels 48 hours later was observed. This data is consistent with forskolin stimulated release of secretory granules and subsequent replenishment. As seen in FIG. 24, the Western blot of HMEC cell lysates included: control, stimulated with 10 mM forskolin 0.5 hours post stimulation and 48 hours post stimulation. The Western blot also included a lane marked Media, which showed the results of radioimmunoprecipitation of 24 hour conditioned media from 35S-labelled MDA-MB-468 cells. These results indicate the presence of BRCA1 protein at 190 kDa. Media was supplemented with aprotinin, PMSF, leupeptin, and pepstatin.

To confirm that BRCA1 is in fact secreted MDA-MB-468 cells were metabolically labelled and the 190 k-Da band was immunoprecipitated from a 24 hour collection of labelled conditioned media. Finally, immunogold electron microscopy was performed with C-20 antibody on MDA-MB-468 cells and it was demonstrated that BRCA1 immunoreactivity localizes to secretory vesicles. These secretory vesicles were primarily located in the apical cytoplasm and were often found at the tips of microvilli extending into the extracellular space. A vesicle actively undergoing secretion was identified. These findings confirm that BRCA1 is a member of the granin family of secretory proteins.

In summary, then, BRCA1 has a granin box which shows 100% homology to the consensus (Huttner et al., 1991, *Trends Biochem. Sci.* 16, 27–30) and has the expected number of acidic residues and predicted isoelectric point of granin family members. Additional evidence that BRCA1 is a granin includes 1) Presence in secretory vesicle fractions; 2) Induction by estradiol; 3) Glycosylation which occurs on secretory proteins as they are transported through the rough endoplasmic reticulum (Kornfeld & Kornfeld, 1985, *Annu. Rev. Biochem.* 54, 631–664); 4) Solubility of boiled protein, a biochemical feature of the granin family; 5) Release of BRCA1 protein by forskolin induction of regulated secretion; and 6) localization in secretory vesicles by immunogold electron microscopy.

As more fully described below, internal deletions which eliminate key structural elements and glycosylation sites destroy growth inhibition and tumor suppression, thus indicating that BRCA1 tumor suppression and growth inhibition are mediated through its granin-like properties.

EXAMPLE 4

Normal BRCA1 inhibits growth of breast and ovarian cancer cells

Experiments to determine whether BRCA1 could function as a growth inhibitor or tumor suppressor were performed. Analysis of BRCA1 protein levels in human breast cancer cell lines indicated that MCF-7 cells had little or no BRCA1 protein. Analysis of MCF-7 cells for allelic loss at markers in the BRCA1 region indicates loss of at least 2 Mb including the BRCA1 region on one chromosome 17q21, and that the coding sequence of the retained BRCA1 allele was normal. Sal I linkered BRCA1 cDNA was cloned into the unique Xho I site of the retroviral vector LXSN for transfection studies. To rule out trivial effects on localization or stability, two in-frame internal deletion mutants were constructed which eliminated much of the region of BRCA1 containing acidic residues and putative glycosylation sites (D343–1081 and D515–1092), but preserved the granin homology region. Two termination codon mutants were constructed which resulted in predicted proteins containing 1835 and 340 amino acids.

Table I shows that transfection of the LXSN vector or the internal deletion mutants resulted in similar numbers of G418-resistant stable clones in a number of human cell lines.

Transfection of LXSN-BRCA1 into MCF-7 cells or Caov-4 ovarian cancer cells resulted in fewer clones which could not be expanded beyond 30 cells per clone. Some of these clones can be expanded in an enriched growth media containing GMSA, 10% fetal calf serum and 5 ng/ml EGF. This growth inhibitory effect of BRCA1 was confined to these cell types since fibroblast, lung cancer cells, and colon cancer cells were not growth inhibited by LXSN-BRCA1. The 340-amino acid truncated protein did not inhibit growth of any cell line. However, the 1835 amino acid protein significantly inhibited growth of ovarian cancer cells but not breast cancer cells. This indicates that distinct mechanisms mediate growth inhibition of ovarian cancer cells and breast cancer cells and that this difference depends on the length of the truncated protein.

EXAMPLE 5

Ovarian cancer susceptibility is differentially associated with protein truncations 5' of the granin region To determine whether the differential effects of short versus long truncated proteins on Caov-4 ovarian cancer cells were paralleled in human patients, the relative frequency of ovarian versus breast cancer among 166 patients in a series inheriting BRCA1 mutations was calculated (Table II). Mutations inherited by 19 patients were nonsense alterations leading to transcript instability and no mutant protein. Mutations inherited by 13 patients were missense alterations in the RING finger leading to complete but aberrant protein. All other mutations were protein-truncating mutations at sites throughout the gene. The difference in ovarian and breast cancer distribution between the two groups was statistically significant: ovarian cancer formed a significantly lower proportion (2%) of the cancers in patients with mutant proteins that would include the granin motif compared to the proportion (25%) of cancers in patients with more severely truncated proteins (X2=11.12, P<0.001). This result is consistent with the observation that the site of BRCA1 mutation is associated with relative susceptibility to ovarian versus breast cancer (Gayther et al., 1995, *Nature Genet* 11: 428–433). The analysis of Gayther et al., indicated that the correlation between genotype and phenotype was better described by a "change point" in the BRCA1 sequence than by a linear trend in locale of mutation. The granin consensus motif at codons 1214–1223 is well within the confidence limit for the estimated location (codons 1235–1243) of the optimal change point in that analysis.

EXAMPLE 6

BRCA1 Inhibits Breast but not Colon Tumorigenesis

BRCA1 gene transfer into MCF-7 cells inhibits tumorigenesis employing retroviral gene transfer. Supernatants containing $5 \times 10^7$ vector particles from LXSN and LXSN-BRCA1 PA317 producer clones were used to transduce $5 \times 10^7$ MCF-7 cells or OK3 colon cancer cells in culture which were subsequently injected into the flanks of six nude mice for each vector. The cells were not treated with G418 before injection because prior G418 treatment inhibits tumorigenesis in this model, but southern blots have demonstrated that 70–80% of MCF-7 cells are transduced by this protocol. Four weeks after injection there were MCF-7 tumors in 5/6 LXSN control mice but no tumors in LXSN-BRCA1 mice. Retroviral transduction by BRCA1 had no effect on colon tumor formation (Table III, FIG. 8). Tumors ultimately developed in all of the control mice and 4/6 LXSN-BRCA1 mice but the tumors in LXSN-BRCA1 mice were significantly smaller (XSN: 569 grams+60; LXSN-BRCA1: 60 grams+24) as illustrated in Table III, FIG. 8. Molecular analysis of tumor RNAs showed that the vector neo gene was present and expressed in all MCF tumors and that BRCA1 was detectable only in the four LXSN-BRCA1 transduced tumors. Because the ex vivo transduction strategy could inhibit tumor establishment but not necessarily inhibit growth of already established tumors, whether in vivo injection of LXSN-BRCA1 into established MCF-7 intraperitoneal tumors could inhibit the growth rate and improve survival was tested. This experimental approach results in retroviral vector integration into 20–40% of tumor cells. The results showed that while all five of the mice given the mutant BRCA1 retrovirus died in less than two weeks, the five mice injected with LXSN-BRCA1 survived from 15–41 days because the injection decreased the size and sequelae of the intraperitoneal tumors (Table III, FIG. 8).

The above studies were confirmed with stable transfectants expressing BRCA1. Using an enriched growth media MCF-7 transfectants containing the transferred BRCA1 gene were obtained. Although these clones grow at ⅓ the rate of mutant BRCA1 transfected clones in vitro, whether they would form tumors in nude mice was determined. Three distinct clones transfected with D343-1081 and four distinct clones transfected with BRCA1 (five mice per clone) were injected with the MCF-7 transfectants. The results show that 0/20 mice injected with BRCA1 transfectants developed tumors while 13/15 mice injected with mutant BRCA1 transfectants developed tumors, providing confirmation that BRCA1 inhibits tumorigenesis in nude mice (Table III). RT-PCR analysis demonstrated that the transfectants expressed the expected transfected BRCA1 or mutant BRCA1 mRNA.

Lactation is the most important secretory process in the breast and is defining for mammals. Indeed, the human breast is unique in that it does not fully differentiate until the first pregnancy and active lactation is followed by involution (Battersby et al., 1994, *Histopathology* 15:415–433). Thus during each lactation, cell numbers must be increased with the end of proliferation coinciding with the gain of secretory function. Following cessation of lactation the cell numbers must decrease to allow breast involution. Pairing secretion feedback with cell proliferation and growth inhibition mechanisms is reasonable and to be expected in this setting.

The identification of BRCA1 as a member of the granin family of secreted proteins indicates that it functions as a novel type of tumor suppressor gene.

Analysis of BRCA1 mutations shows that near full-length proteins do not protect against breast cancer, but far less often lead to ovarian cancer (Table II). Analysis of transfection experiments shows that near full-length BRCA1 proteins do not inhibit growth of breast cancer cells but do inhibit growth of ovarian cancer cells. This indicates that the mechanism of tumor suppression by BRCA1 differs for breast versus ovarian cancer.

Pregnancy and lactation are important protective factors for breast cancer. Although the epidemiologic basis of this is well-demonstrated, molecular correlates are lacking. The demonstration that BRCA1 mRNA is induced during mouse pregnancies and this work showing a secretory function for BRCA1 link a tumor suppressor gene with a epidemiologically-defined tumor suppression activity, early pregnancy.

EXAMPLE 7
Method of Screening for BRCA1 or BRCA2 Receptor

That BRCA1 is secreted has important implications for lactation and growth regulation of normal and malignant breast cells. The secreted BRCA1 protein acts on a cell surface receptor. The interaction between the BRCA1 protein and the receptor produces the beneficial effects, i.e. tumor suppression, in the target breast or ovarian tissue. Methods for isolating the BRCA1 receptor follow. The BRCA2 receptor can be similarly isolated.

Baculovirus BRCA1 can be purified from the insect cells with the C20 antibody and then labelled with radioactive iodine by standard methods. Cys61Gly and termination codon mutant BRCA1 proteins are prepared and labelled as a control. The labelled BRCA1 can then be used to perform binding studies to identify cells with BRCA1 receptors using Scatchard analysis; and to perform cross-linking studies which demonstrate the BRCA1 receptor(s) on polyacrylamide gels. These initial characterization methods are used to identify cells with high and low numbers of BRCA1 receptor(s) for purification and isolation studies. Once a cell line with high levels of BRCA1 receptor has been identified, then the protein is purified by the following approaches:
Approach A: Biochemical purification The cell line which expresses high levels of BRCA1 receptor is lysed and the protein from cell lysates or membrane preparations is purified by gel filtration followed by purification of the receptor with a column containing the BRCA1 ligand bound to a solid phase such as sepharose. The purified receptor protein can then be microsequenced and the gene cloned using degenerate oligonucleotides derived from the protein sequence.
Approach B:

Ligand is radiolabeled with 125I and then used to screen cell lines or tissues for specific binding by Scatchard analysis. Once such binding is identified, a cDNA library is constructed from that tissue or cell line and transfected into a cell line that does not exhibit specific binding. These transfected cells are then screened for newly acquired specific binding which indicates they have been transfected with a construct containing the gene for the BRCA1 receptor. Plasmid DNA from positive clones is then isolated and sequenced for identification. This single construct is then transfected back into the null cells to verify that binding of ligand is mediated by the transfected gene. (Kluzen et al, *Proc Natl Acad Sci USA* 89:4618–4622 (1992).

Alternatively, chimeric BRCA1 and immunoglobulin Fc molecules can be constructed. (LaRochelle et al, *J Cell Biol* 129:357–366 (1995)). These chimeric molecules are then be used to screen for binding to BRCA1 receptor on whole cells via flow cytometry. Alternatively, due to the presence of the immunoglobulin component of the molecule, cell lysates are screened by immunoblotting or by immunoprecipitation of metabolically labelled cells. This technique can identify BRCA1 binding proteins by a variety of different methods. Peptide digests of the identified proteins are then generated so that the peptides can be sequenced and the whole molecule cloned by a degenerative oligonucleotide approach.

EXAMPLE 8
Screen for BRCA1 Protein Mimetic Agents

Classical methods for identifying compounds which activate receptors are greatly facilitated by the prior identification of the receptor. However, knowledge of ligand structure domains and deletion and minimization methods allow the identification of active ligand mimetic drugs without first finding the receptor. As more fully described above, certain regions of the BRCA1 gene have been deleted to show which regions are essential for growth inhibitory activity. These studies can be continued in a systematic manner, revealing the regions of the molecule needed for its key activities. Upon identification of a small protein that can produce growth inhibition, systematic structural and functional analysis of the minimal protein can be performed as per the methods described in Li, et al., *Science* 270: 1657, 1995. Drugs can then be screened for and/or synthesized which mimic the peptide structure and consequently produce the desired effect.

Thus, provided also is a method of screening a compound for tumor suppressor activity comprising contacting the compounds with the BRCA1 or BRCA2 receptor, a compound which binds the receptor indicating a compound having potential tumor suppressor activity. Binding can be detected by well-known methods in the art, including, among others, radioimmunoassays and fluorescence assays.

EXAMPLE 9
Therapy method for ovarian cancer using the BRCA1 Gene.

Viral vectors containing a DNA sequence that codes for a protein having an amino acid sequence as essentially set forth in SEQ ID NO:2 can be constructed using techniques that are well known in the art. This sequence includes the BRCA1 protein. Viral vectors containing a DNA sequence essentially as set forth in SEQ ID NO:1 (the BRCA1 gene) can be also constructed using techniques that are well known in the art. Retroviral vectors such as the LXSN vector described above, adenoviral vectors, or adeno-associated viral vectors are all useful methods for delivering genes into ovarian cancer cells. The viral vector is constructed by cloning the DNA sequence essentially as set forth in SEQ ID:1 into a retroviral vector such as an ovarian selective vector. Most preferably, the full-length (coding region) cDNA for BRCA1 is cloned into the retroviral vector. The retroviral vector would then be transfected into virus producing cells in the following manner: Viruses are prepared by transfecting PA317 cells with retroviral vector DNAs which are purified as described in Wong et al., 1988, *Proceeding of the UCLA Symposia on Biology of Leukemias and Lymphomas.*, Golde D. (ed.), Alan R. Liss, Inc. 61:553–566. Following transfection, the PA317 cells are split and then treated with G418 until individual clones can be identified and expanded. Each clone is then screened for its titer by analyzing its ability to transfer G418 resistance (since the retroviral vector contains a Neomycin resistance gene). The clones which have the highest titer are then frozen in numerous aliquots and tested for sterility, presence of replication-competent retrovirus, and presence of mycoplasma. Methods generally employed for construction and production of retroviral vectors have been described above and in Miller, et al., 1990, *Methods in Enzym.* 217:581–599.

Once high titer viral vector producing clones have been identified, then patients with ovarian cancer can be treated by the following protocol: Viral vector expressing BRCA1 is infused into either solid tumors or infused into malignant effusions as a means for altering the growth of the tumor (since it is shown above that the BRCA1 protein decreases the growth rate of ovarian cancer cells). Because viral vectors can efficiently transduce a high percentage of cancer cells, the tumors will be growth inhibited.

EXAMPLE 10
The protein encoded by the BRCA2 breast and ovarian cancer susceptibility gene is a granin and a secreted tumor suppressor.

The protein encoded by the BRCA2 breast and ovarian cancer susceptibility gene (Wooster, R., et al., *Nature* 379: 789–792, 1995) includes a domain similar to the granin consensus at the C-terminus of the protein. As seen in FIG. 5, the sequence at amino acids 3334–3344 of Genbank locus HUS43746 matches six of the seven constrained sites of the granin consensus. BRCA2 and murine BRCA1 differ from the consensus at the same site. The granin motif in BRCA2 lies at the extreme C-terminal end of the protein, a locale characteristic of a known granin. This indicates that the protein encoded by the BRCA2 gene is also a secreted growth inhibitor. Use of both the BRCA1 and BRCA2 genes offer the opportunity for a unified approach to the treatment of inherited and sporadic breast cancer. Accordingly, the examples set forth above depicting the treatment of ovarian cancer, are equally applicable to the BRCA2 gene and the BRCA2 protein.

The identification of BRCA1 and BRCA2 as granins indicated that there is a granin superfamily of which consists of the subfamilies of chromogranins (chromogranins A, B and C); secretogranins (secretogranins III–V) and the BROCAgranins (BRCA1, BRCA2 and other tumor suppressor genes). This classification of granins into these subclasses is based on greater similarities within the subfamilies than with the superfamily as a whole. For example, the chromogranins share an additional region of homology besides the granin consensus and exhibit similar expression patterns; the secretogranins show less homology to the granin consensus than either chromogranins or BROCAgranins; the BROCAgranins BRCA1 and BRCA2 are cancer susceptibility genes, contain additional regions of homology, and are significantly larger (two-twenty times larger) than other granins described to date.

Thus, the invention provides in Example 3 and in this example a granin box consensus sequence shown in FIG. 5. Thus, provided is a family of proteins which share the consensus sequence that are tumor suppressor genes. BRCA1 and BRCA2 are members of this family. Other members may be identified and purified as tumor suppressor genes by genetic methods, by DNA-based searches for granin homology; or by cloning and characterization of granins in ovarian or breast cancer cells by biochemical methods. Such biochemical methods include the isolation and purification of proteins from secretory vesicles or Golgi by physical isolation methods, followed by development of antibodies to determine which proteins, followed by cloning of genes for secreted proteins after protein sequencing and cloning with degenerate oligonucleotide primers. A example of this method is described in Colomer et al., 1996, *J. Biological Chemistry* 271:48–55. Thus, other BROCA granins are contemplated to be within the scope of this invention.

EXAMPLE 11
Gene Therapy method using the BRCA2 Gene

Viral vectors containing a DNA sequence that codes for a protein having an amino acid sequence as essentially set forth in SEQ ID NO:4 can be constructed using techniques that are well known in the art, and as are more fully described above. This sequence includes the BRCA2 protein. Viral vectors containing a DNA sequence essentially as set forth in SEQ ID NO:3 (the BRCA2 gene) can be also constructed using techniques that are well known in the art. Retroviral vectors, adenoviral vectors, or adeno-associated viral vectors are all useful methods for delivering genes into breast cancer cells. An excellent candidate for use in breast cancer gene therapy is a Moloney-based retroviral vector with a breast selective MMTV promoter (Wong et al., 1988, *Proceeding of the UCLA Symposia on Biology of Leukemias and Lymphomas.*, Golde D. (ed.), Alan R. Liss, Inc.

61:553–566). The viral vector is constructed by cloning the DNA sequence essentially as set forth in SEQ ID NO:3 into a retroviral vector such as a breast selective vector. Most preferably, the full-length (coding region) cDNA for BRCA2 is cloned into the retroviral vector. The retroviral vector is then transfected into virus producing cells in the following manner: Viruses are prepared by transfecting PA317 cells with retroviral vector DNAs which are purified as described in Wong et al. Following transfection, the PA317 cells are split and then treated with G418 until individual clones can be identified and expanded. Each clone is then screened for its titer by analyzing its ability to transfer G418 resistance (since the retroviral vector contains a Neomycin resistance gene). The clones which have the highest titer are then frozen in numerous aliquots and tested for sterility, presence of replication-competent retrovirus, and presence of mycoplasm. The methods generally employed for construction and production of retroviral vectors have been described above and in Miller, et al., 1990, *Methods in Enzym.* 217:581–599.

Once high titer viral vector producing clones have been identified, then patients with breast cancer can be treated by the following protocol: Viral vector expressing BRCA2 protein is infused into either solid tumors or infused into malignant effusions as a means for altering the growth of the tumor. Because viral vectors can efficiently transduce a high percentage of cancer cells, the tumors will be growth inhibited.

EXAMPLE 12
Gene Transfer Using Liposomes

An alternative method of gene therapy using the BRCA1 and BRCA2 gene includes the use of liposome to deliver the DNA into the cells. By this method, the above described LXSN-BRCA1 plasmid would be incubated with a liposome preparation such as cationic liposomes and then the DNA liposome mix is added to cells or injected into an animal or patient. Generally, the liposome transfection method is of a lower efficiency than viral gene transfer methods. This method is useful because the BRCA1 and BRCA2 proteins are secreted proteins. Thus, if only a few percent of cells take up the DNA-liposome combination, it is likely that enough BRCA1 or BRCA2 protein will be produced and secreted from these cells to growth inhibit other cells. Liposomal transfection of nucleic acids into host cells is described in U.S. Pat. Nos. 5,279,833 and 5,286,634, the contents of each of which are herein incorporated by reference.

EXAMPLE 13
Anti-Sense Inhibition of the Production of BRCA1 Protein

The antisense inhibition of BRCA1 is described as follows. Antisense methods were used to demonstrate that BRCA1 expression inhibits cell growth. Unmodified 18 base deoxyribonucleotide complementary to the BRCA1 translation initiation site were synthesized and added to cultures of primary mammary epithelial cells (Stampfer et al. 1980, *In Vitro* 16: 415–425 (1980)) or MCF-7 breast cancer cells (Soule and McGrath, 1980, *Cancer Letters* 10, 177–189 (1980)).

The morphologic appearance of the cell lines was not noticeably changed by addition of antisense oligonucleotide, but the proliferative rate was faster. Incubation of cells with 40 uM anti-BRCA1 oligonucleotide produced accelerated growth of both normal and malignant mammary cells, but did not affect the growth of human retinal pigmented epithelial cells. An intermediate dose of anti-BRCA1 oligonucleotide produced a less pronounced but significant 310 increase in cell growth rate. This was not a toxic effect of the oligonucleotide since a control "sense" oligomer with the same GC content did not increase the proliferation rate, and because an addition of a 10 fold excess of sense oligomer to the anti-BRCA1 oligomer reversed the growth activation.

Thus, antisense inhibition of BRCA1 accelerates the growth of breast cancer cells. Because chemotherapy is most effective in cancer cells which are rapidly dividing, it is possible then to treat breast or ovarian cancer by accelerating growth of cancer cells by antisense inhibition of BRCA1 protein expression and by treating with chemotherapeutic drugs using standard chemotherapy protocols.

EXAMPLE 14
Biological Functional Equivalent Proteins and Peptides

Modification and changes may be made in the structure of the BRCA1 protein and the BRCA2 protein, or in cleavage products of these proteins, and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules or receptors, specifically the BRCA1 or BRCA2 receptor. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with counterveiling (e.g., antagonistic) properties. It is thus contemplated by the inventors that various changes may be made in the sequence of the BRCA1 and BRCA2 proteins or peptides (or underlying DNA) without appreciable loss of their biological utility or activity.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (1); Leucine=Leu (L); Lysine=Lys (K); Methionine=Met (M); Phenylalanine=Phe (F): Proline= Pro (P); Serine=Ser (S); Threonine=Thr (T); Tryptophan= Trp (W); Tyrosine=Tyr (Y); Valine=Val (V).

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with this invention.

It is also well understood that where certain residues are shown to be particularly important to the biological or structural properties of a protein or peptide, e.g., residues in active sites, such residues may not generally be exchanged. This is the case in the present invention where an exchange in the granin box domain may alter the fact that the BRCA1 and BRCA2 proteins are secreted.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine, and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for another amino acids having a similar hydropathic index or score and still retain a similar biological activity. In making changes based upon the hydropathic index, the substitution of amino acids whose hydropathic indices are within ±1 are particularly preferred, and those within ±2 is preferred, those which are within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids hose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Kyte & Doolittle, *J. Mol. Biol.,* 157:105–132, 1982; Hopp, U.S. Pat. No. 4,554,101.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

U.S. Pat. No. 4,554,101 (Hopp, incorporated herein by reference) teaches the identification and preparation of epitopes from primary amino acid sequences on the basis of hydrophilicity. Through identify epitopes from within an amino acid sequence such as the BRCA1 and BRCA2 sequences disclosed herein (SEQ ID NOs:2, 4). These regions are also referred to as "epitopic core regions".

Numerous scientific publications have been devoted to the prediction of secondary structure, and to the identification of epitopes, from analyses of amino acid sequences (Chou & Fasman, 1974a,b; 1978a,b 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993).

EXAMPLE 15
Treatment of Breast or Ovarian Cancer using Purified BRCA1 or BRCA2 Protein Alternatively, breast or ovarian cancer be treated by the administration of a therapeutically effective amount of the BRCA1 or BRCA2 protein via an efficient method, such as injection into a tumor. A therapeutically effective amount can be determined by one having ordinary skill in the art using well-known protocols.

It is important to note that breast and ovarian cancer cells have surface receptors which must be contacted by the BRCA1 or BRCA2. Thus, the BRCA1 or BRCA2 protein, an active fragment, or a small molecule mimetic binds directly to a receptor on the surface of the breast or ovarian cancer cells.

EXAMPLE 16
Method of Treating Breast or Ovarian Cancer Comprising Introducing the BRCA1 Receptor Gene and the BRCA1 protein into a Breast or Ovarian Cancer Cell The loss of the BRCA1 receptor in breast and ovarian cancer cells will lead to the proliferation and tumorigenesis in these cells. Thus, breast and ovarian cancer can be treated by introducing the BRCA1 receptor gene into breast or ovarian cancer cells using the gene therapy methods described above. This step will be followed by the administration of a therapeutically effective amount of the BRCA1 protein so that the BRCA1 protein contacts a receptor on a surface of the breast or ovarian cells. A therapeutically effective amount can be determined by one having ordinary skill in the art using well-known protocols.

EXAMPLE 17
Method of Preventing Breast or Ovarian Cancer using BRCA1 or BRCA2 Protein It is a well-established epidemiologic fact that parity and particularly early parity has a protective effect in regards to both breast and ovarian cancer risk. Because of various changes in the structure of society it is now quite common for women to delay childbirth and lose this natural protective effect. Since it is known that BRCA1 is induced in pregnancy and lactation, and it is demonstrated herein that BRCA1 is a secreted growth inhibitor that is specific for breast and ovarian cancer, the protective effect of pregnancy and lactation is due to BRCA1 expression. BRCA1 mediation of this effect for both breast and ovarian cancer presents a variety of strategies that are useful in decreasing breast and ovarian cancer risk, particularly in women that did not have a baby in their first twenty years and thus, were at a higher risk to develop breast or ovarian cancer. Thus, one can use a BRCA to prevent the first occurrence or a recurrence of breast and ovarian cancer. Examples of such strategies are presented below. While examples are provided, such strategies should not be limited to the examples.

BRCA1 protein might be used a chemopreventive agent by introducing BRCA1 directly into the peritoneal cavity of women as the whole protein, as a functional fragment, or as a functional cleavage product. In addition, compounds that induce expression of BRCA1 or activate its receptor, e.g. a small molecule mimetic, could also be introduced. Since BRCA1 is a secreted protein, the introduced BRCA1 will decrease ovarian cancer risk in the same manner that BRCA1 does normally when its expression is induced by pregnancy. The protective effect is also expected where BRCA1 expression is mediated by gene therapy method by either directly or indirectly inducing expression of BRCA1.

A similar rationale can be applied to breast cancer prevention. In this case, the whole BRCA1 protein; a functional fragment or a functional cleavage product thereof; or a pharmacological mimic can be used. In addition, compounds that induce expression of BRCA1 or activate its receptor, e.g. a small molecule mimetic, could also be used. Gene therapy approaches for increasing the expression of BRCA1 in breast directly or indirectly could also be used. Systemic agents that induce expression of BRCA1, or that mimic function and can replace BRCA1, such a peptidomimetic agent, could also be used. The delivery of such agents could take place by directly instilling the agent within the breast by introducing via the nipple. Finally, an implantable time release capsule can be used in a prevention strategy, either by placing such a capsule in the peritoneum for ovarian cancer, by implant such a capsule into the breast for breast cancer.

Since the BRCA2 protein includes a granin sequences and is also a secreted tumor suppressor protein, similar prevention strategies can be applied using the BRCA2 gene and protein.

Experimental Procedures for Examples 1–6
Tissues and Cell Culture

Cryopreserved primary cell lines (Passage 7) of normal human mammary epithelial (HMEC) cells, were obtained from Clonetics, Inc. The cryovial of HMEC was thawed and subcultured according to the instructions provided, which are a slight modification of published procedures (Stampfer et al, 1980, *Growth of Normal Human Mammary Cells in Culture.* 16, 415–425). Breast cancer cell lines were obtained from American Type Culture Collection (ATCC), Rockville, Md. Sf9 cells were obtained from ATCC.

Antibodies

C-terminal 19 peptide fragment was conjugated to keyhole limpet hemacyanin and injected into New Zealand white rabbits along with Freund's adjuvant according to standard protocols. C-20 and D-20 were provided by Santa Cruz Biotechnology. c-myc and PDGFR antibodies were provided by Steve Hann and William LaRochelle, respectively.

Cell Extracts, Immunoblotting, Immunoprecipitation, Northern blotting

Cell lysates, immunoblotting, and immunoprecipitation assays were performed according to previously published methods (Jensen et al, 1992, *Biochem.* 31: 10887–10892). RNA was isolated by published methods (Jensen et al, 1994, *Proc Natl Acad Sci USA* 91, 9257–9261) and probed with the T7 labelled EcoRI-Kpn I fragment from exon 11.

Cell Fractionation Studies

Cell fractionations were performed according the method of Fazioli, et al (1993, *Mol. Cell. Bio.* 13, 5814–5828). Briefly, cells in T175 flasks were washed twice with cold PBS/0.5 mM sodium vanadate, followed by a single washing in cold isotonic fractionation buffer (FB). Then, cold FB+protease inhibitors (PI) are added to the plates. The plates are incubated for 10 min, scraped, and homogenized with a Dounce tissue homogenizer. The nuclei were gently pelleted (375 g) at 4° C. and the supernatant (cytosolic and plasma membrane fraction) was saved. After washing the nuclear pellet with four aliquots of cold FB+PI+0.1% NP40 followed by centrifugation at 4° C., the nuclei were resuspended in cold FB and 2× lysis buffer+PI. The cytosolic and plasma membrane fraction was then ultracentrifuged (35,000 g) for 30 min at 4° C. and the supernatant was saved as the cytosolic fraction. The pellet (plasma membrane fraction) was resuspended in FB+PI and solubilized in 2× lysis buffer with PI. Following this, the nuclear and plasma membrane fractions are sonicated on ice for 10 seconds three times. They were then spun at 10,000 g at 4° C., and the supernatant was collected and saved as the soluble nuclear and plasma membrane fractions, respectively.

Confocal Imaging Studies

HMEC cells were plated into 35 mm culture dishes with glass bottom cover slips (Mat-Tek) and allowed to grow to 70% confluency. The cells were then rinsed, fixed in 4.0% paraformaldehyde in phosphate buffered saline at 4° C. (PBS, 0.01 M phosphate salts, and 0.15 M NaCl, pH 7.6) for ten minutes, and washed and permeabilized in PBS with 0.2% Triton X-100 for two minutes. Cells were blocked with 5% normal donkey serum in PBS. Primary antibodies were diluted in PBS containing 3.0% bovine serum albumin (BSA) and 0.1% Triton X-100 and consisted of rabbit anti-BRCA-1 (vendor) diluted 1:200 and a mouse monoclonal to a Golgi complex antigen (Biogenex; clone 371-4) diluted 1:10. No antibody and antibody to BRCA-1 preadsorbed with the peptide antigen were used as negative controls. Secondary antibodies were from Jackson Immunoresearch and consisted of extensively adsorbed, multiple-labeling grade donkey anti-rabbit-specific IgG conjugated to CY3 (diluted 1:1000) and donkey anti-mouse-specific IgG conjugated to either CY5 (diluted 1:500) or FITC (diluted 1:250). Nuclei were counterstained with YO-PRO1 (Molecular Probes, Inc.) diluted 1:500 for 20 minutes following immunostaining. Double-immunolabeling studies were carried out with all the necessary controls for staining specificity as outlined previously (Jetton et al., 1994, *J. Biol. Chem.* 269, 3641–3654). Following immunostaining, sections were mounted in Aqua-Polymount (Polysciences) and imaged using a Zeiss LSM 410 confocal microscope using the 488/647 and 543 nm lines of an Ar—Kr and He—Ne laser, respectively. Images were optimized using Adobe Photoshop 3.0 then transferred as TIFF files to a Silicon Graphics Indigo where figures were assembled using SGI Showcase and printed using a Tektronix Phaser IISDX color printer.

Glycosylation Analysis

Glycosylation analysis was performed on aliquots of HMEC membrane fractions with the Enzymatic Deglycosylation Kit from Glyko, Inc. according to the manufacturer's recommended protocol, and the samples were immunoblotted and probed with C-20 antibody.

Isolation of Secretory Vesicles

Secretory vesicles were isolated as described (Tooze and Huttner, 1990, Cell 60, 837–847) with minor modifications. All steps were performed at 4° C. MDA-MB-468 cells were washed with cold PBS containing protease inhibitors. After centrifugation at 700x g for 5 min, the pellet was resuspended in homogenization buffer (0.25 M sucrose, 1 mM EDTA, 1 mM Mg acetate, 10 mM HEPES-KOH, pH 7.2) with protease inhibitors and centrifuged at 1700x g for 5 min. The pellet was resuspended in 5 times the cell volume of homogenization buffer with protease inhibitors. Cells were passed through a 22 gauge needle 10 times and homogenized with 50 strokes of a Pyrex homogenizer. Unbroken cells and nuclei were pelleted at 1000x g for 10 min. One ml of the postnuclear supernatant was loaded onto a 0.3 M-1.2 M sucrose gradient (made in 10 mM HEPES-KOH, pH 7.2) with protease inhibitors and centrifuged at 25,000 rpm in a Beckman SW41 rotor for 15 min. One ml fractions were collected from the bottom and fractions 9–12 were pooled and loaded onto a 0.5 M-2 M sucrose gradient. The gradient was centrifuged at 25,000 rpm in a Beckman SW41 rotor for 16 hours and fractions collected from the bottom. Fractions 4–12 were analyzed by Western blot analysis.

Expression of Recombinant Clones in the Baculovirus Expression System

A full length BRCA1 cDNA containing consensus translation initiation and stop sites was cloned into the baculovirus transfer vector pAcSG2 as a Sal I fragment. Recombinant baculovirus were produced by cotransfecting Sf9 cells with Baculogold (PharMingen) virus DNA and the recombinant vector DNA. The resulting culture supernatants were harvested after four days, screened for homologous recombination by limiting dilution (Jensen et al., 1992, Biochem. 31: 10887–10892), and confirmed by dot-blot hybridization using the 32P-labeled, BRCA1 cDNA probe. Recombinant protein was expressed by infecting with high titer virus at multiplicities of infection of 10:1 or greater.

Peptide Mapping

Whole cell lysates from MDA-MB-468 cells and BRCA1 recombinant virus infected Sf9 cells were electrophoresed and the 190 kDa MDA-MB-468 band and 180 kDa BRCA1 recombinant protein were identified by removing one lane for immunoblotting with C-20 antibody. The bands of interest were then cut out of the gel, eluted on Microcon spin columns (Amicon), and digested with increasing amounts of V8 protease. The digests were re-electrophoresed on 4–20% gradient gels and immunoblotted with C-20.

Immunogold electron microscopy

MDA-MB-468 cells were trypsinized, washed in PBS, and fixed in 4.0% paraformaldehyde+0.1% glutaraldehyde/PBS (pH 7.4) for 10 minutes on ice. The cell pellet was washed in PBS, dehydrated in a graded series of alcohols, and embedded in LR White resin (medium grade; Polysciences, Inc.). Thin sections were mounted on nickel grids and blocked in PBS+1.0% bovine serum albumin (BSA) for two hours at room temperature. The grids were then incubated overnight in 1.0% BSA supplemented with 0.05% Tween with or without the C-20 antibody at a final dilution of 1:200. The grids were then washed in PBS/0.05% Tween and incubated in a 1:100 dilution of a goat anti-rabbit-gold conjugate (15 nm size; Electron Microscopy Sciences) for one hour at room temperature. The grids were washed as above, rinsed in distilled water and lightly counterstained with saturated aqueous uranyl acetate and lead citrate, and imaged with a Hitachi H-800 transmission electron microscope.

Gene Transfer Methods and Nude Mice Studies

MCF-7 cells were transfected by calcium phosphate coprecipitation for cell growth studies, but were transduced with retroviral stocks from PA317 producer clones for the nude mice studies as described in the results. Cultured MCF-7 cells were transduced in vitro and then injected subcutaneously into the left flank of 4 week old female nu/nu mice containing slow-release estrogen pellets (Soule et al., 1980, Cancer Letters 10, 177–189). Tumor size was determined weekly and animals were autopsied at 8 weeks after injection for determination of tumor weight and RT-PCR analysis for gene expression (Thompson et al., 1995, Nature Genetics 9, 444–450). For evaluation of effects of BRCA1 and mutant retroviral vectors on established tumors, $10^7$ MCF-7 cells were injected intraperitoneally and the animals were injected intraperitoneally with high titer retroviral vector stock ($10^7$ virions) once palpable tumors were identified.

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 5712
      (B) TYPE: nucleic acid
      (C) STRANDEDNESS: double
      (D) TOPOLOGY: linear (ii) MOLECULE TYPE: cDNA to mRNA (iii) HYPOTHETICAL: no (iv) ANTI-SENSE: no (v) ORIGINAL SOURCE:
        (A) ORGANISM: Homo sapiens
        (C) INDIVIDUAL ISOLATE:
        (D) DEVELOPMENTAL STAGE: adult
        (F) TISSUE TYPE: female breast
        (G) CELL TYPE: ductal carcinoma in situ, invasive
            breast cancer and normal breast tissue
        (H) CELL LINE: not derived from a cell line
        (I) ORGANELLE: no (vii) IMMEDIATE SOURCE:
        (A) LIBRARY: cDNA library derived from human
        (B) CLONE: obtained using published sequence (viii) POSITION IN GENOME:
        (A) CHROMOSOME/SEGMENT: unknown
        (B) MAP POSITION: unknown
        (C) UNITS: unknown (ix) FEATURE:
        (A) NAME/KEY: BRCA1
        (B) LOCATION: GenBank accession no. U14680
        (C) IDENTIFICATION METHOD: microscopicallydirected
            sampling and nuclease protection assay
        (D) OTHER INFORMATION: gene encoding BRCA1 protein (x) PUBLICATION INFORMATION:
        (A) AUTHORS: Miki, Y., et. al.
        (B) TITLE: A strong candidate gene for the breast and
            ovarian cancer susceptibility gene BRCA1.
        (C) JOURNAL: Science
        (D) VOLUME: 266
        (E) PAGES: 66-71
        (F) DATE: 1994
        (K) RELEVANT RESIDUES IN SEQ ID NO:1:

(xi) SEQUENCE DESCRIPTION: SEQ ID NO:1:

agctcgctga gacttcctgg accccgcacc aggctgtggg gtttctcaga taactgggcc      60
cctgcgctca ggaggccttc accctctgct ctgggtaaag ttcattggaa cagaaagaa     119 atg gat tta tct gct ctt cgc gtt gaa gaa gta caa aat gtc att aat      167
Met Asp Leu Ser Ala Leu Arg Val Glu Glu Val Gln Asn Val Ile Asn
 1               5                  10                  15 gct atg cag aaa atc tta gag tgt ccc atc tgt ctg gag ttg atc aag      215
Ala Met Gln Lys Ile Leu Glu Cys Pro Ile Cys Leu Glu Leu Ile Lys
                20                  25                  30 gaa cct gtc tcc aca aag tgt gac cac ata ttt tgc aaa ttt tgc atg      263
Glu Pro Val Ser Thr Lys Cys Asp His Ile Phe Cys Lys Phe Cys Met
            35                  40                  45 ctg aaa ctt ctc aac cag aag aaa ggg cct tca cag tgt cct tta tgt      311
Leu Lys Leu Leu Asn Gln Lys Lys Gly Pro Ser Gln Cys Pro Leu Cys
 50                  55                  60 aag aat gat ata acc aaa agg agc cta caa gaa agt acg aga ttt agt      359
Lys Asn Asp Ile Thr Lys Arg Ser Leu Gln Glu Ser Thr Arg Phe Ser
 65                  70                  75                  80 caa ctt gtt gaa gag cta ttg aaa atc att tgt gct ttt cag ctt gac      407
Gln Leu Val Glu Glu Leu Leu Lys Ile Ile Cys Ala Phe Gln Leu Asp
                85                  90                  95 aca ggt ttg gag tat gca aac agc tat aat ttt gca aaa aag gaa aat      455
Thr Gly Leu Glu Tyr Ala Asn Ser Tyr Asn Phe Ala Lys Lys Glu Asn
                100                 105                 110 aac tct cct gaa cat cta aaa gat gaa gtt tct atc atc caa agt atg      503
Asn Ser Pro Glu His Leu Lys Asp Glu Val Ser Ile Ile Gln Ser Met
            115                 120                 125

-continued

| | |
|---|---|
| ggc tac aga aac cgt gcc aaa aga ctt cta cag agt gaa ccc gaa aat<br>Gly Tyr Arg Asn Arg Ala Lys Arg Leu Leu Gln Ser Glu Pro Glu Asn<br>130                        135                     140 | 551 |
| cct tcc ttg cag gaa acc agt ctc agt gtc caa ctc tct aac ctt gga<br>Pro Ser Leu Gln Glu Thr Ser Leu Ser Val Gln Leu Ser Asn Leu Gly<br>145                        150                     155                  160 | 599 |
| act gtg aga act ctg agg aca aag cag cgg ata caa cct caa aag acg<br>Thr Val Arg Thr Leu Arg Thr Lys Gln Arg Ile Gln Pro Gln Lys Thr<br>                        165                     170                     175 | 647 |
| tct gtc tac att gaa ttg gga tct gat tct tct gaa gat acc gtt aat<br>Ser Val Tyr Ile Glu Leu Gly Ser Asp Ser Ser Glu Asp Thr Val Asn<br>                        180                     185                     190 | 695 |
| aag gca act tat tgc agt gtg gga gat caa gaa ttg tta caa atc acc<br>Lys Ala Thr Tyr Cys Ser Val Gly Asp Gln Glu Leu Leu Gln Ile Thr<br>           195                     200                     205 | 743 |
| cct caa gga acc agg gat gaa atc agt ttg gat tct gca aaa aag gct<br>Pro Gln Gly Thr Arg Asp Glu Ile Ser Leu Asp Ser Ala Lys Lys Ala<br>210                        215                     220 | 791 |
| gct tgt gaa ttt tct gag acg gat gta aca aat act gaa cat cat caa<br>Ala Cys Glu Phe Ser Glu Thr Asp Val Thr Asn Thr Glu His His Gln<br>225                        230                     235                  240 | 839 |
| ccc agt aat aat gat ttg aac acc act gag aag cgt gca gct gag agg<br>Pro Ser Asn Asn Asp Leu Asn Thr Thr Glu Lys Arg Ala Ala Glu Arg<br>                        245                     250                     255 | 887 |
| cat cca gaa aag tat cag ggt agt tct gtt tca aac ttg cat gtg gag<br>His Pro Glu Lys Tyr Gln Gly Ser Ser Val Ser Asn Leu His Val Glu<br>                        260                     265                     270 | 935 |
| cca tgt ggc aca aat act cat gcc agc tca tta cag cat gag aac agc<br>Pro Cys Gly Thr Asn Thr His Ala Ser Ser Leu Gln His Glu Asn Ser<br>           275                     280                     285 | 983 |
| agt tta tta ctc act aaa gac aga atg aat gta gaa aag gct gaa ttc<br>Ser Leu Leu Leu Thr Lys Asp Arg Met Asn Val Glu Lys Ala Glu Phe<br>290                        295                     300 | 1031 |
| tgt aat aaa agc aaa cag cct ggc tta gca agg agc caa cat aac aga<br>Cys Asn Lys Ser Lys Gln Pro Gly Leu Ala Arg Ser Gln His Asn Arg<br>305                        310                     315                     320 | 1079 |
| tgg gct gga agt aag gaa aca tgt aat gat agg cgg act ccc agc aca<br>Trp Ala Gly Ser Lys Glu Thr Cys Asn Asp Arg Arg Thr Pro Ser Thr<br>                        325                     330                     335 | 1127 |
| gaa aaa aag gta gat ctg aat gct gat ccc ctg tgt gag aga aaa gaa<br>Glu Lys Lys Val Asp Leu Asn Ala Asp Pro Leu Cys Glu Arg Lys Glu<br>                        340                     345                     350 | 1175 |
| tgg aat aag cag aaa ctg cca tgc tca gag aat cct aga gat act gaa<br>Trp Asn Lys Gln Lys Leu Pro Cys Ser Glu Asn Pro Arg Asp Thr Glu<br>           355                     360                     365 | 1223 |
| gat gtt cct tgg ata aca cta aat agc agc att cag aaa gtt aat gag<br>Asp Val Pro Trp Ile Thr Leu Asn Ser Ser Ile Gln Lys Val Asn Glu<br>370                        375                     380 | 1271 |
| tgg ttt tcc aga agt gat gaa ctg tta ggt tct gat gac tca cat gat<br>Trp Phe Ser Arg Ser Asp Glu Leu Leu Gly Ser Asp Asp Ser His Asp<br>385                        390                     395                  400 | 1319 |
| ggg gag tct gaa tca aat gcc aaa gta gct gat gta ttg gac gtt cta<br>Gly Glu Ser Glu Ser Asn Ala Lys Val Ala Asp Val Leu Asp Val Leu<br>                        405                     410                     415 | 1367 |
| aat gag gta gat gaa tat tct ggt tct tca gag aaa ata gac tta ctg<br>Asn Glu Val Asp Glu Tyr Ser Gly Ser Ser Glu Lys Ile Asp Leu Leu<br>                        420                     425                     430 | 1415 |
| gcc agt gat cct cat gag gct tta ata tgt aaa agt gaa aga gtt cac<br>Ala Ser Asp Pro His Glu Ala Leu Ile Cys Lys Ser Glu Arg Val His<br>           435                     440                     445 | 1463 |

-continued

```
tcc aaa tca gta gag agt aat att gaa gac aaa ata ttt ggg aaa acc      1511
Ser Lys Ser Val Glu Ser Asn Ile Glu Asp Lys Ile Phe Gly Lys Thr
    450                 455                 460 tat cgg aag aag gca agc ctc ccc aac tta agc cat gta act gaa aat      1559
Tyr Arg Lys Lys Ala Ser Leu Pro Asn Leu Ser His Val Thr Glu Asn
465                 470                 475                 480 cta att ata gga gca ttt gtt act gag cca cag ata ata caa gag cgt      1607
Leu Ile Ile Gly Ala Phe Val Ser Glu Pro Gln Ile Ile Gln Glu Arg
                485                 490                 495 ccc ctc aca aat aaa tta aag cgt aaa agg aga cct aca tca ggc ctt      1655
Pro Leu Thr Asn Lys Leu Lys Arg Lys Arg Arg Pro Thr Ser Gly Leu
            500                 505                 510 cat cct gag gat ttt atc aag aaa gca gat ttg gca gtt caa aag act      1703
His Pro Glu Asp Phe Ile Lys Lys Ala Asp Leu Ala Val Gln Lys Thr
        515                 520                 525 cct gaa atg ata aat cag gga act aac caa acg gag cag aat ggt caa      1751
Pro Glu Met Ile Asn Gln Gly Thr Asn Gln Thr Glu Gln Asn Gly Gln
    530                 535                 540 gtg atg aat att act aat agt ggt cat gag aat aaa aca aaa ggt gat      1799
Val Met Asn Ile Thr Asn Ser Gly His Glu Asn Lys Thr Lys Gly Asp
545                 550                 555                 560 tct att cag aat gag aaa aat cct aac cca ata gaa tca ctc gaa aaa      1847
Ser Ile Gln Asn Glu Lys Asn Pro Asn Pro Ile Glu Ser Leu Glu Lys
                565                 570                 575 gaa tct gct ttc aaa acg aaa gct gaa cct ata agc agc agt ata agc      1895
Glu Ser Ala Phe Lys Thr Lys Ala Glu Pro Ile Ser Ser Ser Ile Ser
                580                 585                 590 aat atg gaa ctc gaa tta aat atc cac aat tca aaa gca cct aaa aag      1943
Asn Met Glu Leu Glu Leu Asn Ile His Asn Ser Lys Ala Pro Lys Lys
            595                 600                 605 aat agg ctg agg agg aag tct tct acc agg cat att cat gcg ctt gaa      1991
Asn Arg Leu Arg Arg Lys Ser Ser Thr Arg His Ile His Ala Leu Glu
        610                 615                 620 cta gta gtc agt aga aat cta agc cca cct aat tgt act gaa ttg caa      2039
Leu Val Val Ser Arg Asn Leu Ser Pro Pro Asn Cys Thr Glu Leu Gln
625                 630                 635                 640 att gat agt tgt tct agc agt gaa gag ata aag aaa aaa aag tac aac      2087
Ile Asp Ser Cys Ser Ser Ser Glu Glu Ile Lys Lys Lys Lys Tyr Asn
                645                 650                 655 caa atg cca gtc agg cac agc aga aac cta caa ctc atg gaa ggt aaa      2135
Gln Met Pro Val Arg His Ser Arg Asn Leu Gln Leu Met Glu Gly Lys
            660                 665                 670 gaa cct gca act gga gcc aag aag agt aac aag cca aat gaa cag aca      2183
Glu Pro Ala Thr Gly Ala Lys Lys Ser Asn Lys Pro Asn Glu Gln Thr
        675                 680                 685 agt aaa aga cat gac agc gat act ttc cca gag ctg aag tta aca aat      2231
Ser Lys Arg His Asp Ser Asp Thr Phe Pro Glu Leu Lys Leu Thr Asn
    690                 695                 700 gca cct ggt tct ttt act aag tgt tca aat acc agt gaa ctt aaa gaa      2279
Ala Pro Gly Ser Phe Thr Lys Cys Ser Asn Thr Ser Glu Leu Lys Glu
705                 710                 715                 720 ttt gtc aat cct agc ctt cca aga gaa gaa aaa gaa gag aaa cta gaa      2327
Phe Val Asn Pro Ser Leu Pro Arg Glu Glu Lys Glu Glu Lys Leu Glu
                725                 730                 735 aca gtt aaa gtg tct aat aat gct gaa gac ccc aaa gat ctc atg tta      2375
Thr Val Lys Val Ser Asn Asn Ala Glu Asp Pro Lys Asp Leu Met Leu
            740                 745                 750 agt gga gaa agg gtt ttg caa act gaa aga tct gta gag agt agc agt      2423
Ser Gly Glu Arg Val Leu Gln Thr Glu Arg Ser Val Glu Ser Ser Ser
```

```
                    755                 760                 765
att tca ttg gta cct ggt act gat tat ggc act cag gaa agt atc tcg        2471
Ile Ser Leu Val Pro Gly Thr Asp Tyr Gly Thr Gln Glu Ser Ile Ser
        770                 775                 780 tta ctg gaa gtt agc act cta ggg aag gca aaa aca gaa cca aat aaa        2519
Leu Leu Glu Val Ser Thr Leu Gly Lys Ala Lys Thr Glu Pro Asn Lys
785                 790                 795                 800 tgt gtg agt cag tgt gca gca ttt gaa aac ccc aag gga cta att cat        2567
Cys Val Ser Gln Cys Ala Ala Phe Glu Asn Pro Lys Gly Leu Ile His
                805                 810                 815 ggt tgt tcc aaa gat aat aga aat gac aca gaa ggc ttt aag tat cca        2615
Gly Cys Ser Lys Asp Asn Arg Asn Asp Thr Glu Gly Phe Lys Tyr Pro
                820                 825                 830 ttg gga cat gaa gtt aac cac agt cgg gaa aca agc ata gaa atg gaa        2663
Leu Gly His Glu Val Asn His Ser Arg Glu Thr Ser Ile Glu Met Glu
        835                 840                 845 gaa agt gaa ctt gat gct cag tat ttg cag aat aca ttc aag gtt tca        2711
Glu Ser Glu Leu Asp Ala Gln Tyr Leu Gln Asn Thr Phe Lys Val Ser
        850                 855                 860 aag cgc cag tca ttt gct ccg ttt tca aat cca gga aat gca gaa gag        2759
Lys Arg Gln Ser Phe Ala Pro Phe Ser Asn Pro Gly Asn Ala Glu Glu
865                 870                 875                 880 gaa tgt gca aca ttc tct gcc cac tct ggg tcc tta aag aaa caa agt        2807
Glu Cys Ala Thr Phe Ser Ala His Ser Gly Ser Leu Lys Lys Gln Ser
                885                 890                 895 cca aaa gtc act ttt gaa tgt gaa caa aag gaa gaa aat caa gga aag        2855
Pro Lys Val Thr Phe Glu Cys Glu Gln Lys Glu Glu Asn Gln Gly Lys
                900                 905                 910 aat gag tct aat atc aag cct gta cag aca gtt aat atc act gca ggc        2903
Asn Glu Ser Asn Ile Lys Pro Val Gln Thr Val Asn Ile Thr Ala Gly
        915                 920                 925 ttt cct gtg gtt ggt cag aaa gat aag cca gtt gat aat gcc aaa tgt        2951
Phe Pro Val Val Gly Gln Lys Asp Lys Pro Val Asp Asn Ala Lys Cys
        930                 935                 940 agt atc aaa gga ggc tct agg ttt tgt cta tca tct cag ttc aga ggc        2999
Ser Ile Lys Gly Gly Ser Arg Phe Cys Leu Ser Ser Gln Phe Arg Gly
945                 950                 955                 960 aac gaa act gga ctc att act cca aat aaa cat gga ctt tta caa aac        3047
Asn Glu Thr Gly Leu Ile Thr Pro Asn Lys His Gly Leu Leu Gln Asn
                965                 970                 975 cca tat cgt ata cca cca ctt ttt ccc atc aag tca ttt gtt aaa act        3095
Pro Tyr Arg Ile Pro Pro Leu Phe Pro Ile Lys Ser Phe Val Lys Thr
                980                 985                 990 aaa tgt aag aaa aat ctg cta gag gaa aac ttt gag gaa cat tca atg        3143
Lys Cys Lys Lys Asn Leu Leu Glu Glu Asn Phe Glu Glu His Ser Met
        995                 1000                1005 tca cct gaa aga gaa atg gga aat gag aac att cca agt aca gtg agc        3191
Ser Pro Glu Arg Glu Met Gly Asn Glu Asn Ile Pro Ser Thr Val Ser
        1010                1015                1020 aca att agc cgt aat aac att aga gaa aat gtt ttt aaa gaa gcc agc        3239
Thr Ile Ser Arg Asn Asn Ile Arg Glu Asn Val Phe Lys Glu Ala Ser
1025                1030                1035                1040 tca agc aat att aat gaa gta ggt tcc agt act aat gaa gtg ggc tcc        3287
Ser Ser Asn Ile Asn Glu Val Gly Ser Ser Thr Asn Glu Val Gly Ser
                1045                1050                1055 agt att aat gaa ata ggt tcc agt gat gaa aac att caa gca gaa cta        3335
Ser Ile Asn Glu Ile Gly Ser Ser Asp Glu Asn Ile Gln Ala Glu Leu
        1060                1065                1070 ggt aga aac aga ggg cca aaa ttg aat gct atg ctt aga tta ggg gtt        3383
```

-continued

```
Gly Arg Asn Arg Gly Pro Lys Leu Asn Ala Met Leu Arg Leu Gly Val
        1075                1080                1085 ttg caa cct gag gtc tat aaa caa agt ctt cct gga agt aat tgt aag        3431
Leu Gln Pro Glu Val Tyr Lys Gln Ser Leu Pro Gly Ser Asn Cys Lys
    1090                1095                1100 cat cct gaa ata aaa aag caa gaa tat gaa gaa gta gtt cag act gtt        3479
His Pro Glu Ile Lys Lys Gln Glu Tyr Glu Glu Val Val Gln Thr Val
1105                1110                1115                1120 aat aca gat ttc tct cca tat ctg att tca gat aac tta gaa cag cct        3527
Asn Thr Asp Phe Ser Pro Tyr Leu Ile Ser Asp Asn Leu Glu Gln Pro
                1125                1130                1135 atg gga agt agt cat gca tct cag gtt tgt tct gag aca cct gat gac        3575
Met Gly Ser Ser His Ala Ser Gln Val Cys Ser Glu Thr Pro Asp Asp
            1140                1145                1150 ctg tta gat gat ggt gaa ata aag gaa gat act agt ttt gct gaa aat        3623
Leu Leu Asp Asp Gly Glu Ile Lys Glu Asp Thr Ser Phe Ala Glu Asn
        1155                1160                1165 gac att aag gaa agt tct gct gtt ttt agc aaa agc gtc cag aaa gga        3671
Asp Ile Lys Glu Ser Ser Ala Val Phe Ser Lys Ser Val Gln Lys Gly
    1170                1175                1180 gag ctt agc agg agt cct agc cct ttc acc cat aca cat ttg gct cag        3719
Glu Leu Ser Arg Ser Pro Ser Pro Phe Thr His Thr His Leu Ala Gln
1185                1190                1195                1200 ggt tac cga aga ggg gcc aag aaa tta gag tcc tca gaa gag aac tta        3767
Gly Tyr Arg Arg Gly Ala Lys Lys Leu Glu Ser Ser Glu Glu Asn Leu
                1205                1210                1215 tct agt gag gat gaa gag ctt ccc tgc ttc caa cac ttg tta ttt ggt        3815
Ser Ser Glu Asp Glu Glu Leu Pro Cys Phe Gln His Leu Leu Phe Gly
            1220                1225                1230 aaa gta aac aat ata cct tct cag tct act agg cat agc acc gtt gct        3863
Lys Val Asn Asn Ile Pro Ser Gln Ser Thr Arg His Ser Thr Val Ala
        1235                1240                1245 acc gag tgt ctg tct aag aac aca gag gag aat tta tta tca ttg aag        3911
Thr Glu Cys Leu Ser Lys Asn Thr Glu Glu Asn Leu Leu Ser Leu Lys
    1250                1255                1260 aat agc tta aat gac tgc agt aac cag gta ata ttg gca aag gca tct        3959
Asn Ser Leu Asn Asp Cys Ser Asn Gln Val Ile Leu Ala Lys Ala Ser
1265                1270                1275                1280 cag gaa cat cac ctt agt gag gaa aca aaa tgt tct gct agc ttg ttt        4007
Gln Glu His His Leu Ser Glu Glu Thr Lys Cys Ser Ala Ser Leu Phe
                1285                1290                1295 tct tca cag tgc agt gaa ttg gaa gac ttg act gca aat aca aac acc        4055
Ser Ser Gln Cys Ser Glu Leu Glu Asp Leu Thr Ala Asn Thr Asn Thr
            1300                1305                1310 cag gat cct ttc ttg att ggt tct tcc aaa caa atg agg cat cag tct        4103
Gln Asp Pro Phe Leu Ile Gly Ser Ser Lys Gln Met Arg His Gln Ser
        1315                1320                1325 gaa agc cag gga gtt ggt ctg agt gac aag gaa ttg gtt tca gat gat        4151
Glu Ser Gln Gly Val Gly Leu Ser Asp Lys Glu Leu Val Ser Asp Asp
    1330                1335                1340 gaa gaa aga gga acg ggc ttg gaa gaa aat aat caa gaa gag caa agc        4199
Glu Glu Arg Gly Thr Gly Leu Glu Glu Asn Asn Gln Glu Glu Gln Ser
1345                1350                1355                1360 atg gat tca aac tta ggt gaa gca gca tct ggg tgt gag agt gaa aca        4247
Met Asp Ser Asn Leu Gly Glu Ala Ala Ser Gly Cys Glu Ser Glu Thr
                1365                1370                1375 agc gtc tct gaa gac tgc tca ggg cta tcc tct cag agt gac att tta        4295
Ser Val Ser Glu Asp Cys Ser Gly Leu Ser Ser Gln Ser Asp Ile Leu
            1380                1385                1390
```

```
acc act cag cag agg gat acc atg caa cat aac ctg ata aag ctc cag        4343
Thr Thr Gln Gln Arg Asp Thr Met Gln His Asn Leu Ile Lys Leu Gln
        1395                1400                1405 cag gaa atg gct gaa cta gaa gct gtg tta gaa cag cat ggg agc cag        4391
Gln Glu Met Ala Glu Leu Glu Ala Val Leu Glu Gln His Gly Ser Gln
    1410                1415                1420 cct tct aac agc tac cct tcc atc ata agt gac tct tct gcc ctt gag        4439
Pro Ser Asn Ser Tyr Pro Ser Ile Ile Ser Asp Ser Ser Ala Leu Glu
1425                1430                1435                1440 gac ctg cga aat cca gaa caa agc aca tca gaa aaa gca gta tta act        4487
Asp Leu Arg Asn Pro Glu Gln Ser Thr Ser Glu Lys Ala Val Leu Thr
                1445                1450                1455 tca cag aaa agt agt gaa tac cct ata agc cag aat cca gaa ggc ctt        4535
Ser Gln Lys Ser Ser Glu Tyr Pro Ile Ser Gln Asn Pro Glu Gly Xaa
            1460                1465                1470 tct gct gac aag ttt gag gtg tct gca gat agt tct acc agt aaa aat        4583
Ser Ala Asp Lys Phe Glu Val Ser Ala Asp Ser Ser Thr Ser Lys Asn
        1475                1480                1485 aaa gaa cca gga gtg gaa agg tca tcc cct tct aaa tgc cca tca tta        4631
Lys Glu Pro Gly Val Glu Arg Ser Ser Pro Ser Lys Cys Pro Ser Leu
    1490                1495                1500 gat gat agg tgg tac atg cac agt tgc tct ggg agt ctt cag aat aga        4679
Asp Asp Arg Trp Tyr Met His Ser Cys Ser Gly Ser Leu Gln Asn Arg
1505                1510                1515                1520 aac tac cca tct caa gag gag ctc att aag gtt gtt gat gtg gag gag        4727
Asn Tyr Pro Ser Gln Glu Glu Leu Ile Lys Val Val Asp Val Glu Glu
                1525                1530                1535 caa cag ctg gaa gag tct ggg cca cac gat ttg acg gaa aca tct tac        4775
Gln Gln Leu Glu Glu Ser Gly Pro His Asp Leu Thr Glu Thr Ser Tyr
            1540                1545                1550 ttg cca agg caa gat cta gag gga acc cct tac ctg gaa tct gga atc        4823
Leu Pro Arg Gln Asp Leu Glu Gly Thr Pro Tyr Leu Glu Ser Gly Ile
        1555                1560                1565 agc ctc ttc tct gat gac cct gaa tct gat cct tct gaa gac aga gcc        4871
Ser Leu Phe Ser Asp Asp Pro Glu Ser Asp Pro Ser Glu Asp Arg Ala
    1570                1575                1580 cca gag tca gct cgt gtt ggc aac ata cca tct tca acc tct gca ttg        4919
Pro Glu Ser Ala Arg Val Gly Asn Ile Pro Ser Ser Thr Ser Ala Leu
1585                1590                1595                1600 aaa gtt ccc caa ttg aaa gtt gca gaa tct gcc cag agt cca gct gct        4967
Lys Val Pro Gln Leu Lys Val Ala Glu Ser Ala Gln Ser Pro Ala Ala
                1605                1610                1615 gct cat act act gat act gct ggg tat aat gca atg gaa gaa agt gtg        5015
Ala His Thr Thr Asp Thr Ala Gly Tyr Asn Ala Met Glu Glu Ser Val
            1620                1625                1630 agc agg gag aag cca gaa ttg aca gct tca aca gaa agg gtc aac aaa        5063
Ser Arg Glu Lys Pro Glu Leu Thr Ala Ser Thr Glu Arg Val Asn Lys
        1635                1640                1645 aga atg tcc atg gtg gtg tct ggc ctg acc cca gaa gaa ttt atg ctc        5111
Arg Met Ser Met Val Val Ser Gly Leu Thr Pro Glu Glu Phe Met Leu
    1650                1655                1660 gtg tac aag ttt gcc aga aaa cac cac atc act tta act aat cta att        5159
Val Tyr Lys Phe Ala Arg Lys His His Ile Thr Leu Thr Asn Leu Ile
1665                1670                1675                1680 act gaa gag act act cat gtt gtt atg aaa aca gat gct gag ttt gtg        5207
Thr Glu Glu Thr Thr His Val Val Met Lys Thr Asp Ala Glu Phe Val
                1685                1690                1695 tgt gaa cgg aca ctg aaa tat ttt cta gga att gcg gga gga aaa tgg        5255
Cys Glu Arg Thr Leu Lys Tyr Phe Leu Gly Ile Ala Gly Gly Lys Trp
            1700                1705                1710
```

```
gta gtt agc tat ttc tgg gtg acc cag tct att aaa gaa aga aaa atg      5303
Val Val Ser Tyr Phe Trp Val Thr Gln Ser Ile Lys Glu Arg Lys Met
        1715                1720                1725 ctg aat gag cat gat ttt gaa gtc aga gga gat gtg gtc aat gga aga      5351
Leu Asn Glu His Asp Phe Glu Val Arg Gly Asp Val Val Asn Gly Arg
1730                1735                1740 aac cac caa ggt cca aag cga gca aga gaa tcc cag gac aga aag atc      5399
Asn His Gln Gly Pro Lys Arg Ala Arg Glu Ser Gln Asp Arg Lys Ile
1745                1750                1755                1760 ttc agg ggg cta gaa atc tgt tgc tat ggg ccc ttc acc aac atg ccc      5447
Phe Arg Gly Leu Glu Ile Cys Cys Tyr Gly Pro Phe Thr Asn Met Pro
            1765                1770                1775 aca gat caa ctg gaa tgg atg gta cag ctg tgt ggt gct tct gtg gtg      5495
Thr Asp Gln Leu Glu Trp Met Val Gln Leu Cys Gly Ala Ser Val Val
        1780                1785                1790 aag gag ctt tca tca ttc acc ctt ggc aca ggt gtc cac cca att gtg      5543
Lys Glu Leu Ser Ser Phe Thr Leu Gly Thr Gly Val His Pro Ile Val
        1795                1800                1805 gtt gtg cag cca gat gcc tgg aca gag gac aat ggc ttc cat gca att      5591
Val Val Gln Pro Asp Ala Trp Thr Glu Asp Asn Gly Phe His Ala Ile
    1810                1815                1820 ggg cag atg tgt gag gca cct gtg gtg acc cga gag tgg gtg ttg gac      5639
Gly Gln Met Cys Glu Ala Pro Val Val Thr Arg Glu Trp Val Leu Asp
1825                1830                1835                1840 agt gta gca ctc tac cag tgc cag gag ctg gac acc tac ctg ata ccc      5687
Ser Val Ala Leu Tyr Gln Cys Gln Glu Leu Asp Thr Tyr Leu Ile Pro
            1845                1850                1855 cag atc ccc cac agc cac tac tgat                                     5712
Gln Ile Pro His Ser His Tyr
            1860
```

(2) INFORMATION FOR SEQ ID NO:2:

(i) SEQUENCE CHARACTERISTICS:
        (A) LENGTH: 1863
        (B) TYPE: amino acid
        (C) STRANDEDNESS: single
        (D) TOPOLOGY: unknown (ii) MOLECULE TYPE: protein (iii) HYPOTHETICAL: no (iv) ANTI-SENSE: no (v) ORIGINAL SOURCE:
        (A) ORGANISM: Homo sapiens
        (C) INDIVIDUAL ISOLATE:
        (D) DEVELOPMENTAL STAGE: adult
        (F) TISSUE TYPE: female breast
        (G) CELL TYPE: ductal carcinoma in situ, invasive
            breast cancer and normal breast tissue
        (H) CELL LINE: not derived from a cell line
        (I) ORGANELLE: no (vii) IMMEDIATE SOURCE:
        (A) LIBRARY: cDNA library derived from human
        (B) CLONE: obtained using published sequence (viii) POSITION IN GENOME:
        (A) CHROMOSOME/SEGMENT: unknown
        (B) MAP POSITION: unknown
        (C) UNITS: unknown (ix) FEATURE:
        (A) NAME/KEY: BRCA1 protein
        (B) LOCATION: 1 to 1863
        (C) IDENTIFICATION METHOD: observation of mRNA and antisense inhibition of BRCA1 gene
      (D) OTHER INFORMATION: BRCA1 protein has a negative
          regulatory effect on growth of human mammary cells.

(x) PUBLICATION INFORMATION:
      (A) AUTHORS: Miki, Y., et. al.
      (B) TITLE: A strong candidate gene for the breast and
          ovarian cancer susceptibility gene BRCA1.
      (C) JOURNAL: Science
      (D) VOLUME: 266
      (E) PAGES: 66-71
      (F) DATE: 1994
      (K) RELEVANT RESIDUES IN SEQ ID NO:2: granin box
          domain at amino acids 1214-1223

(xi) SEQUENCE DESCRIPTION: SEQ ID NO:2:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335
```

```
Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
            405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Asp Arg Val His
            435                 440                 445

Ser Lys Ser Val Glu Ser Asp Ile Glu Asp Lys Ile Phe Gly Lys Thr
            450                 455                 460

Tyr Arg Lys Lys Ala Ser Leu Pro Asn Leu Ser His Val Thr Glu Asn
465                 470                 475                 480

Leu Ile Ile Gly Ala Phe Val Ser Glu Pro Gln Ile Ile Gln Glu Arg
            485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
            565                 570                 575

Glu Ser Ala Phe Lys Thr Lys Ala Glu Pro Ile Ser Ser Ser Ile Ser
            580                 585                 590

Asn Glu Leu Glu Leu Asn Ile Met His Asn Ser Lys Ala Pro Lys Lys
            595                 600                 605

Asn Arg Leu Arg Arg Lys Ser Ser Thr Arg His Ile His Ala Leu Glu
            610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
            645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
            690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
            725                 730                 735

Thr Val Lys Val Ser Asn Asn Ala Glu Asp Pro Lys Asp Leu Met Leu
            740                 745                 750
```

-continued

```
Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
            770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
        850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val Ser
        1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
            1060                1065                1070

Gly Arg Asn Arg Gly Pro Lys Leu Asn Ala Met Leu Arg Leu Gly Val
            1075                1080                1085

Leu Gln Pro Glu Val Tyr Lys Gln Ser Leu Pro Gly Ser Asn Cys Lys
        1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
            1140                1145                1150

Leu Leu Asp Asp Gly Glu Ile Lys Glu Asp Thr Ser Phe Ala Glu Asn
            1155                1160                1165

Asp Ile Lys Glu Ser Ser Ala Val Phe Ser Lys Ser Val Gln Lys Gly
```

-continued

```
        1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
                1205                1210                1215
Ser Ser Glu Asp Glu Glu Leu Pro Cys Phe Gln His Leu Leu Phe Gly
            1220                1225                1230
Lys Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu Lys
    1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
                1285                1290                1295
Ser Ser Gln Cys Ser Glu Leu Glu Asp Leu Thr Ala Asn Thr Asn Thr
            1300                1305                1310
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
    1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
                1365                1370                1375
Ser Val Ser Glu Asp Cys Ser Gly Leu Ser Ser Gln Ser Asp Ile Leu
            1380                1385                1390
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
    1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Val Leu Gln Thr
                1445                1450                1455
Ser Gln Lys Ser Ser Glu Tyr Pro Ile Ser Gln Asn Pro Glu Gly Xaa
            1460                1465                1470
Ser Ala Asp Lys Phe Glu Val Ser Ala Asp Ser Ser Thr Ser Lys Asn
        1475                1480                1485
Lys Glu Pro Gly Val Glu Arg Ser Ser Pro Ser Lys Cys Pro Ser Leu
    1490                1495                1500
Asp Asp Arg Trp Tyr Met His Ser Cys Ser Gly Ser Leu Gln Asn Arg
1505                1510                1515                1520
Asn Tyr Pro Pro Gln Glu Glu Leu Ile Lys Val Val Asp Val Glu Glu
                1525                1530                1535
Gln Gln Leu Glu Glu Ser Gly Pro His Asp Leu Thr Glu Thr Ser Tyr
            1540                1545                1550
Leu Pro Arg Gln Asp Leu Glu Gly Thr Pro Tyr Leu Glu Ser Gly Ile
        1555                1560                1565
Ser Leu Phe Ser Asp Asp Pro Glu Ser Asp Pro Ser Glu Asp Arg Ala
    1570                1575                1580
Pro Glu Ser Ala Arg Val Gly Asn Ile Pro Ser Ser Thr Ser Ala Leu
1585                1590                1595                1600
```

```
Lys Val Pro Gln Leu Lys Val Ala Glu Ser Ala Gln Ser Pro Ala Ala
                1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Lys
            1635                1640                1645

Arg Met Ser Met Val Val Ser Gly Leu Thr Pro Glu Glu Phe Met Leu
        1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
        1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
            1715                1720                1725

Leu Asn Glu His Asp Phe Glu Val Arg Gly Asp Val Val Asn Gly Arg
            1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
            1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
            1795                1800                1805

Val Val Gln Pro Asp Ala Trp Thr Glu Asp Asn Gly Phe His Ala Ile
            1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
            1845                1850                1855

Gln Ile Pro His Ser His Tyr
            1860

(2) INFORMATION FOR SEQ ID NO:3:

(i) SEQUENCE CHARACTERISTICS:
        (A) LENGTH: 11283
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (v) ORIGINAL SOURCE:
        (A) ORGANISM: Homo sapiens sapiens
        (C) INDIVIDUAL ISOLATE:
        (D) DEVELOPMENTAL STAGE: adult
        (F) TISSUE TYPE: female breast
        (G) CELL TYPE: normal and cancerous breast cells
        (H) CELL LINE: MCF-7
        (I) ORGANELLE: no (vii) IMMEDIATE SOURCE:
        (A) LIBRARY: cDNA library derived from human
        (B) CLONE: obtained using published sequence
```

(viii) POSITION IN GENOME:
    (A) CHROMOSOME/SEGMENT: unknown
    (B) MAP POSITION: unknown
    (C) UNITS: unknown (ix) FEATURE:
    (A) NAME/KEY: BRCA2
    (B) LOCATION:
    (C) IDENTIFICATION METHOD:
    (D) OTHER INFORMATION: gene encoding BRCA2 protein (x) PUBLICATION INFORMATION:
    (A) AUTHORS:     Wooster, R. et al.
    (B) TITLE:  Identification of the breast cancer
         susceptability gene BRCA2
    (C) JOURNAL:     Nature
    (D) VOLUME:      379
    (E) PAGES:       789-792
    (F) DATE:        1995
    (K) RELEVANT RESIDUES IN SEQ ID NO:3

(xi) SEQUENCE DESCRIPTION:  SEQ ID NO:3:

```
ggcggagccg ctgtggcact gctgcgcctc tgctgcgcct cgggtgtctt ttgcggcggt      60
gggtcgccgc cgggagaagc gtgaggggac agatttgtga ccggcgcggt ttttgtcagc     120
ttactccggc caaaaaagaa ctgcacctct ggagcggact tatttaccaa gcattggagg     180
aatatcgtag gtaaaa                                                     196 atg cct att gga tcc aaa gag agg cca aca ttt ttt gaa att ttt aag       244
Met Pro Ile Gly Ser Lys Glu Arg Pro Thr Phe Phe Glu Ile Phe Lys
1               5                   10                  15 aca cgc tgc aac aaa gca gat tta gga cca ata agt ctt aat tgg ttt       292
Thr Arg Cys Asn Lys Ala Asp Leu Gly Pro Ile Ser Leu Asn Trp Phe
        20                  25                  30 gaa gaa ctt tct tca gaa gct cca ccc tat aat tct gaa cct gca gaa       340
Glu Glu Leu Ser Ser Glu Ala Pro Pro Tyr Asn Ser Glu Pro Ala Glu
35                  40                  45 gaa tct gaa cat aaa aac aac aat tac gaa cca aac cta ttt aaa act       388
Glu Ser Glu His Lys Asn Asn Asn Tyr Glu Pro Asn Leu Phe Lys Thr
50                  55                  60 cca caa agg aaa cca tct tat aat cag ctg gct tca act cca ata ata       436
Pro Gln Arg Lys Pro Ser Tyr Asn Gln Leu Ala Ser Thr Pro Ile Ile
65                  70                  75                  80 ttc aaa gag caa ggg ctg act ctg ccg ctg tac caa tct cct gta aaa       484
Phe Lys Glu Gln Gly Leu Thr Leu Pro Leu Tyr Gln Ser Pro Val Lys
85                  90                  95 gaa tta gat aaa ttc aaa tta gac tta gga agg aat gtt ccc aat agt       532
Glu Leu Asp Lys Phe Lys Leu Asp Leu Gly Arg Asn Val Pro Asn Ser
100                 105                 110 aga cat aaa agt ctt cgc aca gtg aaa act aaa atg gat caa gca gat       580
Arg His Lys Ser Leu Arg Thr Val Lys Thr Lys Met Asp Gln Ala Asp
115                 120                 125 gat gtt tcc tgt cca ctt cta aat tct tgt ctt agt gaa agt cct gtt       628
Asp Val Ser Cys Pro Leu Leu Asn Ser Cys Leu Ser Glu Ser Pro Val
130                 135                 140 gtt cta caa tgt aca cat gta aca cca caa aga gat aag tca gtg gta       676
Val Leu Gln Cys Thr His Val Thr Pro Gln Arg Asp Lys Ser Val Val
145                 150                 155                 160 tgt ggg agt ttg ttt cat aca cca aag ttt gtg aag ggt cgt cag aca       724
Cys Gly Ser Leu Phe His Thr Pro Lys Phe Val Lys Gly Arg Gln Thr
165                 170                 175 cca aaa cat att tct gaa agt cta gga gct gag gtg gat cct gat atg       772
Pro Lys His Ile Ser Glu Ser Leu Gly Ala Glu Val Asp Pro Asp Met
180                 185                 190
```

-continued

| | | | | | | | | | | | | | | | | |
|---|---|---|---|---|---|---|---|---|---|---|---|---|---|---|---|---|
| tct | tgg | tca | agt | tct | tta | gct | aca | cca | ccc | acc | ctt | agt | tct | act | gtg | 820 |
| Ser | Trp | Ser | Ser | Ser | Leu | Ala | Thr | Pro | Pro | Thr | Leu | Ser | Ser | Thr | Val | |
| 195 | | | | | 200 | | | | | 205 | | | | | | |
| ctc | ata | gtc | aga | aat | gaa | gaa | gca | tct | gaa | act | gta | ttt | cct | cat | gat | 868 |
| Leu | Ile | Val | Arg | Asn | Glu | Glu | Ala | Ser | Glu | Thr | Val | Phe | Pro | His | Asp | |
| 210 | | | | 215 | | | | | 220 | | | | | | | |
| act | act | gct | aat | gtg | aaa | agc | tat | ttt | tcc | aat | cat | gat | gaa | agt | ctg | 916 |
| Thr | Thr | Ala | Asn | Val | Lys | Ser | Tyr | Phe | Ser | Asn | His | Asp | Glu | Ser | Leu | |
| 225 | | | | 230 | | | | | 235 | | | | | 240 | | |
| aag | aaa | aat | gat | aga | ttt | atc | gct | tct | gtg | aca | gac | agt | gaa | aac | aca | 964 |
| Lys | Lys | Asn | Asp | Arg | Phe | Ile | Ala | Ser | Val | Thr | Asp | Ser | Glu | Asn | Thr | |
| 245 | | | | | 250 | | | | | 255 | | | | | | |
| aat | caa | aga | gaa | gct | gca | agt | cat | gga | ttt | gga | aaa | aca | tca | ggg | aat | 1012 |
| Asn | Gln | Arg | Glu | Ala | Ala | Ser | His | Gly | Phe | Gly | Lys | Thr | Ser | Gly | Asn | |
| 260 | | | | | 265 | | | | | 270 | | | | | | |
| tca | ttt | aaa | gta | aat | agc | tgc | aaa | gac | cac | att | gga | aag | tca | atg | cca | 1060 |
| Ser | Phe | Lys | Val | Asn | Ser | Cys | Lys | Asp | His | Ile | Gly | Lys | Ser | Met | Pro | |
| 275 | | | | | 280 | | | | | 285 | | | | | | |
| aat | gtc | cta | gaa | gat | gaa | gta | tat | gaa | aca | gtt | gta | gat | acc | tct | gaa | 1108 |
| Asn | Val | Leu | Glu | Asp | Glu | Val | Tyr | Glu | Thr | Val | Val | Asp | Thr | Ser | Glu | |
| 290 | | | | | 295 | | | | | 300 | | | | | | |
| gaa | gat | agt | ttt | tca | tta | tgt | ttt | tct | aaa | tgt | aga | aca | aaa | aat | cta | 1156 |
| Glu | Asp | Ser | Phe | Ser | Leu | Cys | Phe | Ser | Lys | Cys | Arg | Thr | Lys | Asn | Leu | |
| 305 | | | | | 310 | | | | | 315 | | | | | 320 | |
| caa | aaa | gta | aga | act | agc | aag | act | agg | aaa | aaa | att | ttc | cat | gaa | gca | 1204 |
| Gln | Lys | Val | Arg | Thr | Ser | Lys | Thr | Arg | Lys | Lys | Ile | Phe | His | Glu | Ala | |
| 325 | | | | | 330 | | | | | 335 | | | | | | |
| aac | gct | gat | gaa | tgt | gaa | aaa | tct | aaa | aac | caa | gtg | aaa | gaa | aaa | tac | 1252 |
| Asn | Ala | Asp | Glu | Cys | Glu | Lys | Ser | Lys | Asn | Gln | Val | Lys | Glu | Lys | Tyr | |
| 340 | | | | | 345 | | | | | 350 | | | | | | |
| tca | ttt | gta | tct | gaa | gtg | gaa | cca | aat | gat | act | gat | cca | tta | gat | tca | 1300 |
| Ser | Phe | Val | Ser | Glu | Val | Glu | Pro | Asn | Asp | Thr | Asp | Pro | Leu | Asp | Ser | |
| 355 | | | | | 360 | | | | | 365 | | | | | | |
| aat | gta | gca | cat | cag | aag | ccc | ttt | gag | agt | gga | agt | gac | aaa | atc | tcc | 1348 |
| Asn | Val | Ala | His | Gln | Lys | Pro | Phe | Glu | Ser | Gly | Ser | Asp | Lys | Ile | Ser | |
| 370 | | | | | 375 | | | | | 380 | | | | | | |
| aag | gaa | gtt | gta | ccg | tct | ttg | gcc | tgt | gaa | tgg | tct | caa | cta | acc | ctt | 1396 |
| Lys | Glu | Val | Val | Pro | Ser | Leu | Ala | Cys | Glu | Trp | Ser | Gln | Leu | Thr | Leu | |
| 385 | | | | | 390 | | | | | 395 | | | | | 400 | |
| tca | ggt | cta | aat | gga | gcc | cag | atg | gag | aaa | ata | ccc | cta | ttg | cat | att | 1444 |
| Ser | Gly | Leu | Asn | Gly | Ala | Gln | Met | Glu | Lys | Ile | Pro | Leu | Leu | His | Ile | |
| 405 | | | | | 410 | | | | | 415 | | | | | | |
| tct | tca | tgt | gac | caa | aat | att | tca | gaa | aaa | gac | cta | tta | gac | aca | gag | 1492 |
| Ser | Ser | Cys | Asp | Gln | Asn | Ile | Ser | Glu | Lys | Asp | Leu | Leu | Asp | Thr | Glu | |
| 420 | | | | | 425 | | | | | 430 | | | | | | |
| aac | aaa | aga | aag | aaa | gat | ttt | ctt | act | tca | gag | aat | tct | ttg | cca | cgt | 1540 |
| Asn | Lys | Arg | Lys | Lys | Asp | Phe | Leu | Thr | Ser | Glu | Asn | Ser | Leu | Pro | Arg | |
| 435 | | | | | 440 | | | | | 445 | | | | | | |
| att | tct | agc | cta | cca | aaa | tca | gag | aag | cca | tta | aat | gag | gaa | aca | gtg | 1588 |
| Ile | Ser | Ser | Leu | Pro | Lys | Ser | Glu | Lys | Pro | Leu | Asn | Glu | Glu | Thr | Val | |
| 450 | | | | | 455 | | | | | 460 | | | | | | |
| gta | aat | aag | aga | gat | gaa | gag | cag | cat | ctt | gaa | tct | cat | aca | gac | tgc | 1636 |
| Val | Asn | Lys | Arg | Asp | Glu | Glu | Gln | His | Leu | Glu | Ser | His | Thr | Asp | Cys | |
| 465 | | | | | 470 | | | | | 475 | | | | | 480 | |
| att | ctt | gca | gta | aag | cag | gca | ata | tct | gga | act | tct | cca | gtg | gct | tct | 1684 |
| Ile | Leu | Ala | Val | Lys | Gln | Ala | Ile | Ser | Gly | Thr | Ser | Pro | Val | Ala | Ser | |
| 485 | | | | | 490 | | | | | 495 | | | | | | |
| tca | ttt | cag | ggt | atc | aaa | aag | tct | ata | ttc | aga | ata | aga | gaa | tca | cct | 1732 |
| Ser | Phe | Gln | Gly | Ile | Lys | Lys | Ser | Ile | Phe | Arg | Ile | Arg | Glu | Ser | Pro | |

-continued

| | | |
|---|---|---|
| 500 | 505 | 510 | aaa gag act ttc aat gca agt ttt tca ggt cat atg act gat cca aac    1780
Lys Glu Thr Phe Asn Ala Ser Phe Ser Gly His Met Thr Asp Pro Asn
515                 520                 525 ttt aaa aaa gaa act gaa gcc tct gaa agt gga ctg gaa ata cat act    1828
Phe Lys Lys Glu Thr Glu Ala Ser Glu Ser Gly Leu Glu Ile His Thr
530                 535                 540 gtt tgc tca cag aag gag gac tcc tta tgt cca aat tta att gat aat    1876
Val Cys Ser Gln Lys Glu Asp Ser Leu Cys Pro Asn Leu Ile Asp Asn
545                 550                 555                 560 gga agc tgg cca gcc acc aca cag aat tct gta gct ttg aag aat        1924
Gly Ser Trp Pro Ala Thr Thr Thr Gln Asn Ser Val Ala Leu Lys Asn
565                 570                 575 gca ggt tta ata tcc act ttg aaa aag aaa aca aat aag ttt att tat    1972
Ala Gly Leu Ile Ser Thr Leu Lys Lys Lys Thr Asn Lys Phe Ile Tyr
580                 585                 590 gct ata cat gat gaa aca ttt tat aaa gga aaa aaa ata ccg aaa gac    2020
Ala Ile His Asp Glu Thr Phe Tyr Lys Gly Lys Lys Ile Pro Lys Asp
595                 600                 605 caa aaa tca gaa cta att aac tgt tca gcc cag ttt gaa gca aat gct    2068
Gln Lys Ser Glu Leu Ile Asn Cys Ser Ala Gln Phe Glu Ala Asn Ala
610                 615                 620 ttt gaa gca cca ctt aca ttt gca aat gct gat tca ggt tta ttg cat    2116
Phe Glu Ala Pro Leu Thr Phe Ala Asn Ala Asp Ser Gly Leu Leu His
625                 630                 635                 640 tct tct gtg aaa aga agc tgt tca cag aat gat tct gaa gaa cca act    2164
Ser Ser Val Lys Arg Ser Cys Ser Gln Asn Asp Ser Glu Glu Pro Thr
645                 650                 655 ttg tcc tta act agc tct ttt ggg aca att ctg agg aaa tgt tct aga    2212
Leu Ser Leu Thr Ser Ser Phe Gly Thr Ile Leu Arg Lys Cys Ser Arg
660                 665                 670 aat gaa aca tgt tct aat aat aca gta atc tct cag gat ctt gat tat    2260
Asn Glu Thr Cys Ser Asn Asn Thr Val Ile Ser Gln Asp Leu Asp Tyr
675                 680                 685 aaa gaa gca aaa tgt aat aag gaa aaa cta cag tta ttt att acc cca    2308
Lys Glu Ala Lys Cys Asn Lys Glu Lys Leu Gln Leu Phe Ile Thr Pro
690                 695                 700 gaa gct gat tct ctg tca tgc ctg cag gaa gga cag tgt gaa aat gat    2356
Glu Ala Asp Ser Leu Ser Cys Leu Gln Glu Gly Gln Cys Glu Asn Asp
705                 710                 715                 720 cca aaa agc aaa aaa gtt tca gat ata aaa gaa gag gtc ttg gct gca    2404
Pro Lys Ser Lys Lys Val Ser Asp Ile Lys Glu Glu Val Leu Ala Ala
725                 730                 735 gca tgt cac cca gta caa cat tca aaa gtg gaa tac agt gat act gac    2452
Ala Cys His Pro Val Gln His Ser Lys Val Glu Tyr Ser Asp Thr Asp
740                 745                 750 ttt caa tcc cag aaa agt ctt tta tat gat cat gaa aat gcc agc act    2500
Phe Gln Ser Gln Lys Ser Leu Leu Tyr Asp His Glu Asn Ala Ser Thr
755                 760                 765 ctt att tta act cct act tcc aag gat gtt ctg tca aac cta gtc atg    2548
Leu Ile Leu Thr Pro Thr Ser Lys Asp Val Leu Ser Asn Leu Val Met
770                 775                 780 att tct aga ggc aaa gaa tca tac aaa atg tca gac aag ctc aaa ggt    2596
Ile Ser Arg Gly Lys Glu Ser Tyr Lys Met Ser Asp Lys Leu Lys Gly
785                 790                 795                 800 aac aat tat gaa tct gat gtt gaa tta acc aaa aat att ccc atg gaa    2644
Asn Asn Tyr Glu Ser Asp Val Glu Leu Thr Lys Asn Ile Pro Met Glu
805                 810                 815 aag aat caa gat gta tgt gct tta aat gaa aat tat aaa aac gtt gag    2692

```
                                              -continued

Lys Asn Gln Asp Val Cys Ala Leu Asn Glu Asn Tyr Lys Asn Val Glu
820                 825                 830 ctg ttg cca cct gaa aaa tac atg aga gta gca tca cct tca aga aag       2740
Leu Leu Pro Pro Glu Lys Tyr Met Arg Val Ala Ser Pro Ser Arg Lys
835                 840                 845 gta caa ttc aac caa aac aca aat cta aga gta atc caa aaa aat caa       2788
Val Gln Phe Asn Gln Asn Thr Asn Leu Arg Val Ile Gln Lys Asn Gln
850                 855                 860 gaa gaa act act tca att tca aaa ata act gtc aat cca gac tct gaa       2836
Glu Glu Thr Thr Ser Ile Ser Lys Ile Thr Val Asn Pro Asp Ser Glu
865                 870                 875                 880 gaa ctt ttc tca gac aat gag aat aat ttt gtc ttc caa gta gct aat       2884
Glu Leu Phe Ser Asp Asn Glu Asn Asn Phe Val Phe Gln Val Ala Asn
885                 890                 895 gaa agg aat aat ctt gct tta gga aat act aag gaa ctt cat gaa aca       2932
Glu Arg Asn Asn Leu Ala Leu Gly Asn Thr Lys Glu Leu His Glu Thr
900                 905                 910 gac ttg act tgt gta aac gaa ccc att ttc aag aac tct acc atg gtt       2980
Asp Leu Thr Cys Val Asn Glu Pro Ile Phe Lys Asn Ser Thr Met Val
915                 920                 925 tta tat gga gac aca ggt gat aaa caa gca acc caa gtg tca att aaa       3028
Leu Tyr Gly Asp Thr Gly Asp Lys Gln Ala Thr Gln Val Ser Ile Lys
930                 935                 940 aaa gat ttg gtt tat gtt ctt gca gag gag aac aaa aat agt gta aag       3076
Lys Asp Leu Val Tyr Val Leu Ala Glu Glu Asn Lys Asn Ser Val Lys
945                 950                 955                 960 cag cat ata aaa atg act cta ggt caa gat tta aaa tcg gac atc tcc       3124
Gln His Ile Lys Met Thr Leu Gly Gln Asp Leu Lys Ser Asp Ile Ser
965                 970                 975 ttg aat ata gat aaa ata cca gaa aaa aat aat gat tac atg aac aaa       3172
Leu Asn Ile Asp Lys Ile Pro Glu Lys Asn Asn Asp Tyr Met Asn Lys
980                 985                 990 tgg gca gga ctc tta ggt cca att tca aat cac agt ttt gga ggt agc       3220
Trp Ala Gly Leu Leu Gly Pro Ile Ser Asn His Ser Phe Gly Gly Ser
995                 1000                1005 ttc aga aca gct tca aat aag gaa atc aag ctc tct gaa cat aac att       3268
Phe Arg Thr Ala Ser Asn Lys Glu Ile Lys Leu Ser Glu His Asn Ile
1010                1015                1020 aag aag agc aaa atg ttc ttc aaa gat att gaa gaa caa tat cct act       3316
Lys Lys Ser Lys Met Phe Phe Lys Asp Ile Glu Glu Gln Tyr Pro Thr
1025                1030                1035                1040 agt tta gct tgt gtt gaa att gta aat acc ttg gca tta gat aat caa       3364
Ser Leu Ala Cys Val Glu Ile Val Asn Thr Leu Ala Leu Asp Asn Gln
1045                1050                1055 aag aaa ctg agc aag cct cag tca att aat act gta tct gca cat tta       3412
Lys Lys Leu Ser Lys Pro Gln Ser Ile Asn Thr Val Ser Ala His Leu
1060                1065                1070 cag agt agt gta gtt gtt tct gat tgt aaa aat agt cat ata acc cct       3460
Gln Ser Ser Val Val Val Ser Asp Cys Lys Asn Ser His Ile Thr Pro
1075                1080                1085 cag atg tta ttt tcc aag cag gat ttt aat tca aac cat aat tta aca       3508
Gln Met Leu Phe Ser Lys Gln Asp Phe Asn Ser Asn His Asn Leu Thr
1090                1095                1100 cct agc caa aag gca gaa att aca gaa ctt tct act ata tta gaa gaa       3556
Pro Ser Gln Lys Ala Glu Ile Thr Glu Leu Ser Thr Ile Leu Glu Glu
1105                1110                1115                1120 tca gga agt cag ttt gaa ttt act cag ttt aga aaa cca agc tac ata       3604
Ser Gly Ser Gln Phe Glu Phe Thr Gln Phe Arg Lys Pro Ser Tyr Ile
1125                1130                1135
```

```
ttg cag aag agt aca ttt gaa gtg cct gaa aac cag atg act atc tta      3652
Leu Gln Lys Ser Thr Phe Glu Val Pro Glu Asn Gln Met Thr Ile Leu
1140            1145                1150 aag acc act tct gag gaa tgc aga gat gct gat ctt cat gtc ata atg      3700
Lys Thr Thr Ser Glu Glu Cys Arg Asp Ala Asp Leu His Val Ile Met
1155            1160                1165 aat gcc cca tcg att ggt cag gta gac agc agc aag caa ttt gaa ggt      3748
Asn Ala Pro Ser Ile Gly Gln Val Asp Ser Ser Lys Gln Phe Glu Gly
1170            1175                1180 aca gtt gaa att aaa cgg aag ttt gct ggc ctg ttg aaa aat gac tgt      3796
Thr Val Glu Ile Lys Arg Lys Phe Ala Gly Leu Leu Lys Asn Asp Cys
1185            1190                1195            1200 aac aaa agt gct tct ggt tat tta aca gat gaa aat gaa gtg ggg ttt      3844
Asn Lys Ser Ala Ser Gly Tyr Leu Thr Asp Glu Asn Glu Val Gly Phe
1205            1210                1215 agg ggc ttt tat tct gct cat ggc aca aaa ctg aat gtt tct act gaa      3892
Arg Gly Phe Tyr Ser Ala His Gly Thr Lys Leu Asn Val Ser Thr Glu
1220            1225                1230 gct ctg caa aaa gct gtg aaa ctg ttt agt gat att gag aat att agt      3940
Ala Leu Gln Lys Ala Val Lys Leu Phe Ser Asp Ile Glu Asn Ile Ser
1235            1240                1245 gag gaa act tct gca gag gta cat cca ata agt tta tct tca agt aaa      3988
Glu Glu Thr Ser Ala Glu Val His Pro Ile Ser Leu Ser Ser Ser Lys
1250            1255                1260 tgt cat gat tct gtt gtt tca atg ttt aag ata gaa aat cat aat gat      4036
Cys His Asp Ser Val Val Ser Met Phe Lys Ile Glu Asn His Asn Asp
1265            1270                1275            1280 aaa act gta agt gaa aaa aat aat aaa tgc caa ctg ata tta caa aat      4084
Lys Thr Val Ser Glu Lys Asn Asn Lys Cys Gln Leu Ile Leu Gln Asn
1285            1290                1295 aat att gaa atg act act ggc act ttt gtt gaa gaa att act gaa aat      4132
Asn Ile Glu Met Thr Thr Gly Thr Phe Val Glu Glu Ile Thr Glu Asn
1300            1305                1310 tac aag aga aat act gaa aat gaa gat aac aaa tat act gct gcc agt      4180
Tyr Lys Arg Asn Thr Glu Asn Glu Asp Asn Lys Tyr Thr Ala Ala Ser
1315            1320                1325 aga aat tct cat aac tta gaa ttt gat ggc agt gat tca agt aaa aat      4228
Arg Asn Ser His Asn Leu Glu Phe Asp Gly Ser Asp Ser Ser Lys Asn
1330            1335                1340 gat act gtt tgt att cat aaa gat gaa acg gac ttg cta ttt act gat      4276
Asp Thr Val Cys Ile His Lys Asp Glu Thr Asp Leu Leu Phe Thr Asp
1345            1350                1355            1360 cag cac aac ata tgt ctt aaa tta tct ggc cag ttt atg aag gag gga      4324
Gln His Asn Ile Cys Leu Lys Leu Ser Gly Gln Phe Met Lys Glu Gly
1365            1370                1375 aac act cag att aaa gaa gat ttg tca gat tta act ttt ttg gaa gtt      4372
Asn Thr Gln Ile Lys Glu Asp Leu Ser Asp Leu Thr Phe Leu Glu Val
1380            1385                1390 gcg aaa gct caa gaa gca tgt cat ggt aat act tca aat aaa gaa cag      4420
Ala Lys Ala Gln Glu Ala Cys His Gly Asn Thr Ser Asn Lys Glu Gln
1395            1400                1405 tta act gct act aaa acg gag caa aat ata aaa gat ttt gag act tct      4468
Leu Thr Ala Thr Lys Thr Glu Gln Asn Ile Lys Asp Phe Glu Thr Ser
1410            1415                1420 gat aca ttt ttt cag act gca agt ggg aaa aat att agt gtc gcc aaa      4516
Asp Thr Phe Phe Gln Thr Ala Ser Gly Lys Asn Ile Ser Val Ala Lys
1425            1430                1435            1440 gag tta ttt aat aaa att gta aat ttc ttt gat cag aaa cca gaa gaa      4564
Glu Leu Phe Asn Lys Ile Val Asn Phe Phe Asp Gln Lys Pro Glu Glu
1445            1450                1455
```

```
ttg cat aac ttt tcc tta aat tct gaa tta cat tct gac ata aga aag    4612
Leu His Asn Phe Ser Leu Asn Ser Glu Leu His Ser Asp Ile Arg Lys
1460                1465                1470 aac aaa atg gac att cta agt tat gag gaa aca gac ata gtt aaa cac    4660
Asn Lys Met Asp Ile Leu Ser Tyr Glu Glu Thr Asp Ile Val Lys His
    1475                1480                1485 aaa ata ctg aaa gaa agt gtc cca gtt ggt act gga aat caa cta gtg    4708
Lys Ile Leu Lys Glu Ser Val Pro Val Gly Thr Gly Asn Gln Leu Val
1490                1495                1500 acc ttc cag gga caa ccc gaa cgt gat gaa aag atc aaa gaa cct act    4756
Thr Phe Gln Gly Gln Pro Glu Arg Asp Glu Lys Ile Lys Glu Pro Thr
1505                1510                1515                1520 ctg ttg ggt ttt cat aca gct agc gga aaa aaa gtt aaa att gca aag    4804
Leu Leu Gly Phe His Thr Ala Ser Gly Lys Lys Val Lys Ile Ala Lys
        1525                1530                1535 gaa tct ttg gac aaa gtg aaa aac ctt ttt gat gaa aaa gag caa ggt    4852
Glu Ser Leu Asp Lys Val Lys Asn Leu Phe Asp Glu Lys Glu Gln Gly
1540                1545                1550 act agt gaa atc acc agt ttt agc cat caa tgg gca aag acc cta aag    4900
Thr Ser Glu Ile Thr Ser Phe Ser His Gln Trp Ala Lys Thr Leu Lys
1555                1560                1565 tac aga gag gcc tgt aaa gac ctt gaa tta gca tgt gag acc att gag    4948
Tyr Arg Glu Ala Cys Lys Asp Leu Glu Leu Ala Cys Glu Thr Ile Glu
1570                1575                1580 atc aca gct gcc cca aag tgt aaa gaa atg cag aat tct ctc aat aat    4996
Ile Thr Ala Ala Pro Lys Cys Lys Glu Met Gln Asn Ser Leu Asn Asn
    1585                1590                1595                1600 gat aaa aac ctt gtt tct att gag act gtg gtg cca cct aag ctc tta    5044
Asp Lys Asn Leu Val Ser Ile Glu Thr Val Val Pro Pro Lys Leu Leu
1605                1610                1615 agt gat aat tta tgt aga caa act gaa aat ctc aaa aca tca aaa agt    5092
Ser Asp Asn Leu Cys Arg Gln Thr Glu Asn Leu Lys Thr Ser Lys Ser
1620                1625                1630 atc ttt ttg aaa gtt aaa gta cat gaa aat gta gaa aaa gaa aca gca    5140
Ile Phe Leu Lys Val Lys Val His Glu Asn Val Glu Lys Glu Thr Ala
1635                1640                1645 aaa agt cct gca act tgt tac aca aat cag tcc cct tat tca gtc att    5188
Lys Ser Pro Ala Thr Cys Tyr Thr Asn Gln Ser Pro Tyr Ser Val Ile
    1650                1655                1660 gaa aat tca gcc tta gct ttt tac aca agt tgt agt aga aaa act tct    5236
Glu Asn Ser Ala Leu Ala Phe Tyr Thr Ser Cys Ser Arg Lys Thr Ser
1665                1670                1675                1680 gtg agt cag act tca tta ctt gaa gca aaa aaa tgg ctt aga gaa gga    5284
Val Ser Gln Thr Ser Leu Leu Glu Ala Lys Lys Trp Leu Arg Glu Gly
    1685                1690                1695 ata ttt gat ggt caa cca gaa aga ata aat act gca gat tat gta gga    5332
Ile Phe Asp Gly Gln Pro Glu Arg Ile Asn Thr Ala Asp Tyr Val Gly
1700                1705                1710 aat tat ttg tat gaa aat aat tca aac agt act ata gct gaa aat gac    5380
Asn Tyr Leu Tyr Glu Asn Asn Ser Asn Ser Thr Ile Ala Glu Asn Asp
1715                1720                1725 aaa aat cat ctc tcc gaa aaa caa gat act tat tta agt aac agt agc    5428
Lys Asn His Leu Ser Glu Lys Gln Asp Thr Tyr Leu Ser Asn Ser Ser
    1730                1735                1740 atg tct aac agc tat tcc tac cat tct gat gag gta tat aat gat tca    5476
Met Ser Asn Ser Tyr Ser Tyr His Ser Asp Glu Val Tyr Asn Asp Ser
1745                1750                1755                1760 gga tat ctc tca aaa aat aaa ctt gat tct ggt att gag cca gta ttg    5524
Gly Tyr Leu Ser Lys Asn Lys Leu Asp Ser Gly Ile Glu Pro Val Leu
```

-continued

```
           1765                1770                1775
aag aat gtt gaa gat caa aaa aac act agt ttt tcc aaa gta ata tcc      5572
Lys Asn Val Glu Asp Gln Lys Asn Thr Ser Phe Ser Lys Val Ile Ser
1780                1785                1790 aat gta aaa gat gca aat gca tac cca caa act gta aat gaa gat att      5620
Asn Val Lys Asp Ala Asn Ala Tyr Pro Gln Thr Val Asn Glu Asp Ile
1795                1800                1805 tgc gtt gag gaa ctt gtg act agc tct tca ccc tgc aaa aat aaa aat      5668
Cys Val Glu Glu Leu Val Thr Ser Ser Ser Pro Cys Lys Asn Lys Asn
1810                1815                1820 gca gcc att aaa ttg tcc ata tct aat agt aat aat ttt gag gta ggg      5716
Ala Ala Ile Lys Leu Ser Ile Ser Asn Ser Asn Asn Phe Glu Val Gly
1825                1830                1835                1840 cca cct gca ttt agg ata gcc agt ggt aaa atc cgt ttg tgt tca cat      5764
Pro Pro Ala Phe Arg Ile Ala Ser Gly Lys Ile Arg Leu Cys Ser His
1845                1850                1855 gaa aca att aaa aaa gtg aaa gac ata ttt aca gac agt ttc agc aaa      5812
Glu Thr Ile Lys Lys Val Lys Asp Ile Phe Thr Asp Ser Phe Ser Lys
1860                1865                1870 gta att aag gaa aac aac gag aat aaa tca aaa att tgc caa acg aaa      5860
Val Ile Lys Glu Asn Asn Glu Asn Lys Ser Lys Ile Cys Gln Thr Lys
1875                1880                1885 att atg gca ggt tgt tac gag gca ttg gat gat tca gag gat att ctt      5908
Ile Met Ala Gly Cys Tyr Glu Ala Leu Asp Asp Ser Glu Asp Ile Leu
1890                1895                1900 cat aac tct cta gat aat gat gaa tgt agc atg cat tca cat aag gtt      5956
His Asn Ser Leu Asp Asn Asp Glu Cys Ser Met His Ser His Lys Val
1905                1910                1915                1920 ttt gct gac att cag agt gaa gaa att tta caa cat aac caa aat atg      6004
Phe Ala Asp Ile Gln Ser Glu Glu Ile Leu Gln His Asn Gln Asn Met
1925                1930                1935 tct gga ttg gag aaa gtt tct aaa ata tca cct tgt gat gtt agt ttg      6052
Ser Gly Leu Glu Lys Val Ser Lys Ile Ser Pro Cys Asp Val Ser Leu
1940                1945                1950 gaa act tca gat ata tgt aaa tgt agt ata ggg aag ctt cat aag tca      6100
Glu Thr Ser Asp Ile Cys Lys Cys Ser Ile Gly Lys Leu His Lys Ser
1955                1960                1965 gtc tca tct gca aat act tgt ggg att ttt agc aca gca agt gga aaa      6148
Val Ser Ser Ala Asn Thr Cys Gly Ile Phe Ser Thr Ala Ser Gly Lys
1970                1975                1980 tct gtc cag gta tca gat gct tca tta caa aac gca aga caa gtg ttt      6196
Ser Val Gln Val Ser Asp Ala Ser Leu Gln Asn Ala Arg Gln Val Phe
1985                1990                1995                2000 tct gaa ata gaa gat agt acc aag caa gtc ttt tcc aaa gta ttg ttt      6244
Ser Glu Ile Glu Asp Ser Thr Lys Gln Val Phe Ser Lys Val Leu Phe
2005                2010                2015 aaa agt aac gaa cat tca gac cag ctc aca aga gaa gaa aat act gct      6292
Lys Ser Asn Glu His Ser Asp Gln Leu Thr Arg Glu Glu Asn Thr Ala
2020                2025                2030 ata cgt act cca gaa cat tta ata tcc caa aaa ggc ttt tca tat aat      6340
Ile Arg Thr Pro Glu His Leu Ile Ser Gln Lys Gly Phe Ser Tyr Asn
2035                2040                2045 gtg gta aat tca tct gct ttc tct gga ttt agt aca gca agt gga aag      6388
Val Val Asn Ser Ser Ala Phe Ser Gly Phe Ser Thr Ala Ser Gly Lys
2050                2055                2060 caa gtt tcc att tta gaa agt tcc tta cac aaa gtt aag gga gtg tta      6436
Gln Val Ser Ile Leu Glu Ser Ser Leu His Lys Val Lys Gly Val Leu
2065                2070                2075                2080 gag gaa ttt gat tta atc aga act gag cat agt ctt cac tat tca cct      6484
```

-continued

```
Glu Glu Phe Asp Leu Ile Arg Thr Glu His Ser Leu His Tyr Ser Pro
2085                2090                2095 acg tct aga caa aat gta tca aaa ata ctt cct cgt gtt gat aag aga      6532
Thr Ser Arg Gln Asn Val Ser Lys Ile Leu Pro Arg Val Asp Lys Arg
2100                2105                2110 aac cca gag cac tgt gta aac tca gaa atg gaa aaa acc tgc agt aaa      6580
Asn Pro Glu His Cys Val Asn Ser Glu Met Glu Lys Thr Cys Ser Lys
2115                2120                2125 gaa ttt aaa tta tca aat aac tta aat gtt gaa ggt ggt tct tca gaa      6628
Glu Phe Lys Leu Ser Asn Asn Leu Asn Val Glu Gly Gly Ser Ser Glu
2130                2135                2140 aat aat cac tct att aaa gtt tct cca tat ctc tct caa ttt caa caa      6676
Asn Asn His Ser Ile Lys Val Ser Pro Tyr Leu Ser Gln Phe Gln Gln
2145                2150                2155                2160 gac aaa caa cag ttg gta tta gga acc aaa gtc tca ctt gtt gag aac      6724
Asp Lys Gln Gln Leu Val Leu Gly Thr Lys Val Ser Leu Val Glu Asn
2165                2170                2175 att cat gtt ttg gga aaa gaa cag gct tca cct aaa aac gta aaa atg      6772
Ile His Val Leu Gly Lys Glu Gln Ala Ser Pro Lys Asn Val Lys Met
2180                2185                2190 gaa att ggt aaa act gaa act ttt tct gat gtt cct gtg aaa aca aat      6820
Glu Ile Gly Lys Thr Glu Thr Phe Ser Asp Val Pro Val Lys Thr Asn
2195                2200                2205 ata gaa gtt tgt tct act tac tcc aaa gat tca gaa aac tac ttt gaa      6868
Ile Glu Val Cys Ser Thr Tyr Ser Lys Asp Ser Glu Asn Tyr Phe Glu
2210                2215                2220 aca gaa gca gta gaa att gct aaa gct ttt atg gaa gat gat gaa ctg      6916
Thr Glu Ala Val Glu Ile Ala Lys Ala Phe Met Glu Asp Asp Glu Leu
2225                2230                2235                2240 aca gat tct aaa ctg cca agt cat gcc aca cat tct ctt ttt aca tgt      6964
Thr Asp Ser Lys Leu Pro Ser His Ala Thr His Ser Leu Phe Thr Cys
2245                2250                2255 ccc gaa aat gag gaa atg gtt ttg tca aat tca aga att gga aaa aga      7012
Pro Glu Asn Glu Glu Met Val Leu Ser Asn Ser Arg Ile Gly Lys Arg
2260                2265                2270 aga gga gag ccc ctt atc tta gtg gga gaa ccc tca atc aaa aga aac      7060
Arg Gly Glu Pro Leu Ile Leu Val Gly Glu Pro Ser Ile Lys Arg Asn
2275                2280                2285 tta tta aat gaa ttt gac agg ata ata gaa aat caa gaa aaa tcc tta      7108
Leu Leu Asn Glu Phe Asp Arg Ile Ile Glu Asn Gln Glu Lys Ser Leu
2290                2295                2300 aag gct tca aaa agc act cca gat ggc aca ata aaa gat cga aga ttg      7156
Lys Ala Ser Lys Ser Thr Pro Asp Gly Thr Ile Lys Asp Arg Arg Leu
2305                2310                2315                2320 ttt atg cat cat gtt tct tta gag ccg att acc tgt gta ccc ttt cgc      7204
Phe Met His His Val Ser Leu Glu Pro Ile Thr Cys Val Pro Phe Arg
2325                2330                2335 aca act aag gaa cgt caa gag ata cag aat cca aat ttt acc gca cct      7252
Thr Thr Lys Glu Arg Gln Glu Ile Gln Asn Pro Asn Phe Thr Ala Pro
2340                2345                2350 ggt caa gaa ttt ctg tct aaa tct cat ttg tat gaa cat ctg act ttg      7300
Gly Gln Glu Phe Leu Ser Lys Ser His Leu Tyr Glu His Leu Thr Leu
2355                2360                2365 gaa aaa tct tca agc aat tta gca gtt tca gga cat cca ttt tat caa      7348
Glu Lys Ser Ser Ser Asn Leu Ala Val Ser Gly His Pro Phe Tyr Gln
2370                2375                2380 gtt tct gct aca aga aat gaa aaa atg aga cac ttg att act aca ggc      7396
Val Ser Ala Thr Arg Asn Glu Lys Met Arg His Leu Ile Thr Thr Gly
2385                2390                2395                2400
```

-continued

| | | |
|---|---|---|
| aga cca acc aaa gtc ttt gtt cca cct ttt aaa act aaa tca cat ttt<br>Arg Pro Thr Lys Val Phe Val Pro Pro Phe Lys Thr Lys Ser His Phe<br>2405          2410                  2415 | 7444 |
| cac aga gtt gaa cag tgt gtt agg aat att aac ttg gag gaa aac aga<br>His Arg Val Glu Gln Cys Val Arg Asn Ile Asn Leu Glu Glu Asn Arg<br>2420          2425                  2430 | 7492 |
| caa aag caa aac att gat gga cat ggc tct gat gat agt aaa aat aag<br>Gln Lys Gln Asn Ile Asp Gly His Gly Ser Asp Asp Ser Lys Asn Lys<br>2435          2440                  2445 | 7540 |
| att aat gac aat gag att cat cag ttt aac aaa aac tcc aat caa<br>Ile Asn Asp Asn Glu Ile His Gln Phe Asn Lys Asn Asn Ser Asn Gln<br>2450          2455                  2460 | 7588 |
| gca gca gct gta act ttc aca aag tgt gaa gaa gaa cct tta gat tta<br>Ala Ala Ala Val Thr Phe Thr Lys Cys Glu Glu Glu Pro Leu Asp Leu<br>2465          2470              2475              2480 | 7636 |
| att aca agt ctt cag aat gcc aga gat ata cag gat atg cga att aag<br>Ile Thr Ser Leu Gln Asn Ala Arg Asp Ile Gln Asp Met Arg Ile Lys<br>2485          2490                  2495 | 7684 |
| aag aaa caa agg caa cgc gtc ttt cca cag cca ggc agt ctg tat ctt<br>Lys Lys Gln Arg Gln Arg Val Phe Pro Gln Pro Gly Ser Leu Tyr Leu<br>2500          2505                  2510 | 7732 |
| gca aaa aca tcc act ctg cct cga atc tct ctg aaa gca gca gta gga<br>Ala Lys Thr Ser Thr Leu Pro Arg Ile Ser Leu Lys Ala Ala Val Gly<br>2515          2520                  2525 | 7780 |
| ggc caa gtt ccc tct gcg tgt tct cat aaa cag ctg tat acg tat ggc<br>Gly Gln Val Pro Ser Ala Cys Ser His Lys Gln Leu Tyr Thr Tyr Gly<br>2530          2535                  2540 | 7828 |
| gtt tct aaa cat tgc ata aaa att aac agc aaa aat gca gag tct ttt<br>Val Ser Lys His Cys Ile Lys Ile Asn Ser Lys Asn Ala Glu Ser Phe<br>2545          2550              2555              2560 | 7876 |
| cag ttt cac act gaa gat tat ttt ggt aag gaa agt tta tgg act gga<br>Gln Phe His Thr Glu Asp Tyr Phe Gly Lys Glu Ser Leu Trp Thr Gly<br>2565          2570                  2575 | 7924 |
| aaa gga ata cag ttg gct gat ggt gga tgg ctc ata ccc tcc aat gat<br>Lys Gly Ile Gln Leu Ala Asp Gly Gly Trp Leu Ile Pro Ser Asn Asp<br>2580          2585                  2590 | 7972 |
| gga aag gct gga aaa gaa gaa ttt tat agg gct ctg tgt gac act cca<br>Gly Lys Ala Gly Lys Glu Glu Phe Tyr Arg Ala Leu Cys Asp Thr Pro<br>2595          2600                  2605 | 8020 |
| ggt gtg gat cca aag ctt att tct aga att tgg gtt tat aat cac tat<br>Gly Val Asp Pro Lys Leu Ile Ser Arg Ile Trp Val Tyr Asn His Tyr<br>2610          2615                  2620 | 8068 |
| aga tgg atc ata tgg aaa ctg gca gct atg gaa tgt gcc ttt cct aag<br>Arg Trp Ile Ile Trp Lys Leu Ala Ala Met Glu Cys Ala Phe Pro Lys<br>2625          2630                  2635              2640 | 8116 |
| gaa ttt gct aat aga tgc cta agc cca gaa agg gtg ctt ctt caa cta<br>Glu Phe Ala Asn Arg Cys Leu Ser Pro Glu Arg Val Leu Leu Gln Leu<br>2645          2650                  2655 | 8164 |
| aaa tac aga tat gat acg gaa att gat aga agc aga aga tcg gct ata<br>Lys Tyr Arg Tyr Asp Thr Glu Ile Asp Arg Ser Arg Arg Ser Ala Ile<br>2660          2665                  2670 | 8212 |
| aaa aag ata atg gaa agg gat gac aca gct gca aaa aca ctt gtt ctc<br>Lys Lys Ile Met Glu Arg Asp Asp Thr Ala Ala Lys Thr Leu Val Leu<br>2675          2680                  2685 | 8260 |
| tgt gtt tct gac ata att tca ttg agc gca aat ata tct gaa act tct<br>Cys Val Ser Asp Ile Ile Ser Leu Ser Ala Asn Ile Ser Glu Thr Ser<br>2690          2695                  2700 | 8308 |
| agc aat aaa act agt agt gca gat acc caa aaa gtg gcc att att gaa<br>Ser Asn Lys Thr Ser Ser Ala Asp Thr Gln Lys Val Ala Ile Ile Glu<br>2705          2710                  2715              2720 | 8356 |

```
ctt aca gat ggg tgg tat gct gtt aag gcc cag tta gat cct ccc ctc       8404
Leu Thr Asp Gly Trp Tyr Ala Val Lys Ala Gln Leu Asp Pro Pro Leu
2725                2730                2735 tta gct gtc tta aag aat ggc aga ctg aca gtt ggt cag aag att att       8452
Leu Ala Val Leu Lys Asn Gly Arg Leu Thr Val Gly Gln Lys Ile Ile
        2740                2745                2750 ctt cat gga gca gaa ctg gtg ggc tct cct gat gcc tgt aca cct ctt       8500
Leu His Gly Ala Glu Leu Val Gly Ser Pro Asp Ala Cys Thr Pro Leu
2755                2760                2765 gaa gcc cca gaa tct ctt atg tta aag att tct gct aac agt act cgg       8548
Glu Ala Pro Glu Ser Leu Met Leu Lys Ile Ser Ala Asn Ser Thr Arg
2770                2775                2780 cct gct cgc tgg tat acc aaa ctt gga ttc ttt cct gac cct aga cct       8596
Pro Ala Arg Trp Tyr Thr Lys Leu Gly Phe Phe Pro Asp Pro Arg Pro
2785                2790                2795                2800 ttt cct ctg ccc tta tca tcg ctt ttc agt gat gga gga aat gtt ggt       8644
Phe Pro Leu Pro Leu Ser Ser Leu Phe Ser Asp Gly Gly Asn Val Gly
2805                2810                2815 tgt gtt gat gta att att caa aga gca tac cct ata cag cgg atg gag       8692
Cys Val Asp Val Ile Ile Gln Arg Ala Tyr Pro Ile Gln Arg Met Glu
2820                2825                2830 aag aca tca tct gga tta tac ata ttt cgc aat gaa aga gag gaa gaa       8740
Lys Thr Ser Ser Gly Leu Tyr Ile Phe Arg Asn Glu Arg Glu Glu Glu
2835                2840                2845 aag gaa gca gca aaa tat gtg gag gcc caa caa aag aga cta gaa gcc       8788
Lys Glu Ala Ala Lys Tyr Val Glu Ala Gln Gln Lys Arg Leu Glu Ala
2850                2855                2860 tta ttc act aaa att cag gag gaa ttt gaa gaa cat gaa gaa aac aca       8836
Leu Phe Thr Lys Ile Gln Glu Glu Phe Glu Glu His Glu Glu Asn Thr
2865                2870                2875                2880 aca aaa cca tat tta cca tca cgt gca cta aca aga cag caa gtt cgt       8884
Thr Lys Pro Tyr Leu Pro Ser Arg Ala Leu Thr Arg Gln Gln Val Arg
2885                2890                2895 gct ttg caa gat ggt gca gag ctt tat gaa gca gtg aag aat gca gca       8932
Ala Leu Gln Asp Gly Ala Glu Leu Tyr Glu Ala Val Lys Asn Ala Ala
2900                2905                2910 gac cca gct tac ctt gag ggt tat ttc agt gaa gag cag tta aga gcc       8980
Asp Pro Ala Tyr Leu Glu Gly Tyr Phe Ser Glu Glu Gln Leu Arg Ala
2915                2920                2925 ttg aat aat cac agg caa atg ttg aat gat aag aaa caa gct cag atc       9028
Leu Asn Asn His Arg Gln Met Leu Asn Asp Lys Lys Gln Ala Gln Ile
2930                2935                2940 cag ttg gaa att agg aag gcc atg gaa tct gct gaa caa aag gaa caa       9076
Gln Leu Glu Ile Arg Lys Ala Met Glu Ser Ala Glu Gln Lys Glu Gln
2945                2950                2955                2960 ggt tta tca agg gat gtc aca acc gtg tgg aag ttg cgt att gta agc       9124
Gly Leu Ser Arg Asp Val Thr Thr Val Trp Lys Leu Arg Ile Val Ser
2965                2970                2975 tat tca aaa aaa gaa aaa gat tca gtt ata ctg agt att tgg cgt cca       9172
Tyr Ser Lys Lys Glu Lys Asp Ser Val Ile Leu Ser Ile Trp Arg Pro
2980                2985                2990 tca tca gat tta tat tct ctg tta aca gaa gga aag aga tac aga att       9220
Ser Ser Asp Leu Tyr Ser Leu Leu Thr Glu Gly Lys Arg Tyr Arg Ile
2995                3000                3005 tat cat ctt gca act tca aaa tct aaa agt aaa tct gaa aga gct aac       9268
Tyr His Leu Ala Thr Ser Lys Ser Lys Ser Lys Ser Glu Arg Ala Asn
3010                3015                3020 ata cag tta gca gcg aca aaa aaa act cag tat caa caa cta ccg gtt       9316
Ile Gln Leu Ala Ala Thr Lys Lys Thr Gln Tyr Gln Gln Leu Pro Val
```

```
                 3025                3030                3035                3040
tca gat gaa att tta ttt cag att tac cag cca cgg gag ccc ctt cac            9364
Ser Asp Glu Ile Leu Phe Gln Ile Tyr Gln Pro Arg Glu Pro Leu His
3045                3050                3055 ttc agc aaa ttt tta gat cca gac ttt cag cca tct tgt tct gag gtg            9412
Phe Ser Lys Phe Leu Asp Pro Asp Phe Gln Pro Ser Cys Ser Glu Val
3060                3065                3070 gac cta ata gga ttt gtc gtt tct gtt gtg aaa aaa aca gga ctt gcc            9460
Asp Leu Ile Gly Phe Val Val Ser Val Val Lys Lys Thr Gly Leu Ala
3075                3080                3085 cct ttc gtc tat ttg tca gac gaa tgt tac aat tta ctg gca ata aag            9508
Pro Phe Val Tyr Leu Ser Asp Glu Cys Tyr Asn Leu Leu Ala Ile Lys
3090                3095                3100 ttt tgg ata gac ctt aat gag gac att att aag cct cat atg tta att            9556
Phe Trp Ile Asp Leu Asn Glu Asp Ile Ile Lys Pro His Met Leu Ile
3105                3110                3115                3120 gct gca agc aac ctc cag tgg cga cca gaa tcc aaa tca ggc ctt ctt            9604
Ala Ala Ser Asn Leu Gln Trp Arg Pro Glu Ser Lys Ser Gly Leu Leu
3125                3130                3135 act tta ttt gct gga gat ttt tct gtg ttt tct gct agt cca aaa gag            9652
Thr Leu Phe Ala Gly Asp Phe Ser Val Phe Ser Ala Ser Pro Lys Glu
3140                3145                3150 ggc cac ttt caa gag aca ttc aac aaa atg aaa aat act gtt gag aat            9700
Gly His Phe Gln Glu Thr Phe Asn Lys Met Lys Asn Thr Val Glu Asn
3155                3160                3165 att gac ata ctt tgc aat gaa gca gaa aac aag ctt atg cat ata ctg            9748
Ile Asp Ile Leu Cys Asn Glu Ala Glu Asn Lys Leu Met His Ile Leu
3170                3175                3180 cat gca aat gat ccc aag tgg tcc acc cca act aaa gac tgt act tca            9796
His Ala Asn Asp Pro Lys Trp Ser Thr Pro Thr Lys Asp Cys Thr Ser
3185                3190                3195                3200 ggg ccg tac act gct caa atc att cct ggt aca gga aac aag ctt ctg            9844
Gly Pro Tyr Thr Ala Gln Ile Ile Pro Gly Thr Gly Asn Lys Leu Leu
3205                3210                3215 atg tct tct cct aat tgt gag ata tat tat caa agt cct tta tca ctt            9892
Met Ser Ser Pro Asn Cys Glu Ile Tyr Tyr Gln Ser Pro Leu Ser Leu
3220                3225                3230 tgt atg gcc aaa agg aag tct gtt tcc aca cct gtc tca gcc cag atg            9940
Cys Met Ala Lys Arg Lys Ser Val Ser Thr Pro Val Ser Ala Gln Met
3235                3240                3245 act tca aag tct tgt aaa ggg gag aaa gag att gat gac caa aag aac            9988
Thr Ser Lys Ser Cys Lys Gly Glu Lys Glu Ile Asp Asp Gln Lys Asn
3250                3255                3260 tgc aaa aag aga aga gcc ttg gat ttc ttg agt aga ctg cct tta cct            10036
Cys Lys Lys Arg Arg Ala Leu Asp Phe Leu Ser Arg Leu Pro Leu Pro
3265                3270                3275                3280 cca cct gtt agt ccc att tgt aca ttt gtt tct ccg gct gca cag aag            10084
Pro Pro Val Ser Pro Ile Cys Thr Phe Val Ser Pro Ala Ala Gln Lys
3285                3290                3295 gca ttt cag cca cca agg agt tgt ggc acc aaa tac gaa aca ccc ata            10132
Ala Phe Gln Pro Pro Arg Ser Cys Gly Thr Lys Tyr Glu Thr Pro Ile
3300                3305                3310 aag aaa aaa gaa ctg aat tct cct cag atg act cca ttt aaa aaa ttc            10180
Lys Lys Lys Glu Leu Asn Ser Pro Gln Met Thr Pro Phe Lys Lys Phe
3315                3320                3325 aat gaa att tct ctt ttg gaa agt aat tca ata gct gac gaa gaa ctt            10228
Asn Glu Ile Ser Leu Leu Glu Ser Asn Ser Ile Ala Asp Glu Glu Leu
3330                3335                3340 gca ttg ata aat acc caa gct ctt ttg tct ggt tca aca gga gaa aaa            10276
```

-continued

| | |
|---|---|
| Ala Leu Ile Asn Thr Gln Ala Leu Leu Ser Gly Ser Thr Gly Glu Lys<br>3345                    3350                    3355                    3360 | |
| caa ttt ata tct gtc agt gaa tcc act agg act gct ccc acc agt tca<br>Gln Phe Ile Ser Val Ser Glu Ser Thr Arg Thr Ala Pro Thr Ser Ser<br>3365                    3370                    3375 | 10324 |
| gaa gat tat ctc aga ctg aaa cga cgt tgt act aca tct ctg atc aaa<br>Glu Asp Tyr Leu Arg Leu Lys Arg Arg Cys Thr Thr Ser Leu Ile Lys<br>3380                    3385                    3390 | 10372 |
| gaa cag gag agt tcc cag gcc agt acg gaa gaa tgt gag aaa aat aag<br>Glu Gln Glu Ser Ser Gln Ala Ser Thr Glu Glu Cys Glu Lys Asn Lys<br>3395                    3400                    3405 | 10420 |
| cag gac aca att aca act aaa aaa tat atc taagcatttg caaaggcgac<br>Gln Asp Thr Ile Thr Thr Lys Lys Tyr Ile<br>3410                    3415 | 10470 |
| aataaattat tgacgcttaa cctttccagt ttataagact ggaatataat ttcaaaccac | 10530 |
| acattagtac ttatgttgcm caatgagaaa agaaattagt ttcaaattta cctcagcgtt | 10590 |
| tgtgtatcgg gcaaaaatcg ttttgcccga ttccgtattg gtatactttt gcctcagttg | 10650 |
| catatcctaa aactaaatgt aatttattaa ctaatcaaga aaaacatctt tggctgagct | 10710 |
| cggtggctca tgcctgtaat cccaacactt tgagaagctg aggtgggagg agtgcttgag | 10770 |
| gccaggagtt caagaccagc ctgggcaaca tagggagacc ccatctttac gaagaaaaaa | 10830 |
| aaaaagggga aagaaaatc ttttaaatct ttggatttca ctacaagtat tattttacaa | 10890 |
| gtgaaataaa cataccattt tcttttagat tgtgtcatta aatggaatga ggtctcttag | 10950 |
| tacagttatt ttgatgcaga taattccttt tagtttagct actattttag gggattttt | 11010 |
| ttagaggtaa ctcactatga aatagttccc cttaatgcaa atatgttggt tctgcaatag | 11070 |
| ttccatcctg ttcaaaartc rggrtgaawa tgaagagtgg tgttyccttt tgagcaattc | 11130 |
| tcatccttaa gtcagcrtga ttataagaaa aatagaaccc ycagtgtaac yctaattcct | 11190 |
| ttttrctatt ccagtgtgat ctctgaaakt aaattacttc mactaaaaat tcaaaaacttt | 11250 |
| waamtcagaa rawttcawag twgatttatt ttt | 11283 |

(2) INFORMATION FOR SEQ ID NO:4:

(i) SEQUENCE CHARACTERISTICS:
        (A) LENGTH: 3418
        (B) TYPE: amino acid
        (C) STRANDEDNESS: single
        (D) TOPOLOGY: unknown (ii) MOLECULE TYPE: protein (iii) HYPOTHETICAL: no (iv) ANTI-SENSE: no (v) ORIGINAL SOURCE:
        (A) ORGANISM: Homo sapiens sapiens
        (C) INDIVIDUAL ISOLATE:
        (D) DEVELOPMENTAL STAGE: adult
        (F) TISSUE TYPE: female breast
        (G) CELL TYPE: normal breast tissue
        (H) CELL LINE: HMEC
        (I) ORGANELLE: no (ix) FEATURE:
        (A) NAME/KEY: BRCA2 protein
        (B) LOCATION: 1 to 3418; Genbank locus HSU43746
        (C) IDENTIFICATION METHOD:
        (D) OTHER INFORMATION: BRCA2 protein has a negative
            regulatory effect on growth of human mammary cells.

(x) PUBLICATION INFORMATION:

-continued

```
    (A) AUTHORS:  Wooster, R. et al.
    (B) TITLE:  Identification of the breast cancer
         susceptability gene BRCA2
    (C) JOURNAL:  Nature
    (D) VOLUME:  379
    (E) PAGES:  789-792
    (F) DATE:  1995
    (K) RELEVANT RESIDUES IN SEQ ID NO:4:  granin box
         domain at amino acids 3334-3344

(xi) SEQUENCE DESCRIPTION:  SEQ ID NO:4:

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Tyr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
```

-continued

```
            355                 360                 365
Asn Val Ala His Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
                420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
    450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
                500                 505                 510

Lys Glu Thr Phe Asn Ala Ser Phe Ser Gly His Met Thr Asp Pro Asn
            515                 520                 525

Phe Lys Lys Glu Thr Glu Ala Ser Glu Ser Gly Leu Glu Ile His Thr
530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Phe Tyr Lys Gly Lys Lys Ile Pro Lys Asp
            595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
                660                 665                 670

Asn Glu Thr Cys Ser Asn Asn Thr Val Ile Ser Gln Asp Leu Asp Tyr
            675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Val Ser Asp Ile Lys Glu Val Leu Ala Ala
                725                 730                 735

Ala Cys His Pro Val Gln His Ser Lys Val Glu Tyr Ser Asp Thr Asp
                740                 745                 750

Phe Gln Ser Gln Lys Ser Leu Leu Tyr Asp His Glu Asn Ala Ser Thr
            755                 760                 765

Leu Ile Leu Thr Pro Thr Ser Lys Asp Val Leu Ser Asn Leu Val Met
770                 775                 780
```

-continued

```
Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
        995                 1000                1005

Phe Arg Thr Ala Ser Asn Lys Glu Ile Lys Leu Ser Glu His Asn Ile
        1010                1015                1020

Lys Lys Ser Lys Met Phe Phe Lys Asp Ile Glu Glu Gln Tyr Pro Thr
1025                1030                1035                1040

Ser Leu Ala Cys Val Glu Ile Val Asn Thr Leu Ala Leu Asp Asn Gln
                1045                1050                1055

Lys Lys Leu Ser Lys Pro Gln Ser Ile Asn Thr Val Ser Ala His Leu
            1060                1065                1070

Gln Ser Ser Val Val Val Ser Asp Cys Lys Asn Ser His Ile Thr Pro
        1075                1080                1085

Gln Met Leu Phe Ser Lys Gln Asp Phe Asn Ser Asn His Asn Leu Thr
        1090                1095                1100

Pro Ser Gln Lys Ala Glu Ile Thr Glu Leu Ser Thr Ile Leu Glu Glu
1105                1110                1115                1120

Ser Gly Ser Gln Phe Glu Phe Thr Gln Phe Arg Lys Pro Ser Tyr Ile
                1125                1130                1135

Leu Gln Lys Ser Thr Phe Glu Val Pro Glu Asn Gln Met Thr Ile Leu
            1140                1145                1150

Lys Thr Thr Ser Glu Glu Cys Arg Asp Ala Asp Leu His Val Ile Met
        1155                1160                1165

Asn Ala Pro Ser Ile Gly Gln Val Asp Ser Ser Lys Gln Phe Glu Gly
        1170                1175                1180

Thr Val Glu Ile Lys Arg Lys Phe Ala Gly Leu Leu Lys Asn Asp Cys
1185                1190                1195                1200
```

-continued

```
Asn Lys Ser Ala Ser Gly Tyr Leu Thr Asp Glu Asn Glu Val Gly Phe
            1205                1210                1215
Arg Gly Phe Tyr Ser Ala His Gly Thr Lys Leu Asn Val Ser Thr Glu
            1220                1225                1230
Ala Leu Gln Lys Ala Val Lys Leu Phe Ser Asp Ile Glu Asn Ile Ser
            1235                1240                1245
Glu Glu Thr Ser Ala Glu Val His Pro Ile Ser Leu Ser Ser Ser Lys
            1250                1255                1260
Cys His Asp Ser Val Val Ser Met Phe Lys Ile Glu Asn His Asn Asp
1265                1270                1275                1280
Lys Thr Val Ser Glu Lys Asn Asn Lys Cys Gln Leu Ile Leu Gln Asn
            1285                1290                1295
Asn Ile Glu Met Thr Thr Gly Thr Phe Val Glu Ile Thr Glu Asn
            1300                1305                1310
Tyr Lys Arg Asn Thr Glu Asn Glu Asp Asn Lys Tyr Thr Ala Ala Ser
            1315                1320                1325
Arg Asn Ser His Asn Leu Glu Phe Asp Gly Ser Asp Ser Ser Lys Asn
            1330                1335                1340
Asp Thr Val Cys Ile His Lys Asp Glu Thr Asp Leu Leu Phe Thr Asp
1345                1350                1355                1360
Gln His Asn Ile Cys Leu Lys Leu Ser Gly Gln Phe Met Lys Glu Gly
            1365                1370                1375
Asn Thr Gln Ile Lys Glu Asp Leu Ser Asp Leu Thr Phe Leu Glu Val
            1380                1385                1390
Ala Lys Ala Gln Glu Ala Cys His Gly Asn Thr Ser Asn Lys Glu Gln
            1395                1400                1405
Leu Thr Ala Thr Lys Thr Glu Gln Asn Ile Lys Asp Phe Glu Thr Ser
            1410                1415                1420
Asp Thr Phe Phe Gln Thr Ala Ser Gly Lys Asn Ile Ser Val Ala Lys
1425                1430                1435                1440
Glu Leu Phe Asn Lys Ile Val Asn Phe Phe Asp Gln Lys Pro Glu Glu
            1445                1450                1455
Leu His Asn Phe Ser Leu Asn Ser Glu Leu His Ser Asp Ile Arg Lys
            1460                1465                1470
Asn Lys Met Asp Ile Leu Ser Tyr Glu Glu Thr Asp Ile Val Lys His
            1475                1480                1485
Lys Ile Leu Lys Glu Ser Val Pro Val Gly Thr Gly Asn Gln Leu Val
            1490                1495                1500
Thr Phe Gln Gly Gln Pro Glu Arg Asp Glu Lys Ile Lys Glu Pro Thr
1505                1510                1515                1520
Leu Leu Gly Phe His Thr Ala Ser Gly Lys Lys Val Lys Ile Ala Lys
            1525                1530                1535
Glu Ser Leu Asp Lys Val Lys Asn Leu Phe Asp Glu Lys Glu Gln Gly
            1540                1545                1550
Thr Ser Glu Ile Thr Ser Phe Ser His Gln Trp Ala Lys Thr Leu Lys
            1555                1560                1565
Tyr Arg Glu Ala Cys Lys Asp Leu Glu Leu Ala Cys Glu Thr Ile Glu
            1570                1575                1580
Ile Thr Ala Ala Pro Lys Cys Lys Glu Met Gln Asn Ser Leu Asn Asn
1585                1590                1595                1600
Asp Lys Asn Leu Val Ser Ile Glu Thr Val Val Pro Pro Lys Leu Leu
            1605                1610                1615
Ser Asp Asn Leu Cys Arg Gln Thr Glu Asn Leu Lys Thr Ser Lys Ser
```

-continued

```
                1620                1625                1630
Ile Phe Leu Lys Val Lys Val His Glu Asn Val Glu Lys Glu Thr Ala
            1635                1640                1645
Lys Ser Pro Ala Thr Cys Tyr Thr Asn Gln Ser Pro Tyr Ser Val Ile
        1650                1655                1660
Glu Asn Ser Ala Leu Ala Phe Tyr Thr Ser Cys Ser Arg Lys Thr Ser
1665                1670                1675                1680
Val Ser Gln Thr Ser Leu Leu Glu Ala Lys Lys Trp Leu Arg Glu Gly
                1685                1690                1695
Ile Phe Asp Gly Gln Pro Glu Arg Ile Asn Thr Ala Asp Tyr Val Gly
            1700                1705                1710
Asn Tyr Leu Tyr Glu Asn Asn Ser Asn Ser Thr Ile Ala Glu Asn Asp
        1715                1720                1725
Lys Asn His Leu Ser Glu Lys Gln Asp Thr Tyr Leu Ser Asn Ser Ser
    1730                1735                1740
Met Ser Asn Ser Tyr Ser Tyr His Ser Asp Glu Val Tyr Asn Asp Ser
1745                1750                1755                1760
Gly Tyr Leu Ser Lys Asn Lys Leu Asp Ser Gly Ile Glu Pro Val Leu
                1765                1770                1775
Lys Asn Val Glu Asp Gln Lys Asn Thr Ser Phe Ser Lys Val Ile Ser
            1780                1785                1790
Asn Val Lys Asp Ala Asn Ala Tyr Pro Gln Thr Val Asn Glu Asp Ile
        1795                1800                1805
Cys Val Glu Glu Leu Val Thr Ser Ser Pro Cys Lys Asn Lys Asn
    1810                1815                1820
Ala Ala Ile Lys Leu Ser Ile Ser Asn Ser Asn Asn Phe Glu Val Gly
1825                1830                1835                1840
Pro Pro Ala Phe Arg Ile Ala Ser Gly Lys Ile Arg Leu Cys Ser His
                1845                1850                1855
Glu Thr Ile Lys Lys Val Lys Asp Ile Phe Thr Asp Ser Phe Ser Lys
            1860                1865                1870
Val Ile Lys Glu Asn Asn Glu Asn Lys Ser Lys Ile Cys Gln Thr Lys
        1875                1880                1885
Ile Met Ala Gly Cys Tyr Glu Ala Leu Asp Asp Ser Glu Asp Ile Leu
    1890                1895                1900
His Asn Ser Leu Asp Asn Asp Glu Cys Ser Met His Ser His Lys Val
1905                1910                1915                1920
Phe Ala Asp Ile Gln Ser Glu Ile Leu Gln His Asn Gln Asn Met
                1925                1930                1935
Ser Gly Leu Glu Lys Val Ser Lys Ile Ser Pro Cys Asp Val Ser Leu
            1940                1945                1950
Glu Thr Ser Asp Ile Cys Lys Cys Ser Ile Gly Lys Leu His Lys Ser
        1955                1960                1965
Val Ser Ser Ala Asn Thr Cys Gly Ile Phe Ser Thr Ala Ser Gly Lys
    1970                1975                1980
Ser Val Gln Val Ser Asp Ala Ser Leu Gln Asn Ala Arg Gln Val Phe
1985                1990                1995                2000
Ser Glu Ile Glu Asp Ser Thr Lys Gln Val Phe Ser Lys Val Leu Phe
                2005                2010                2015
Lys Ser Asn Glu His Ser Asp Gln Leu Thr Arg Glu Glu Asn Thr Ala
            2020                2025                2030
Ile Arg Thr Pro Glu His Leu Ile Ser Gln Lys Gly Phe Ser Tyr Asn
        2035                2040                2045
```

-continued

```
Val Val Asn Ser Ser Ala Phe Ser Gly Phe Ser Thr Ala Ser Gly Lys
    2050                2055                2060

Gln Val Ser Ile Leu Glu Ser Ser Leu His Lys Val Lys Gly Val Leu
2065                2070                2075                2080

Glu Glu Phe Asp Leu Ile Arg Thr Glu His Ser Leu His Tyr Ser Pro
                2085                2090                2095

Thr Ser Arg Gln Asn Val Ser Lys Ile Leu Pro Arg Val Asp Lys Arg
            2100                2105                2110

Asn Pro Glu His Cys Val Asn Ser Glu Met Glu Lys Thr Cys Ser Lys
        2115                2120                2125

Glu Phe Lys Leu Ser Asn Asn Leu Asn Val Glu Gly Gly Ser Ser Glu
    2130                2135                2140

Asn Asn His Ser Ile Lys Val Ser Pro Tyr Leu Ser Gln Phe Gln Gln
2145                2150                2155                2160

Asp Lys Gln Gln Leu Val Leu Gly Thr Lys Val Ser Leu Val Glu Asn
                2165                2170                2175

Ile His Val Leu Gly Lys Glu Gln Ala Ser Pro Lys Asn Val Lys Met
            2180                2185                2190

Glu Ile Gly Lys Thr Glu Thr Phe Ser Asp Val Pro Val Lys Thr Asn
        2195                2200                2205

Ile Glu Val Cys Ser Thr Tyr Ser Lys Asp Ser Glu Asn Tyr Phe Glu
    2210                2215                2220

Thr Glu Ala Val Glu Ile Ala Lys Ala Phe Met Glu Asp Asp Glu Leu
2225                2230                2235                2240

Thr Asp Ser Lys Leu Pro Ser His Ala Thr His Ser Leu Phe Thr Cys
                2245                2250                2255

Pro Glu Asn Glu Glu Met Val Leu Ser Asn Ser Arg Ile Gly Lys Arg
            2260                2265                2270

Arg Gly Glu Pro Leu Ile Leu Val Gly Glu Pro Ser Ile Lys Arg Asn
        2275                2280                2285

Leu Leu Asn Glu Phe Asp Arg Ile Ile Glu Asn Gln Glu Lys Ser Leu
    2290                2295                2300

Lys Ala Ser Lys Ser Thr Pro Asp Gly Thr Ile Lys Asp Arg Arg Leu
2305                2310                2315                2320

Phe Met His His Val Ser Leu Glu Pro Ile Thr Cys Val Pro Phe Arg
                2325                2330                2335

Thr Thr Lys Glu Arg Gln Glu Ile Gln Asn Pro Asn Phe Thr Ala Pro
            2340                2345                2350

Gly Gln Glu Phe Leu Ser Lys Ser His Leu Tyr Glu His Leu Thr Leu
        2355                2360                2365

Glu Lys Ser Ser Ser Asn Leu Ala Val Ser Gly His Pro Phe Tyr Gln
    2370                2375                2380

Val Ser Ala Thr Arg Asn Glu Lys Met Arg His Leu Ile Thr Thr Gly
2385                2390                2395                2400

Arg Pro Thr Lys Val Phe Val Pro Pro Phe Lys Thr Lys Ser His Phe
                2405                2410                2415

His Arg Val Glu Gln Cys Val Arg Asn Ile Asn Leu Glu Glu Asn Arg
            2420                2425                2430

Gln Lys Gln Asn Ile Asp Gly His Gly Ser Asp Asp Ser Lys Asn Lys
        2435                2440                2445

Ile Asn Asp Asn Glu Ile His Gln Phe Asn Lys Asn Asn Ser Asn Gln
    2450                2455                2460
```

-continued

```
Ala Ala Ala Val Thr Phe Thr Lys Cys Glu Glu Pro Leu Asp Leu
2465                2470                2475                2480

Ile Thr Ser Leu Gln Asn Ala Arg Asp Ile Gln Asp Met Arg Ile Lys
                2485                2490                2495

Lys Lys Gln Arg Gln Arg Val Phe Pro Gln Pro Gly Ser Leu Tyr Leu
                2500                2505                2510

Ala Lys Thr Ser Thr Leu Pro Arg Ile Ser Leu Lys Ala Ala Val Gly
                2515                2520                2525

Gly Gln Val Pro Ser Ala Cys Ser His Lys Gln Leu Tyr Thr Tyr Gly
                2530                2535                2540

Val Ser Lys His Cys Ile Lys Ile Asn Ser Lys Asn Ala Glu Ser Phe
2545                2550                2555                2560

Gln Phe His Thr Glu Asp Tyr Phe Gly Lys Glu Ser Leu Trp Thr Gly
                2565                2570                2575

Lys Gly Ile Gln Leu Ala Asp Gly Gly Trp Leu Ile Pro Ser Asn Asp
                2580                2585                2590

Gly Lys Ala Gly Lys Glu Glu Phe Tyr Arg Ala Leu Cys Asp Thr Pro
                2595                2600                2605

Gly Val Asp Pro Lys Leu Ile Ser Arg Ile Trp Val Tyr Asn His Tyr
                2610                2615                2620

Arg Trp Ile Ile Trp Lys Leu Ala Ala Met Glu Cys Ala Phe Pro Lys
2625                2630                2635                2640

Glu Phe Ala Asn Arg Cys Leu Ser Pro Glu Arg Val Leu Leu Gln Leu
                2645                2650                2655

Lys Tyr Arg Tyr Asp Thr Glu Ile Asp Arg Ser Arg Arg Ser Ala Ile
                2660                2665                2670

Lys Lys Ile Met Glu Arg Asp Asp Thr Ala Ala Lys Thr Leu Val Leu
                2675                2680                2685

Cys Val Ser Asp Ile Ile Ser Leu Ser Ala Asn Ile Ser Glu Thr Ser
                2690                2695                2700

Ser Asn Lys Thr Ser Ser Ala Asp Thr Gln Lys Val Ala Ile Ile Glu
2705                2710                2715                2720

Leu Thr Asp Gly Trp Tyr Ala Val Lys Ala Gln Leu Asp Pro Pro Leu
                2725                2730                2735

Leu Ala Val Leu Lys Asn Gly Arg Leu Thr Val Gly Gln Lys Ile Ile
                2740                2745                2750

Leu His Gly Ala Glu Leu Val Gly Ser Pro Asp Ala Cys Thr Pro Leu
                2755                2760                2765

Glu Ala Pro Glu Ser Leu Met Leu Lys Ile Ser Ala Asn Ser Thr Arg
                2770                2775                2780

Pro Ala Arg Trp Tyr Thr Lys Leu Gly Phe Phe Pro Asp Pro Arg Pro
2785                2790                2795                2800

Phe Pro Leu Pro Leu Ser Ser Leu Phe Ser Asp Gly Gly Asn Val Gly
                2805                2810                2815

Cys Val Asp Val Ile Ile Gln Arg Ala Tyr Pro Ile Gln Arg Met Glu
                2820                2825                2830

Lys Thr Ser Ser Gly Leu Tyr Ile Phe Arg Asn Glu Arg Glu Glu Glu
                2835                2840                2845

Lys Glu Ala Ala Lys Tyr Val Glu Ala Gln Gln Lys Arg Leu Glu Ala
                2850                2855                2860

Leu Phe Thr Lys Ile Gln Glu Glu Phe Glu Glu His Glu Glu Asn Thr
2865                2870                2875                2880

Thr Lys Pro Tyr Leu Pro Ser Arg Ala Leu Thr Arg Gln Gln Val Arg
```

-continued

```
                 2885                2890                2895
Ala Leu Gln Asp Gly Ala Glu Leu Tyr Glu Ala Val Lys Asn Ala Ala
                 2900                2905                2910

Asp Pro Ala Tyr Leu Glu Gly Tyr Phe Ser Glu Gln Leu Arg Ala
                 2915                2920                2925

Leu Asn Asn His Arg Gln Met Leu Asn Asp Lys Lys Gln Ala Gln Ile
                 2930                2935                2940

Gln Leu Glu Ile Arg Lys Ala Met Glu Ser Ala Glu Gln Lys Glu Gln
2945                 2950                2955                2960

Gly Leu Ser Arg Asp Val Thr Thr Val Trp Lys Leu Arg Ile Val Ser
                 2965                2970                2975

Tyr Ser Lys Lys Glu Lys Asp Ser Val Ile Leu Ser Ile Trp Arg Pro
                 2980                2985                2990

Ser Ser Asp Leu Tyr Ser Leu Leu Thr Glu Gly Lys Arg Tyr Arg Ile
                 2995                3000                3005

Tyr His Leu Ala Thr Ser Lys Ser Lys Ser Lys Ser Glu Arg Ala Asn
                 3010                3015                3020

Ile Gln Leu Ala Ala Thr Lys Lys Thr Gln Tyr Gln Gln Leu Pro Val
3025                 3030                3035                3040

Ser Asp Glu Ile Leu Phe Gln Ile Tyr Gln Pro Arg Glu Pro Leu His
                 3045                3050                3055

Phe Ser Lys Phe Leu Asp Pro Asp Phe Gln Pro Ser Cys Ser Glu Val
                 3060                3065                3070

Asp Leu Ile Gly Phe Val Val Ser Val Val Lys Lys Thr Gly Leu Ala
                 3075                3080                3085

Pro Phe Val Tyr Leu Ser Asp Glu Cys Tyr Asn Leu Leu Ala Ile Lys
                 3090                3095                3100

Phe Trp Ile Asp Leu Asn Glu Asp Ile Ile Lys Pro His Met Leu Ile
3105                 3110                3115                3120

Ala Ala Ser Asn Leu Gln Trp Arg Pro Glu Ser Lys Ser Gly Leu Leu
                 3125                3130                3135

Thr Leu Phe Ala Gly Asp Phe Ser Val Phe Ser Ala Ser Pro Lys Glu
                 3140                3145                3150

Gly His Phe Gln Glu Thr Phe Asn Lys Met Lys Asn Thr Val Glu Asn
                 3155                3160                3165

Ile Asp Ile Leu Cys Asn Glu Ala Glu Asn Lys Leu Met His Ile Leu
                 3170                3175                3180

His Ala Asn Asp Pro Lys Trp Ser Thr Pro Thr Lys Asp Cys Thr Ser
3185                 3190                3195                3200

Gly Pro Tyr Thr Ala Gln Ile Ile Pro Gly Thr Gly Asn Lys Leu Leu
                 3205                3210                3215

Met Ser Ser Pro Asn Cys Glu Ile Tyr Tyr Gln Ser Pro Leu Ser Leu
                 3220                3225                3230

Cys Met Ala Lys Arg Lys Ser Val Ser Thr Pro Val Ser Ala Gln Met
                 3235                3240                3245

Thr Ser Lys Ser Cys Lys Gly Glu Lys Glu Ile Asp Asp Gln Lys Asn
                 3250                3255                3260

Cys Lys Lys Arg Arg Ala Leu Asp Phe Leu Ser Arg Leu Pro Leu Pro
3265                 3270                3275                3280

Pro Pro Val Ser Pro Ile Cys Thr Phe Val Ser Pro Ala Ala Gln Lys
                 3285                3290                3295

Ala Phe Gln Pro Pro Arg Ser Cys Gly Thr Lys Tyr Glu Thr Pro Ile
                 3300                3305                3310
```

```
Lys Lys Lys Glu Leu Asn Ser Pro Gln Met Thr Pro Phe Lys Lys Phe
        3315                3320                3325
Asn Glu Ile Ser Leu Leu Glu Ser Asn Ser Ile Ala Asp Glu Glu Leu
        3330                3335                3340
Ala Leu Ile Asn Thr Gln Ala Leu Leu Ser Gly Ser Thr Gly Glu Lys
3345                3350                3355                3360
Gln Phe Ile Ser Val Ser Glu Ser Thr Arg Thr Ala Pro Thr Ser Ser
                3365                3370                3375
Glu Asp Tyr Leu Arg Leu Lys Arg Arg Cys Thr Thr Ser Leu Ile Lys
            3380                3385                3390
Glu Gln Glu Ser Ser Gln Ala Ser Thr Glu Glu Cys Glu Lys Asn Lys
        3395                3400                3405
Gln Asp Thr Ile Thr Thr Lys Lys Tyr Ile
    3410                3415
```

(2) INFORMATION FOR SEQ ID NO:5:

(i) SEQUENCE CHARACTERISTICS:
        (A) LENGTH:19
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
        (A) ORGANISM: Homo sapiens sapiens
        (C) INDIVIDUAL ISOLATE:
        (D) DEVELOPMENTAL STAGE: adult
        (F) TISSUE TYPE: female breast
        (G) CELL TYPE:   normal breast tissue
        (H) CELL LINE: HMEC
        (I) ORGANELLE: no (ix) FEATURE:
        (A) NAME/KEY: BRCA1 C-19 antigen
        (B) LOCATION: 1845 to 1863
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:5

(xi) SEQUENCE DESCRIPTION: SEQ ID NO:5:

```
Tyr Gln Cys Gln Glu Leu Asp Thr Tyr Leu Ile Pro Gln Ile Pro His
1               5                   10                  15
Ser His Tyr
```

(2) INFORMATION FOR SEQ ID NO:6:

(i) SEQUENCE CHARACTERISTICS:
        (A) LENGTH:  20
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
              (A) ORGANISM: Homo sapiens sapiens
              (C) INDIVIDUAL ISOLATE:
              (D) DEVELOPMENTAL STAGE: adult
              (F) TISSUE TYPE: female breast
              (G) CELL TYPE:  normal breast tissue
              (H) CELL LINE: HMEC
              (I) ORGANELLE: no (ix) FEATURE:
              (A) NAME/KEY: BRCA1 C-20 antigen
              (B) LOCATION: 1844 to 1863
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) PAGES:
              (F) DATE:
              (K) RELEVANT RESIDUES IN SEQ ID NO:6

(xi) SEQUENCE DESCRIPTION:  SEQ ID NO:6:

Leu Tyr Gln Cys Gln Glu Leu Asp Thr Tyr Leu Ile Pro Gln Ile Pro
1               5                  10                  15

His Ser His Tyr
 20

(2) INFORMATION FOR SEQ ID NO:7:

(i) SEQUENCE CHARACTERISTICS:
              (A) LENGTH:   20
              (B) TYPE: amino acid
              (C) STRANDEDNESS: single
              (D) TOPOLOGY: unknown (ii) MOLECULE TYPE: peptide (iii) HYPOTHETICAL: no (iv) ANTI-SENSE: no (v) ORIGINAL SOURCE:
              (A) ORGANISM: Homo sapiens sapiens
              (C) INDIVIDUAL ISOLATE:
              (D) DEVELOPMENTAL STAGE: adult
              (F) TISSUE TYPE: female breast
              (G) CELL TYPE:  normal breast tissue
              (H) CELL LINE: HMEC
              (I) ORGANELLE: no (ix) FEATURE:
              (A) NAME/KEY: BRCA1 D-20 antigen
              (B) LOCATION: 1 to 20
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) PAGES:
              (F) DATE:
              (K) RELEVANT RESIDUES IN SEQ ID NO:7

(xi) SEQUENCE DESCRIPTION:  SEQ ID NO:7:

Met Asp Leu Ser Ala Leu Arg Val Glu Glu Val Gln Asn Val Ile Asn
1               5                  10                  15

Ala Met Gln Lys
20

(2) INFORMATION FOR SEQ ID NO:8:

(i) SEQUENCE CHARACTERISTICS:
        (A) LENGTH: 10
        (B) TYPE: amino acid
        (C) STRANDEDNESS: single
        (D) TOPOLOGY: unknown (ii) MOLECULE TYPE: peptide (iii) HYPOTHETICAL:

(iv) ANTI-SENSE: no (v) ORIGINAL SOURCE:
        (A) ORGANISM:
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: Granin Consensus Sequence
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:8:

(xi) SEQUENCE DESCRIPTION: SEQ ID NO:8:

Glu Asn Leu Ser Xaa Xaa Asp Xaa Glu Leu
1             5                  10

(2) INFORMATION FOR SEQ ID NO:9:

(i) SEQUENCE CHARACTERISTICS:
        (A) LENGTH: 10
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
        (A) ORGANISM: Human
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: BRCA1 Granin Sequence
        (B) LOCATION: amino acids 1214-1223 of BRCA1 protein
        (C) IDENTIFICATION METHOD:
        (D) OTHER INFORMATION:

(x) PUBLICATION INFORMATION:

-continued

```
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:9:

(xi) SEQUENCE DESCRIPTION: SEQ ID NO:9:

Glu Asn Leu Ser Ser Glu Asp Glu Glu Leu
1               5                   10

(2) INFORMATION FOR SEQ ID NO:10:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Rhesus
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: BRCA1 Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:10:

(xi) SEQUENCE DESCRIPTION: SEQ ID NO:10:

Glu Asn Leu Ser Ser Glu Asp Glu Glu Leu
1               5                   10

(2) INFORMATION FOR SEQ ID NO:11:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Mouse
            (C) INDIVIDUAL ISOLATE:
            (D) DEVELOPMENTAL STAGE:
            (F) TISSUE TYPE:
            (G) CELL TYPE:
            (H) CELL LINE:
```

```
            (I) ORGANELLE:

(ix) FEATURE:
            (A) NAME/KEY: BRCA1 Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:11:

(xi) SEQUENCE DESCRIPTION:  SEQ ID NO:11:

Glu Ser Asp Ser Thr Glu Asp Glu Asp Leu
1               5                   10

(2) INFORMATION FOR SEQ ID NO:12:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Human
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: BRCA2 Granin Sequence
            (B) LOCATION: amino acids 3334-3344 of BRCA2 protein
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:12:

(xi) SEQUENCE DESCRIPTION:  SEQ ID NO:12:

Glu Ser Asn Ser Ile Ala Asp Glu Glu Leu
1               5                   10

(2) INFORMATION FOR SEQ ID NO:13:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no
```

```
        (iv) ANTI-SENSE: no (v) ORIGINAL SOURCE:
             (A) ORGANISM: Human
             (C) INDIVIDUAL ISOLATE:
             (D) DEVELOPMENTAL STAGE:
             (F) TISSUE TYPE:
             (G) CELL TYPE:
             (H) CELL LINE:
             (I) ORGANELLE:

(ix) FEATURE:
             (A) NAME/KEY: Chromogranin A Granin Sequence
             (B) LOCATION:
             (C) IDENTIFICATION METHOD:
             (D) OTHER INFORMATION:

(x) PUBLICATION INFORMATION:
             (A) AUTHORS:
             (B) TITLE:
             (C) JOURNAL:
             (D) VOLUME:
             (E) PAGES:
             (F) DATE:
             (K) RELEVANT RESIDUES IN SEQ ID NO:13:

(xi) SEQUENCE DESCRIPTION:   SEQ ID NO:13:

Glu Ser Leu Ser Ala Ile Glu Ala Glu Leu
1               5                   10

(2) INFORMATION FOR SEQ ID NO:14:

(i) SEQUENCE CHARACTERISTICS:
             (A) LENGTH: 10
             (B) TYPE: amino acid
             (C) STRANDEDNESS: single
             (D) TOPOLOGY: unknown (ii) MOLECULE TYPE: peptide (iii) HYPOTHETICAL: no (iv) ANTI-SENSE: no (v) ORIGINAL SOURCE:
             (A) ORGANISM: Bovine
             (C) INDIVIDUAL ISOLATE:
             (D) DEVELOPMENTAL STAGE:
             (F) TISSUE TYPE:
             (G) CELL TYPE:
             (H) CELL LINE:
             (I) ORGANELLE:

(ix) FEATURE:
             (A) NAME/KEY: Chromogranin A Granin Sequence
             (B) LOCATION:
             (C) IDENTIFICATION METHOD:
             (D) OTHER INFORMATION:

(x) PUBLICATION INFORMATION:
             (A) AUTHORS:
             (B) TITLE:
             (C) JOURNAL:
             (D) VOLUME:
             (E) PAGES:
             (F) DATE:
             (K) RELEVANT RESIDUES IN SEQ ID NO:14:

(xi) SEQUENCE DESCRIPTION:   SEQ ID NO:14:

Glu Ser Leu Ser Ala Ile Glu Ala Glu Leu
1               5                   10

(2) INFORMATION FOR SEQ ID NO:15:

(i) SEQUENCE CHARACTERISTICS:
```

```
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Rat
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Chromogranin A Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:15:

(xi) SEQUENCE DESCRIPTION:  SEQ ID NO:15:

Glu Ser Leu Ser Ala Ile Glu Ala Glu Leu
1               5                   10

(2) INFORMATION FOR SEQ ID NO:16:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Pig
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Chromogranin A Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:16:
```

(xi) SEQUENCE DESCRIPTION: SEQ ID NO:16:

Glu Ser Leu Ser Ala Ile Glu Ala Glu Leu
1               5                   10

(2) INFORMATION FOR SEQ ID NO:17:

(i) SEQUENCE CHARACTERISTICS:
        (A) LENGTH: 10
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
        (A) ORGANISM: Human
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: Chromogranin B Granin Sequence
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:17:

(xi) SEQUENCE DESCRIPTION: SEQ ID NO:17:

Glu Asn Leu Ala Ala Met Asp Leu Glu Leu
1               5                   10

(2) INFORMATION FOR SEQ ID NO:18:

(i) SEQUENCE CHARACTERISTICS:
        (A) LENGTH: 10
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
        (A) ORGANISM:  Bovine
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: Chromogranin B Granin Sequence
        (B) LOCATION:
        (C) IDENTIFICATION METHOD:
        (D) OTHER INFORMATION:

```
    (x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:18:

(xi) SEQUENCE DESCRIPTION: SEQ ID NO:18:

Glu Asn Leu Ala Ala Met Asp Leu Glu Leu
1               5                   10

(2) INFORMATION FOR SEQ ID NO:19:

(i) SEQUENCE CHARACTERISTICS:
         (A) LENGTH: 10
         (B) TYPE: amino acid
         (C) STRANDEDNESS: single
         (D) TOPOLOGY: unknown (ii) MOLECULE TYPE: peptide (iii) HYPOTHETICAL: no (iv) ANTI-SENSE: no (v) ORIGINAL SOURCE:
         (A) ORGANISM: Mouse
         (C) INDIVIDUAL ISOLATE:
         (D) DEVELOPMENTAL STAGE:
         (F) TISSUE TYPE:
         (G) CELL TYPE:
         (H) CELL LINE:
         (I) ORGANELLE:

(ix) FEATURE:
         (A) NAME/KEY: Chromogranin B Granin Sequence
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) PAGES:
         (F) DATE:
         (K) RELEVANT RESIDUES IN SEQ ID NO:19:

(xi) SEQUENCE DESCRIPTION: SEQ ID NO:19:

Glu Asn Leu Ala Ala Met Asp Leu Glu Leu
1               5                   10

(2) INFORMATION FOR SEQ ID NO:20:

(i) SEQUENCE CHARACTERISTICS:
         (A) LENGTH: 10
         (B) TYPE: amino acid
         (C) STRANDEDNESS: single
         (D) TOPOLOGY: unknown (ii) MOLECULE TYPE: peptide (iii) HYPOTHETICAL: no (iv) ANTI-SENSE: no (v) ORIGINAL SOURCE:
         (A) ORGANISM: Human
         (C) INDIVIDUAL ISOLATE:
         (D) DEVELOPMENTAL STAGE:
         (F) TISSUE TYPE:
         (G) CELL TYPE:
```

(H) CELL LINE:
            (I) ORGANELLE:

(ix) FEATURE:
            (A) NAME/KEY: Secretogranin II Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:20:

(xi) SEQUENCE DESCRIPTION:  SEQ ID NO:20:

Glu Asn Leu Asn Asp Lys Asp Gln Glu Leu
1               5                   10

(2) INFORMATION FOR SEQ ID NO:21:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Bovine
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Secretogranin II Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:21:

(xi) SEQUENCE DESCRIPTION:  SEQ ID NO:21:

Glu Asn Leu Asn Asp Lys Asp Gln Glu Leu
1               5                   10

(2) INFORMATION FOR SEQ ID NO:22:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no

```
    (iv) ANTI-SENSE: no (v) ORIGINAL SOURCE:
         (A) ORGANISM:  Rat
         (C) INDIVIDUAL ISOLATE:
         (D) DEVELOPMENTAL STAGE:
         (F) TISSUE TYPE:
         (G) CELL TYPE:
         (H) CELL LINE:
         (I) ORGANELLE:

(ix) FEATURE:
         (A) NAME/KEY: Secretogranin II Granin Sequence
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) PAGES:
         (F) DATE:
         (K) RELEVANT RESIDUES IN SEQ ID NO:22:

(xi) SEQUENCE DESCRIPTION:  SEQ ID NO:22:

Asp Asn Leu Asn Asp Lys Asp Gln Glu Leu
1               5                   10

(2) INFORMATION FOR SEQ ID NO:23:

(i) SEQUENCE CHARACTERISTICS:
         (A) LENGTH: 10
         (B) TYPE: amino acid
         (C) STRANDEDNESS: single
         (D) TOPOLOGY: unknown (ii) MOLECULE TYPE: peptide (iii) HYPOTHETICAL: no (iv) ANTI-SENSE: no (v) ORIGINAL SOURCE:
         (A) ORGANISM: Mouse
         (C) INDIVIDUAL ISOLATE:
         (D) DEVELOPMENTAL STAGE:
         (F) TISSUE TYPE:
         (G) CELL TYPE:
         (H) CELL LINE:
         (I) ORGANELLE:

(ix) FEATURE:
         (A) NAME/KEY: Secretogranin II Granin Sequence
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) PAGES:
         (F) DATE:
         (K) RELEVANT RESIDUES IN SEQ ID NO:23:

(xi) SEQUENCE DESCRIPTION:  SEQ ID NO:23:

Glu Asn Leu Asn Xaa Xaa Asp Gln Glu Leu
1               5                   10

(2) INFORMATION FOR SEQ ID NO:24:
```

```
    (i) SEQUENCE CHARACTERISTICS:
        (A) LENGTH: 10
        (B) TYPE:  amino acid
        (C) STRANDEDNESS:  single
        (D) TOPOLOGY: unknown (ii) MOLECULE TYPE: peptide (iii) HYPOTHETICAL:  no (iv) ANTI-SENSE:  no (v) ORIGINAL SOURCE:
        (A) ORGANISM: Rat
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: Secretogranin III Granin Sequence
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:24:

(xi) SEQUENCE DESCRIPTION:  SEQ ID NO:24:

Glu Asn Leu Asp Glu Thr Ile Ala Leu Gln
1               5                  10

(2) INFORMATION FOR SEQ ID NO:25:

(i) SEQUENCE CHARACTERISTICS:
        (A) LENGTH: 10
        (B) TYPE:  amino acid
        (C) STRANDEDNESS:  single
        (D) TOPOLOGY: unknown (ii) MOLECULE TYPE: peptide (iii) HYPOTHETICAL:  no (iv) ANTI-SENSE:  no (v) ORIGINAL SOURCE:
        (A) ORGANISM: Mouse
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: Secretogranin III Granin Sequence
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:25:
```

```
            (xi) SEQUENCE DESCRIPTION: SEQ ID NO:25:

Glu Asn Leu Asp Glu Thr Ile Ala Leu Gln
1               5                   10

(2) INFORMATION FOR SEQ ID NO:26:

(i) SEQUENCE CHARACTERISTICS:
            (A) LENGTH: 10
            (B) TYPE:  amino acid
            (C) STRANDEDNESS:  single
            (D) TOPOLOGY: unknown (ii) MOLECULE TYPE: peptide (iii) HYPOTHETICAL:  no (iv) ANTI-SENSE:  no (v) ORIGINAL SOURCE:
            (A) ORGANISM: Human
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Secretogranin V Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:26:

(xi) SEQUENCE DESCRIPTION: SEQ ID NO:26:

Gly Asn Ile Pro Asn Ile Val Ala Glu Leu
1               5                   10

(2) INFORMATION FOR SEQ ID NO:27:

(i) SEQUENCE CHARACTERISTICS:
            (A) LENGTH: 10
            (B) TYPE:  amino acid
            (C) STRANDEDNESS:  single
            (D) TOPOLOGY: unknown (ii) MOLECULE TYPE: peptide (iii) HYPOTHETICAL:  no (iv) ANTI-SENSE:  no (v) ORIGINAL SOURCE:
            (A) ORGANISM: Pig
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Secretogranin V Granin Sequence
            (B) LOCATION:
            (C) IDENTIFICATION METHOD:
            (D) OTHER INFORMATION:
```

```
        (x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:27:

(xi) SEQUENCE DESCRIPTION: SEQ ID NO:27:

Gly Asn Ile Pro Asn Ile Val Ala Glu Leu
1               5                   10

(2) INFORMATION FOR SEQ ID NO:28:

(i) SEQUENCE CHARACTERISTICS:
            (A) LENGTH: 10
            (B) TYPE:  amino acid
            (C) STRANDEDNESS:  single
            (D) TOPOLOGY: unknown (ii) MOLECULE TYPE: peptide (iii) HYPOTHETICAL:  no (iv) ANTI-SENSE:  no (v) ORIGINAL SOURCE:
            (A) ORGANISM: Rat
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Secretogranin V Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:28:

(xi) SEQUENCE DESCRIPTION: SEQ ID NO:28:

Gly Asn Ile Pro Asn Ile Val Ala Glu Leu
1               5                   10

(2) INFORMATION FOR SEQ ID NO:29:

(i) SEQUENCE CHARACTERISTICS:
            (A) LENGTH: 10
            (B) TYPE:  amino acid
            (C) STRANDEDNESS:  single
            (D) TOPOLOGY: unknown (ii) MOLECULE TYPE: peptide (iii) HYPOTHETICAL:  no (iv) ANTI-SENSE:  no (v) ORIGINAL SOURCE:
            (A) ORGANISM: Xenopus
            (C) INDIVIDUAL ISOLATE:
            (D) DEVELOPMENTAL STAGE:
            (F) TISSUE TYPE:
```

```
            (G) CELL TYPE:
            (H) CELL LINE:
            (I) ORGANELLE:

(ix) FEATURE:
            (A) NAME/KEY: Secretogranin V Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:29:

(xi) SEQUENCE DESCRIPTION:  SEQ ID NO:29:

Gly Asn Ile Pro Asn Ile Val Ala Glu Leu
1               5                   10
```

Thus, although there have been described particular embodiments of the present invention of a new and useful Characterized BRCA1 and BRCA2 Proteins and Screening and Therapeutic Methods Based on Characterized BRCA1 and BRCA2 Proteins, it is not intended that such references be construed as limitations upon the scope of this invention except as set forth in the following claims. Further, although there have been described certain examples used in the preferred embodiment, it is not intended that such examples be construed as limitations upon the scope of this invention except as set forth in the following claims.

What is claimed is:

1. A method to suppress the growth of an epithelial ovarian tumor in a mammal, the method comprising introducing to an intraperitoneal cavity of the mammal at the site of said tumor a vector comprising a BRCA1 nucleic acid sequence encoding a BRCA1 protein having tumor suppressor activity, the nucleic acid sequence operatively linked to a promoter, wherein production of the BRCA1 protein results in a decrease in the growth rate of said epithelial ovarian tumor.

2. The method of claim 1, wherein the epithelial ovarian tumor comprises sporadic ovarian tumor cells.

3. The method of claim 1, wherein the epithelial ovarian tumor comprises gene-linked hereditary ovarian tumor cells.

4. A method to reduce the growth of an epithelial ovarian tumor in a mammal, the method comprising injecting into the intraperitoneal cavity of said mammal, at the site of said epithelial ovarian tumor, an adenoviral construct comprising BRCA1 cDNA encoding a functionally active BRCA1 polypeptide operably linked to a promoter, wherein said BRCA1 polypeptide is expressed in said epithelial ovarian tumor at a level and for a period of time sufficient to reduce the growth of said epithelial ovarian tumor.

* * * * *